(12) United States Patent
O'Neill et al.

(10) Patent No.: US 11,149,078 B2
(45) Date of Patent: *Oct. 19, 2021

(54) VARIANTS OF TISSUE INHIBITOR OR METALLOPROTIENASE TYPE THREE (TIMP-3), COMPOSITIONS AND METHODS

(71) Applicant: AMGEN INC., Thousand Oaks, CA (US)

(72) Inventors: Jason C. O'Neill, Brier, WA (US); Randal R. Ketchem, Snohomish, WA (US); Taeweon Lee, Palo Alto, CA (US); Vishnu Chintalgattu, Union City, CA (US); Jennitte Leann Stevens, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 719 days.

This patent is subject to a terminal disclaimer.

(21) Appl. No.: 15/547,730

(22) PCT Filed: Aug. 26, 2015

(86) PCT No.: PCT/US2015/046992
§ 371 (c)(1),
(2) Date: Jul. 31, 2017

(87) PCT Pub. No.: WO2016/033212
PCT Pub. Date: Mar. 3, 2016

(65) Prior Publication Data
US 2018/0030116 A1    Feb. 1, 2018

Related U.S. Application Data

(60) Provisional application No. 62/042,574, filed on Aug. 27, 2014.

(51) Int. Cl.
*C07K 14/81* (2006.01)
*A61K 38/00* (2006.01)

(52) U.S. Cl.
CPC .......... *C07K 14/8146* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. |
| 4,301,144 A | 11/1981 | Iwashita et al. |
| 4,399,216 A | 8/1983 | Axel et al. |
| 4,496,689 A | 1/1985 | Mitra |
| 4,640,835 A | 2/1987 | Shimizu et al. |
| 4,670,417 A | 6/1987 | Iwasaki et al. |
| 4,740,461 A | 4/1988 | Kaufman |
| 4,791,192 A | 12/1988 | Nakagawa et al. |
| 4,912,040 A | 3/1990 | Kaufman et al. |
| 4,959,455 A | 9/1990 | Clark et al. |
| 5,011,912 A | 4/1991 | Hopp et al. |
| 6,562,596 B1 | 5/2003 | Silbiger et al. |
| 2003/0143693 A1 | 7/2003 | Silbiger et al. |
| 2003/0195154 A1 | 10/2003 | Walker et al. |
| 2013/0143693 A1 | 6/2013 | Forrest, Sr. |
| 2014/0274874 A1* | 9/2014 | Ketchem ............ C07K 14/8146 514/1.6 |

FOREIGN PATENT DOCUMENTS

| | | |
|---|---|---|
| EP | 0648838 A1 | 4/1995 |
| WO | WO-1987/05330 A1 | 9/1987 |
| WO | WO-1995/05478 A1 | 2/1995 |
| WO | 2004/085617 A2 | 10/2004 |
| WO | WO-2007/016482 A2 | 2/2007 |
| WO | WO-2008/063291 A2 | 5/2008 |
| WO | WO-2014/152012 A2 | 9/2014 |

OTHER PUBLICATIONS

Apte et al., "The gene structure of tissue inhibitor of metalloproteinases (TIMP)-3 and its inhibitory activities define the distinct TIMP gene family", J. Biol. Chem., vol. 270, No. 24, p. 14313-14318 (Jun. 16, 1995).
Fingleton, "MMPs as therapeutic targets—still a viable option?", Semin Cell Dev. Biol., vol. 19, No. 1, pp. 61-68 (Feb. 2008).
Negro et al., "Recombinant human TIMP-3 from *Escherichia coli*: synthesis, refolding, physico-chemical and functional insights", Protein Engineering, vol. 10, No. 5, pp. 593-599 (1997).
Aplin et al., Preparation, properties, and applications of carbohydrate conjugates of proteins and lipids. *CRC Crit. Rev. Biochem.* pp. 259-306 (1981).
Baron et al., Co-regulation of two gene activities by tetracycline via a bidirectional promoter. *Nucleic Acids Res.* 23(17): 3605-6 (1995).
Brueckl et al., Alterations in the tissue inhibitor of metalloproteinase-3 (TIMP-3) are found frequently in human colorectal tumours displaying either microsatellite stability (MSS) or instability (MSI). *Cancer Lett.* 223(1): 137-42 (2005).
Dumelin et al., A portable albumin binder from a DNA-endoded chemical library. *Angew. Chem. Int. Ed. Engl.* 47: 3196-201 (2008).
Duskin et al., Relationship of the structure and biological activity of the natural homologues of tunicamycin. *J. Biol. Chem.* 257: 3105-9 (1982).
Edge et al., Deglycosylation of glycoproteins by trifluoromethanesulfonic acid. *Anal. Biochem.* 118: 131-7(1981).
Gluzman et al., SV40-transformed simian cells support the replication of early SV40 mutants. *Cell*, 23: 175-82(1981).
Hakimuddin et al., A chemical method for the deglycosyalation of proteins. *Arch. Biochem. Biophys.* 259: 52-7(1987).

(Continued)

*Primary Examiner* — James H Alstrum-Acevedo
*Assistant Examiner* — Tara L Martinez
(74) *Attorney, Agent, or Firm* — Julie J. Hong

(57) ABSTRACT

The application concerns tissue inhibitor of metalloproteinase 3 (TIMP-3) muteins, variants and derivatives, nucleic acids encoding them, and methods of making and using them; in particular, muteins of TIMP-3 with specific amino acid substitutions in order to introduce N-linked glycosylation sites.

27 Claims, 12 Drawing Sheets
Specification includes a Sequence Listing.

(56) References Cited

OTHER PUBLICATIONS

Hopp et al., A short polypeptide marker sequence useful for recombinant protein identification and purification. *Nat. Biotechnol.* 6: 1204-10 (1988).

Langton et al., Localization of the functional domains of human tissue inhibitor of metalloproteinases-3 and the effects of Sorsby's fundus dystrophy mutation. *J. Biol. Chem.* 273(27): 16778-81 (1998).

Liu et al., Enhancing the secretion of recombinant proteins by engineering N-glycosylation sites. *Biotech. Prog.* 25(5): 1468-75 (2009).

McMahan et al., A novel IL-1 receptor, cloned from B cells by mammalian expression, is expressed in many cell types. *EMBO J.* 10: 2821-32 (1991).

Rasmussen et al., Isolation, characterization and recombinant protein expression in Veggie-CHO: A serum-free CHO host cell line. *Cytotechnology*, 28: 31-42 (1998).

Rothenfluh et al., Biofunctional polymer nanoparticles for intraarticular targeting and retention in cartilage. *Nat. Mater.* 7(3): 248-54 (2008).

Silbiger et al., Cloning of cDNAs encoding human TIMP-3, a novel member of the tissue inhibitor of metalloproteinase family. *Gene*, 141(2): 293-7 (1994).

Thornton et al., Prediction of progress at last. *Nature*, 354: 105-6 (1991).

Thotakura et al., Enzymatic deglycosylation of glycoproteins. *Meth. Enzymol.* 138: 350-9 (1987).

Urlaub et al., Isolation of Chinese hamster cell mutants deficient in dihydrofolate reductase activity. *Proc. Natl. Acad. Sci. USA* 77:4216-20 (1980).

Wigler et al., Transformation of mammalian cells with genes from procaryotes and eucaryotes. *Cell*, 16(4): 777-85 (1979).

Wisniewska et al., Structural determinants of the ADAM inhibition by TIMP-3: crystal structure of the TACE-N-TIMP-3 complex. *J. Mol. Biol.* 381(5): 1307-19 (2008).

International Preliminary Report on Patentability issued in connection with International Application No. PCT/US2015/046992, dated Feb. 28, 2017.

* cited by examiner 1. 100 ng huFc STD
2. 250 ng huFc STD
3. 500 ng huFc STD
4. 1000 ng huFc STD
5. CHO-K1 endogenous control
6. N-TIMP-HSA pool 1 w/Heparin
7. N-TIMP-HSA pool 2 w/Heparin
8. N-TIMP-HSA pool 3 w/Heparin
9. N-TIMP-HSA pool 1 wo/Heparin
10. N-TIMP-HSA pool 2 wo/Heparin
11. N-TIMP-HSA pool 3 wo/Heparin

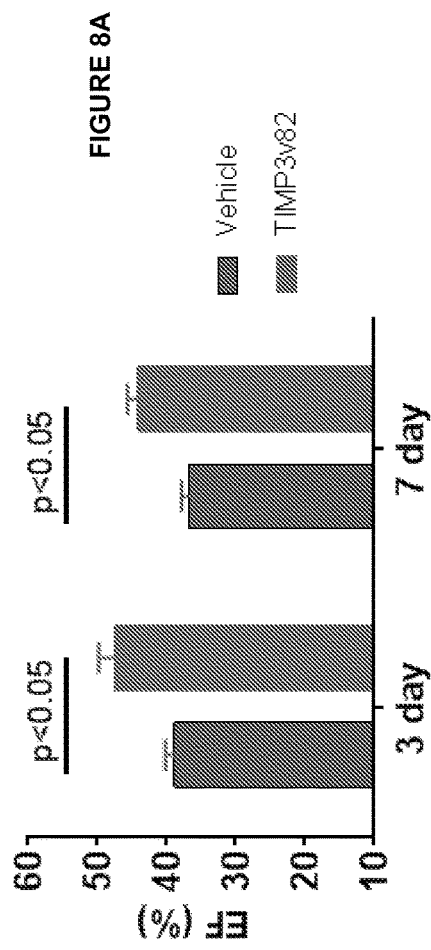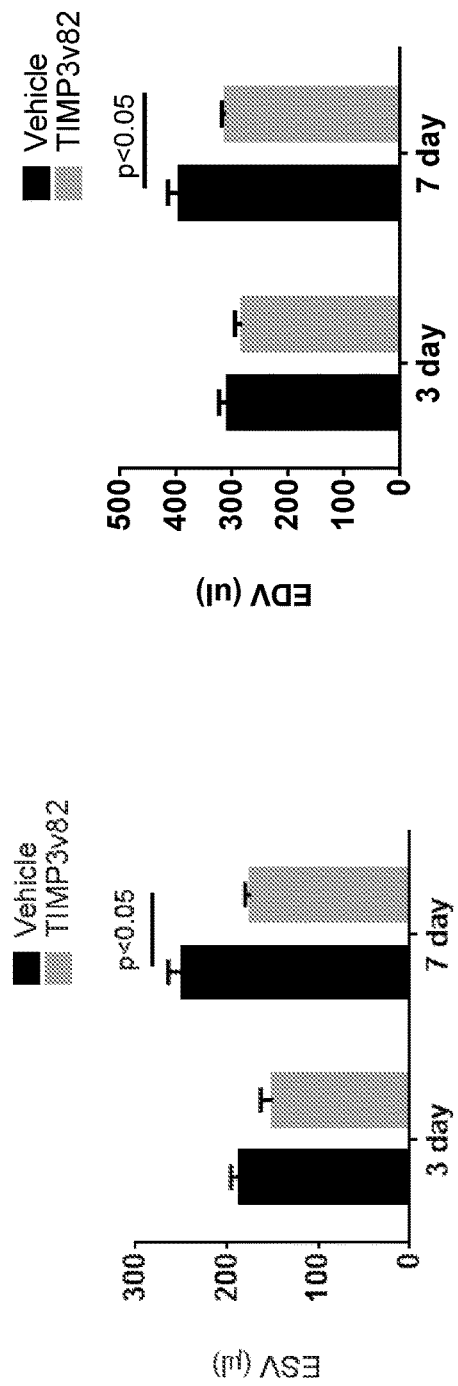
FIGURE 8A
FIGURE 8B
FIGURE 8C

SEQ ID NO:1 native huTIMP3 cDNA
```
atgacccctt ggctcgggct catcgtgctc ctgggcagct ggagcctggg ggactggggc    60
gccgaggcgt gcacatgctc gcccagccac ccccaggacg ccttctgcaa ctccgacatc   120
gtgatccggg ccaaggtggt ggggaagaag ctggtaaagg aggggcccct cggcacgctg   180
gtctacacca tcaagcagat gaagatgtac cgaggcttca ccaagatgcc ccatgtgcag   240
tacatccaca cggaagcttc cgagagtctc tgtggcctta agctggaggt caacaagtac   300
cagtacctgc tgacaggtcg cgtctatgat ggcaagatgt acacggggct gtgcaacttc   360
gtggagaggt gggaccagct caccctctcc cagcgcaagg ggctgaacta tcggtatcac   420
ctgggttgta actgcaagat caagtcctgc tactacctgc cttgctttgt gacttccaag   480
aacgagtgtc tctggaccga catgctctcc aatttcggtt accctggcta ccagtccaaa   540
cactacgcct gcatccggca gaagggcggc tactgcagct ggtaccgagg atgggccccc   600
ccggataaaa gcatcatcaa tgccacagac ccc                                633
```

SEQ ID NO:2 native huTIMP3 amino acid
MTPWLGLIVLLGSWSLGDWGAEACTCSPSHPQDAFCNSDIVIRAKVVGKKLVKEGPFGTLVYTIKQMKMYRGFT
KMPHVQYIHTEASESLCGLKLEVNKYQYLLTGRVYDGKMYTGLCNFVERWDQLTLSQRKGLNYRYHLGCNCKIK
SCYYLPCFVTSKNECLWTDMLSNFGYPGYQSKHYACIRQKGGYCSWYRGWAPPDKSIINATDP SEQ ID NO:3 huTIMP3(K45N, V47T, P56N, G58T, Q126N, R138T)
XXXXXXXXXXXXXXXXXXXXXXXXXCTCSPSHPQDAFCNSDIVIRANVTGKKLVKEGNFTTLVYTIKQMKMYRGFT
KMPHVQYIHTEASESLCGLKLEVNKYQYLLTGRVYDGKMYTGLCNFVERWDNLTLSQRKGLNYTYHLGCNCKIK
SCYYLPCFVTSKNECLWTDMLSNFGYPGYQSKHYACIRQKGGYCSWYRGWAPPDKSIINATDP SEQ ID NO:4 huTIMP3(K45N, V47T, P56N, G58T, K94N, E96T, R138T)
XXXXXXXXXXXXXXXXXXXXXXXXXCTCSPSHPQDAFCNSDIVIRANVTGKKLVKEGNFTTLVYTIKQMKMYRGFT
KMPHVQYIHTEASESLCGLNLTVNKYQYLLTGRVYDGKMYTGLCNFVERWDQLTLSQRKGLNYTYHLGCNCKIK
SCYYLPCFVTSKNECLWTDMLSNFGYPGYQSKHYACIRQKGGYCSWYRGWAPPDKSIINATDP SEQ ID NO:5 huTIMP3(K45N, V47T, P56N, G58T, R138T, G173T)
XXXXXXXXXXXXXXXXXXXXXXXXXCTCSPSHPQDAFCNSDIVIRANVTGKKLVKEGNFTTLVYTIKQMKMYRGFT
KMPHVQYIHTEASESLCGLKLEVNKYQYLLTGRVYDGKMYTGLCNFVERWDQLTLSQRKGLNYTYHLGCNCKIK
SCYYLPCFVTSKNECLWTDMLSNFTYPGYQSKHYACIRQKGGYCSWYRGWAPPDKSIINATDP SEQ ID NO:6 huTIMP3(K45N, V47T, F57N, K94N, E96T, D110N, K112T)
XXXXXXXXXXXXXXXXXXXXXXXXXCTCSPSHPQDAFCNSDIVIRANVTGKKLVKEGPNGTLVYTIKQMKMYRGFT
KMPHVQYIHTEASESLCGLNLTVNKYQYLLTGRVYNGTMYTGLCNFVERWDQLTLSQRKGLNYRYHLGCNCKIK
SCYYLPCFVTSKNECLWTDMLSNFGYPGYQSKHYACIRQKGGYCSWYRGWAPPDKSIINATDP SEQ ID NO:7 huTIMP3(K45N, V47T, F57N, K94N, E96T, R138T)
XXXXXXXXXXXXXXXXXXXXXXXXXCTCSPSHPQDAFCNSDIVIRANVTGKKLVKEGPNGTLVYTIKQMKMYRGFT
KMPHVQYIHTEASESLCGLNLTVNKYQYLLTGRVYDGKMYTGLCNFVERWDQLTLSQRKGLNYTYHLGCNCKIK
SCYYLPCFVTSKNECLWTDMLSNFGYPGYQSKHYACIRQKGGYCSWYRGWAPPDKSIINATDP SEQ ID NO:8 huTIMP3(K45N, V47T, H78N, Q80T, K94N, E96T, R138T, G173T)
XXXXXXXXXXXXXXXXXXXXXXXXXCTCSPSHPQDAFCNSDIVIRANVTGKKLVKEGPFGTLVYTIKQMKMYRGFT
KMPNVTYIHTEASESLCGLNLTVNKYQYLLTGRVYDGKMYTGLCNFVERWDQLTLSQRKGLNYTYHLGCNCKIK
SCYYLPCFVTSKNECLWTDMLSNFTYPGYQSKHYACIRQKGGYCSWYRGWAPPDKSIINATDP

FIGURE 10A

SEQ ID NO:9 huTIMP3(K45N, V47T, K94N, E96T, D110N, K112T, R138T)
XXXXXXXXXXXXXXXXXXXXXXXXCTCSPSHPQDAFCNSDIVIRANVTGKKLVKEGPFGTLVYTIKQMKMYRGFT
KMPHVQYIHTEASESLCGLNLTVNKYQYLLTGRVYNGTMYTGLCNFVERWDQLTLSQRKGLNYTYHLGCNCKIK
SCYYLPCFVTSKNECLWTDMLSNFGYPGYQSKHYACIRQKGGYCSWYRGWAPPDKSIINATDP

SEQ ID NO:10 huTIMP3(K45N, V47T, K94N, E96T, D110N, K112T, G173T)
XXXXXXXXXXXXXXXXXXXXXXXXCTCSPSHPQDAFCNSDIVIRANVTGKKLVKEGPFGTLVYTIKQMKMYRGFT
KMPHVQYIHTEASESLCGLNLTVNKYQYLLTGRVYNGTMYTGLCNFVERWDQLTLSQRKGLNYRYHLGCNCKIK
SCYYLPCFVTSKNECLWTDMLSNFTYPGYQSKHYACIRQKGGYCSWYRGWAPPDKSIINATDP

SEQ ID NO:11 huTIMP3(K45N, V47T, K94N, E96T, R138T, G173T)
XXXXXXXXXXXXXXXXXXXXXXXXCTCSPSHPQDAFCNSDIVIRANVTGKKLVKEGPFGTLVYTIKQMKMYRGFT
KMPHVQYIHTEASESLCGLNLTVNKYQYLLTGRVYDGKMYTGLCNFVERWDQLTLSQRKGLNYTYHLGCNCKIK
SCYYLPCFVTSKNECLWTDMLSNFTYPGYQSKHYACIRQKGGYCSWYRGWAPPDKSIINATDP

SEQ ID NO:12 huTIMP3(K45S, F57N, K94N, E96T, D110N, K112T, R138T)
XXXXXXXXXXXXXXXXXXXXXXXXCTCSPSHPQDAFCNSDIVIRASVVGKKLVKEGPNGTLVYTIKQMKMYRGFT
KMPHVQYIHTEASESLCGLNLTVNKYQYLLTGRVYNGTMYTGLCNFVERWDQLTLSQRKGLNYTYHLGCNCKIK
SCYYLPCFVTSKNECLWTDMLSNFGYPGYQSKHYACIRQKGGYCSWYRGWAPPDKSIINATDP

SEQ ID NO:13 huTIMP3(K45S, F57N, H78N, Q80T, K94N, E96T, R138T)
XXXXXXXXXXXXXXXXXXXXXXXXCTCSPSHPQDAFCNSDIVIRASVVGKKLVKEGPNGTLVYTIKQMKMYRGFT
KMPNVTYIHTEASESLCGLNLTVNKYQYLLTGRVYDGKMYTGLCNFVERWDQLTLSQRKGLNYTYHLGCNCKIK
SCYYLPCFVTSKNECLWTDMLSNFGYPGYQSKHYACIRQKGGYCSWYRGWAPPDKSIINATDP

SEQ ID NO:14 huTIMP3(K50N, V52T P56N, G58T, K94N, E96T, D110N, K112T, R138T)
XXXXXXXXXXXXXXXXXXXXXXXXCTCSPSHPQDAFCNSDIVIRAKVVGKNLTKEGNFTTLVYTIKQMKMYRGFT
KMPHVQYIHTEASESLCGLNLTVNKYQYLLTGRVYNGTMYTGLCNFVERWDQLTLSQRKGLNYTYHLGCNCKIK
SCYYLPCFVTSKNECLWTDMLSNFGYPGYQSKHYACIRQKGGYCSWYRGWAPPDKSIINATDP

SEQ ID NO:15 huTIMP3(K50N, V52T, H78N, Q80T, K94N, E96T, R138T, G173T)
XXXXXXXXXXXXXXXXXXXXXXXXCTCSPSHPQDAFCNSDIVIRAKVVGKNLTKEGPFGTLVYTIKQMKMYRGFT
KMPNVTYIHTEASESLCGLNLTVNKYQYLLTGRVYDGKMYTGLCNFVERWDQLTLSQRKGLNYTYHLGCNCKIK
SCYYLPCFVTSKNECLWTDMLSNFTYPGYQSKHYACIRQKGGYCSWYRGWAPPDKSIINATDP

SEQ ID NO:16 huTIMP3(K50N, V52T, K94N, E96T, D110N, K112T, R138T)
XXXXXXXXXXXXXXXXXXXXXXXXCTCSPSHPQDAFCNSDIVIRAKVVGKNLTKEGPFGTLVYTIKQMKMYRGFT
KMPHVQYIHTEASESLCGLNLTVNKYQYLLTGRVYNGTMYTGLCNFVERWDQLTLSQRKGLNYTYHLGCNCKIK
SCYYLPCFVTSKNECLWTDMLSNFGYPGYQSKHYACIRQKGGYCSWYRGWAPPDKSIINATDP

SEQ ID NO:17 huTIMP3(K50N, V52T, K94N, E96T, D110N, K112T, R138T, G173T)
XXXXXXXXXXXXXXXXXXXXXXXXCTCSPSHPQDAFCNSDIVIRAKVVGKNLTKEGPFGTLVYTIKQMKMYRGFT
KMPHVQYIHTEASESLCGLNLTVNKYQYLLTGRVYNGTMYTGLCNFVERWDQLTLSQRKGLNYTYHLGCNCKIK
SCYYLPCFVTSKNECLWTDMLSNFTYPGYQSKHYACIRQKGGYCSWYRGWAPPDKSIINATDP

FIGURE 10B

SEQ ID NO:18 huTIMP3(K50N, V52T, K94N, E96T, R138T, G173T)
XXXXXXXXXXXXXXXXXXXXXXXXCTCSPSHPQDAFCNSDIVIRAKVVGKNLTKEGPFGTLVYTIKQMKMYRGFT
KMPHVQYIHTEASESLCGLNLTVNKYQYLLTGRVYDGKMYTGLCNFVERWDQLTLSQRKGLNYTYHLGCNCKIK
SCYYLPCFVTSKNECLWTDMLSNFTYPGYQSKHYACIRQKGGYCSWYRGWAPPDKSIINATDP

SEQ ID NO:19 huTIMP3(K50N, V52T, Q126N, R138T, G173T)
XXXXXXXXXXXXXXXXXXXXXXXXCTCSPSHPQDAFCNSDIVIRAKVVGKNLTKEGPFGTLVYTIKQMKMYRGFT
KMPHVQYIHTEASESLCGLKLEVNKYQYLLTGRVYDGKMYTGLCNFVERWDNLTLSQRKGLNYTYHLGCNCKIK
SCYYLPCFVTSKNECLWTDMLSNFTYPGYQSKHYACIRQKGGYCSWYRGWAPPDKSIINATDP

SEQ ID NO:20 huTIMP3(P56N, G58T, H78N, Q80T, K94N, E96T, R138T)
XXXXXXXXXXXXXXXXXXXXXXXXCTCSPSHPQDAFCNSDIVIRAKVVGKKLVKEGNFTTLVYTIKQMKMYRGFT
KMPNVTYIHTEASESLCGLNLTVNKYQYLLTGRVYDGKMYTGLCNFVERWDQLTLSQRKGLNYTYHLGCNCKIK
SCYYLPCFVTSKNECLWTDMLSNFGYPGYQSKHYACIRQKGGYCSWYRGWAPPDKSIINATDP

SEQ ID NO:21 huTIMP3(P56N, G58T K94N, E96T, Q126N, R138T)
XXXXXXXXXXXXXXXXXXXXXXXXCTCSPSHPQDAFCNSDIVIRAKVVGKKLVKEGNFTTLVYTIKQMKMYRGFT
KMPHVQYIHTEASESLCGLNLTVNKYQYLLTGRVYDGKMYTGLCNFVERWDNLTLSQRKGLNYTYHLGCNCKIK
SCYYLPCFVTSKNECLWTDMLSNFGYPGYQSKHYACIRQKGGYCSWYRGWAPPDKSIINATDP

SEQ ID NO:22 huTIMP3(P56N, G58T, K94N, E96T, D110N, K112T, R138T)
XXXXXXXXXXXXXXXXXXXXXXXXCTCSPSHPQDAFCNSDIVIRAKVVGKKLVKEGNFTTLVYTIKQMKMYRGFT
KMPHVQYIHTEASESLCGLNLTVNKYQYLLTGRVYNGTMYTGLCNFVERWDQLTLSQRKGLNYTYHLGCNCKIK
SCYYLPCFVTSKNECLWTDMLSNFGYPGYQSKHYACIRQKGGYCSWYRGWAPPDKSIINATDP

SEQ ID NO:23 huTIMP3(P56N, G58T, H78N, Q80T, K94N, E96T, G173T)
XXXXXXXXXXXXXXXXXXXXXXXXCTCSPSHPQDAFCNSDIVIRAKVVGKKLVKEGNFTTLVYTIKQMKMYRGFT
KMPNVTYIHTEASESLCGLNLTVNKYQYLLTGRVYDGKMYTGLCNFVERWDQLTLSQRKGLNYRYHLGCNCKIK
SCYYLPCFVTSKNECLWTDMLSNFTYPGYQSKHYACIRQKGGYCSWYRGWAPPDKSIINATDP

SEQ ID NO:24 huTIMP3(P56N, G58T, Q126N, R138T, G173T)
XXXXXXXXXXXXXXXXXXXXXXXXCTCSPSHPQDAFCNSDIVIRAKVVGKKLVKEGNFTTLVYTIKQMKMYRGFT
KMPHVQYIHTEASESLCGLKLEVNKYQYLLTGRVYDGKMYTGLCNFVERWDNLTLSQRKGLNYTYHLGCNCKIK
SCYYLPCFVTSKNECLWTDMLSNFTYPGYQSKHYACIRQKGGYCSWYRGWAPPDKSIINATDP

SEQ ID NO:25 huTIMP3(H78N, Q80T, K94N, E96T, R138T, G173T)
XXXXXXXXXXXXXXXXXXXXXXXXCTCSPSHPQDAFCNSDIVIRAKVVGKKLVKEGPFGTLVYTIKQMKMYRGFT
KMPNVTYIHTEASESLCGLNLTVNKYQYLLTGRVYDGKMYTGLCNFVERWDQLTLSQRKGLNYTYHLGCNCKIK
SCYYLPCFVTSKNECLWTDMLSNFTYPGYQSKHYACIRQKGGYCSWYRGWAPPDKSIINATDP

SEQ ID NO:26 huTIMP3(H78N, Q80T, K94N, E96T, D110N, K112T, R138T)
XXXXXXXXXXXXXXXXXXXXXXXXCTCSPSHPQDAFCNSDIVIRAKVVGKKLVKEGPFGTLVYTIKQMKMYRGFT
KMPNVTYIHTEASESLCGLNLTVNKYQYLLTGRVYNGTMYTGLCNFVERWDQLTLSQRKGLNYTYHLGCNCKIK
SCYYLPCFVTSKNECLWTDMLSNFGYPGYQSKHYACIRQKGGYCSWYRGWAPPDKSIINATDP

FIGURE 10C

VARIANTS OF TISSUE INHIBITOR OR METALLOPROTIENASE TYPE THREE (TIMP-3), COMPOSITIONS AND METHODS

CROSS-REFERENCE TO RELATED APPLICATION AND INCORPORATION BY REFERENCE

This application claims the benefit of priority to 62/042,574 filed Aug. 27, 2014, which is hereby incorporated by reference.

Incorporated by reference in its entirety is a computer-readable nucleotide/amino acid sequence listing submitted concurrently herewith and identified as follows: ASCII text file named "49907 SubSeqListing.txt," 168,878 bytes, created Dec. 9, 2019.

FIELD OF THE INVENTION

The present invention relates in general to metalloproteinase inhibitors. In particular, the invention relates to tissue inhibitor of metalloproteinase 3 ("TIMP-3") and novel, useful variants, muteins and derivatives thereof.

BACKGROUND OF THE INVENTION

Connective tissues and articular cartilage are maintained in dynamic equilibrium by the opposing effects of extracellular matrix synthesis and degradation. Degradation of the matrix is brought about primarily by the enzymatic action of metalloproteinases, including matrix metalloproteinases (MMPs) and disintegrin-metalloproteinases with thrombospondin motifs (ADAMTSs). While these enzymes are important in many natural processes (including development, morphogenesis, bone remodeling, wound healing and angiogenesis), disregulation of these enzymes leading to their elevated levels are believed to play a detrimental role in degradative diseases of connective tissue, including rheumatoid arthritis and osteoarthritis, as well as in cancer and cardiovascular conditions.

Endogenous inhibitors of metalloproteinases include plasma alpha2-macroglobulin and tissue inhibitors of metalloproteinases (TIMPs), of which there are four known to be encoded in the human genome. TIMP-3 inhibits all the major cartilage-degrading metalloproteases, and multiple lines of evidence indicate that it protects cartilage. Addition of the protein to cartilage-explants prevents cytokine-induced degradation, and intra-articular injection reduces cartilage damage in the rat medial meniscal tear model of osteoarthritis.

Dysregulation of MMPs also occurs in congestive heart failure and is thought to play a role in numerous proinflammatory processes. However, development of TIMP-3 as a therapeutic inhibitor of MMP activity has been hampered by challenges in production of recombinant protein and short half-life of recombinant forms of TIMP-3. In particular, the serum half-life of TIMP-3 following intravenous administration in rats is less than sixty minutes, and such a short residence time negatively impacts the ability to maintain a therapeutically useful concentration at a disease site. Accordingly, there is a need in the art for forms of TIMP-3 that exhibit favorable production, purification and pharmacokinetic/pharmacodynamic properties.

SUMMARY OF THE INVENTION

The invention provides TIMP-3 polypeptides having advantageous properties, e.g., enhanced pharmacokinetic or pharmacodynamics properties (such as half-life), improved expression levels compared to native TIMP-3, reduced affinity to non-targets (e.g., scavenger receptors), and/or reduced dependence on heparin for production.

In some embodiments, the invention provides a TIMP-3 polypeptide fused to one or more half-life extending moieties or chemically modified with one or more half-life extending moieties. For example, in some aspects, the invention provides a fusion protein comprising TIMP-3 (or a fragment thereof) fused to the Fc domain of an isolated antibody at the N- or C-terminus of TIMP-3. The Fc domain may be fused to TIMP-3 (or a fragment thereof) via the N- or C-terminus of the Fc moiety. The Fc domain may be monomeric or heterodimeric. The invention also contemplates a TIMP-3 polypeptide (or a fragment thereof) fused to human serum albumin or a full antibody (at the N- or C-terminus of the heavy chain or light chain). In some aspects, the chemical modification to TIMP-3 (or a fragment thereof) to extend half-life includes conjugation to polyethylene glycol (PEG).

In certain embodiments, the TIMP-3 protein carries mutations in the native sequence resulting in improved half-life; such TIMP-3 mutations are described herein as, e.g., "TIMP-3 muteins." In various aspects, the TIMP-3 protein is at least 90% identical in amino acid sequence to the mature region of TIMP-3 set forth in SEQ ID NO:2, wherein the mutein has at least one mutation that introduces at least one N-linked glycosylation site. In an additional embodiment, the TIMP-3 mutein has two, three, or four new N-linked glycosylation sites; in a still further embodiment, the number of N-linked glycosylation sites introduced is five, six, seven, eight, nine, ten, eleven or twelve. In each mutein, it is further contemplated that addition of one or more new N-linked glycosylation cites does not substantially diminish the metalloproteinase inhibitory activity of the native molecule.

Also embodied within the invention is a TIMP-3 mutein having a mature region that is at least 90% identical in amino acid sequence to the mature region of TIMP-3 set forth in SEQ ID NO:2, having at least one mutation, the mutation being selected from the group consisting of K45N, V47T, K50N, V52T, P56N, F57N, G58T, H78N, Q80T, K94N, E96T, D110N, K112T, R138T, and G173T. Additional embodiments include a TIMP-3 mutein having two or more pairs of mutations selected from the group consisting of K45N/V47T, K50N/V52T, P56N/G58T, H78N/Q80T, K94N/E96T, and D110N/K112T; and a TIMP-3 mutein having one or more pairs of mutations selected from the group consisting of K45N/V47T, K50N/V52T, P56N/G58T, H78N/Q80T, K94N/E96T, and D110N/K112T, and an additional mutation that is selected from the group consisting of R138T, G173T, and both R138T and G173T. Further embodiments include muteins having any of the aforementioned combinations of mutation and in addition the mutation F57N.

In one embodiment of the invention, at least one N-linked glycosylation site is introduced in a region of the TIMP-3 amino acid sequence selected from the group consisting of: the region consisting of amino acids 44-59; the region consisting of amino acids 77-81; the region consisting of amino acids 93-97; the region consisting of amino acids 109-112; the region consisting of amino acids 137-139; the region consisting of amino acids 172-174; and combinations thereof. In an additional embodiment, the TIMP-3 mutein has two, three, four, or five N-linked glycosylation sites; in a still further embodiment, the number of N-linked glycosylation sites introduced is four, five, six, seven, eight, nine, ten, eleven or twelve.

One embodiment of the invention provides TIMP-3 muteins K45N, V47T, P56N, G58T, Q126N, R138T (SEQ ID NO:3); K45N, V47T, P56N, G58T, K94N, E96T, R138T (SEQ ID NO:4); K45N, V47T, P56N, G58T, R138T, G173T (SEQ ID NO:5); K45N, V47T, F57N, K94N, E96T, D110N, K112T (SEQ ID NO:6); K45N, V47T, F57N, K94N, E96T, R138T (SEQ ID NO:7); K45N, V47T, H78N, Q80T, K94N, E96T, R138T, G173T (SEQ ID NO:8); K45N, V47T, K94N, E96T, D110N, K112T, R138T (SEQ ID NO:9); K45N, V47T, K94N, E96T, D110N, K112T, G173T (SEQ ID NO:10); K45N, V47T, K94N, E96T, R138T, G173T (SEQ ID NO:11); K45S, F57N, K94N, E96T, D110N, K112T, R138T (SEQ ID NO:12); K45S, F57N, H78N, Q80T, K94N, E96T, R138T (SEQ ID NO:13); K50N, V52T P56N, G58T, K94N, E96T, D110N, K112T, R138T (SEQ ID NO:14); K50N, V52T, H78N, Q80T, K94N, E96T, R138T, G173T (SEQ ID NO:15); K50N, V52T, K94N, E96T, D110N, K112T, R138T (SEQ ID NO:16); K50N, V52T, K94N, E96T, D110N, K112T, R138T, G173T (SEQ ID NO:17); K50N, V52T, K94N, E96T, R138T, G173T (SEQ ID NO:18); K50N, V52T, Q126N, R138T, G173T (SEQ ID NO:19); P56N, G58T, H78N, Q80T, K94N, E96T, R138T (SEQ ID NO:20); P56N, G58T K94N, E96T, Q126N, R138T (SEQ ID NO:21); P56N, G58T, K94N, E96T, D110N, K112T, R138T (SEQ ID NO:22); P56N, G58T, H78N, Q80T, K94N, E96T, G173T (SEQ ID NO:23); P56N, G58T, Q126N, R138T, G173T (SEQ ID NO:24); H78N, Q80T, K94N, E96T, R138T, G173T (SEQ ID NO:25); and H78N, Q80T, K94N, E96T, D110N, K112T, R138T (SEQ ID NO:26).

Further embodiments include TIMP-3 muteins K50N/V52T,D110N/K112T, R138T, G173T; K45N/V47T, D110N/K112T, R138T, G173T; H78N/Q80T, D110N/K112T, R138T, G173T; K45N/V47T, K50N/V52T, H78N/A80T, R138T; K45N/V47T, H78N/Q80T, D110N/K112T, G173T; K45N/V47T, H78N/Q80T, R138T, G173T; K50N/V52T, H78N/Q80T, K94N/E96T, G173T; K50N/V52T, H78N/Q80T, D110N/K112T, R138T; K45N/V47T, K50N/V52T, H78N/Q80T, D110N/K112T; K50N/V52T, H78N/Q80T, R138T, G173T; K45N/V47T, H78N/Q80T, R138T, G173T; K45N/V47T, H78N/Q80T, D110N/K112T, R138T; K45N/V47T, K50N/V52T, H78N/Q80T, D110N/K112T, G173T; K45N/V47T, K50N/V52T, H78N/Q80T, R138T, G173T; K45N/V47T, K50N/V52T, H78N/Q80T, K94N/E96T, G173T; K45N/V47T, H78N/Q80T, K94N/E96T, R138T, G173T; K50N/V52T, H78N/Q80T, K94N/E96T, R138T, G173T; K45N/V47T, H78N/Q80T, D110N/K112T, R138T, G173T; K50N/V52T, H78N/Q80T, D110N/K112T, R138T, G173T; and K45N/V52T, K50N/V52T, H78N/Q80T, D110N/K112T, R138T.

The invention further provides a TIMP-3 mutein comprising (or consisting of) the amino acid sequence set forth in SEQ ID NOs: 3-26 and 51-60, as well as a nucleic acid comprising nucleotide sequence encoding the amino acid sequence of any one of SEQ ID NOs: 3-26 and 51-60.

In one aspect, the invention provides a nucleic acid (e.g., an isolated nucleic acid) that encodes a TIMP-3 mutein according to any one of the aforementioned TIMP-3 muteins. Other aspects of the invention are an expression vector comprising the nucleic acid; a host cell (e.g., an isolated host cell) transformed or transfected with the expression vector; and a method of producing a recombinant TIMP-3 mutein comprising culturing the transformed or transfected host cell of under conditions promoting expression of the TIMP-3 mutein, and recovering the TIMP-3 mutein.

The invention also provides a nucleic acid comprising (or consisting of) the nucleic acid sequence set forth in SEQ ID NOs: 27-50 and 61-70.

Further provided is a composition comprising the TIMP-3 mutein described herein, as well as a method of treating a condition in which matrix metalloproteases (MMPs) and/or other proteinases that are inhibited or inhibitable by TIMP-3 play a causative or exacerbating role, comprising administering to an individual afflicted with such a condition, an amount of such composition sufficient to treat the condition.

In one embodiment, the condition is selected from the group consisting of inflammatory conditions, osteoarthritis, acute myocardial infarction, cardiac ischemia (including myocardial ischemia), reperfusion injury, and progression to chronic heart failure (e.g., congestive heart failure). In various aspects, the condition is vascular plaque stabilization, vasculopathy, or neointima formation. In another embodiment, the condition is selected from the group consisting of acute lung injury, acute respiratory distress syndrome, asthma, chronic obstructive pulmonary disease (COPD), and idiopathic pulmonary fibrosis (IPF), inflammatory bowel disease (for example, ulcerative colitis, Crohn's disease, and celiac disease), psoriasis, myocarditis including viral myocarditis, inflammation related to atherosclerosis, and arthritic conditions including rheumatoid arthritis and psoriatic arthritis.

In a further embodiment, the condition is selected from the group consisting of dystrophic epidermolysis bullosa, osteoarthritis, pseudogout, rheumatoid arthritis including juvenile rheumatoid arthritis, ankylosing spondylitis, scleroderma, periodontal disease, ulceration including corneal, epidermal, or gastric ulceration, wound healing after surgery, restenosis, emphysema, Paget's disease of bone, osteoporosis, scleroderma, pressure atrophy of bone or tissues as in bedsores, cholesteatoma, abnormal wound healing, rheumatoid arthritis, pauciarticular rheumatoid arthritis, polyarticular rheumatoid arthritis, systemic onset rheumatoid arthritis, ankylosing spondylitis, enteropathic arthritis, reactive arthritis, SEA Syndrome (Seronegativity, Enthesopathy, Arthropathy Syndrome), dermatomyositis, psoriatic arthritis, scleroderma, systemic lupus erythematosus, vasculitis, myolitis, polymyolitis, dermatomyolitis, osteoarthritis, polyarteritis nodossa, Wegener's granulomatosis, arteritis, polymyalgia rheumatica, sarcoidosis, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease, ulcerative colitis, Crohn's disease, Celiac disease (nontropical Sprue), enteropathy associated with seronegative arthropathies, microscopic or collagenous colitis, eosinophilic gastroenteritis, or pouchitis resulting after proctocolectomy and ileoanal anastomosis, pancreatitis, insulin-dependent diabetes mellitus, mastitis, cholecystitis, cholangitis, pericholangitis, multiple sclerosis (MS), asthma (including extrinsic and intrinsic asthma as well as related chronic inflammatory conditions, or hyperresponsiveness, of the airways), chronic obstructive pulmonary disease (COPD. i.e., chronic bronchitis, emphysema), Acute Respiratory Disorder Syndrome (ARDS), respiratory distress syndrome, cystic fibrosis, pulmonary hypertension, pulmonary vasoconstriction, acute lung injury, allergic bronchopulmonary aspergillosis, hypersensitivity pneumonia, eosinophilic pneumonia, bronchitis, allergic bronchitis bronchiectasis, tuberculosis, hypersensitivity pneumonitis, occupational asthma, asthma-like disorders, sarcoid, reactive airway disease (or dysfunction) syndrome, byssinosis, interstitial lung disease, hyper-eosinophilic syndrome, rhinitis, sinusitis, and parasitic lung disease, airway hyperresponsiveness associated with viral-induced conditions (for example, respiratory syncytial virus (RSV), parainfluenza virus (PIV), rhinovirus (RV) and adenovirus), Guillain-Barre disease, Graves' disease, Addison's disease, Raynaud's phenomenon, autoimmune hepatitis, graft versus host disease (GVHD), cerebral ischemia, traumatic brain injury, multiple sclerosis, neuropathy, myopathy, spinal cord injury, and amyotrophic lateral sclerosis (ALS).

DESCRIPTION OF THE FIGURES

FIGS. 8A-8C are bar graphs illustrating improved cardiac function and reduced cardiac remodeling mediated by TIMP-3 [H78N, Q80T, K94N, E96T, D110N, K112T, R138T] (SEQ ID NO:26) (referred to as "TIMP3v82" in figure) following myocardial infarction in rats. FIG. 8A illustrates ejection fraction (% EF, y-axis) detected on day 3 and day 7 (x-axis) following administration for subjects treated with vehicle (bar on the left) or TIMP-3 [H78N, Q80T, K94N, E96T, D110N, K112T, R138T] (bar on the right). FIG. 8B illustrates end systolic volume (ESV) (y-axis) measured on day 3 and day 7 (x-axis) following administration of vehicle or TIMP-3 [H78N, Q80T, K94N, E96T, D110N, K112T, R138T]. FIG. 8C illustrates end diastolic volume (ESV) (y-axis) measured on day 3 and day 7 (x-axis) following administration of vehicle or TIMP-3 [H78N, Q80T, K94N, E96T, D110N, K112T, R138T].

FIGS. 10A-10C provide amino acid sequences of TIMP-3 muteins. The series of "X"s included in amino acid sequences denotes the position of the signal peptide (e.g., amino acids 1-23 of SEQ ID NO: 2).

DETAILED DESCRIPTION OF THE INVENTION

Figure 1:
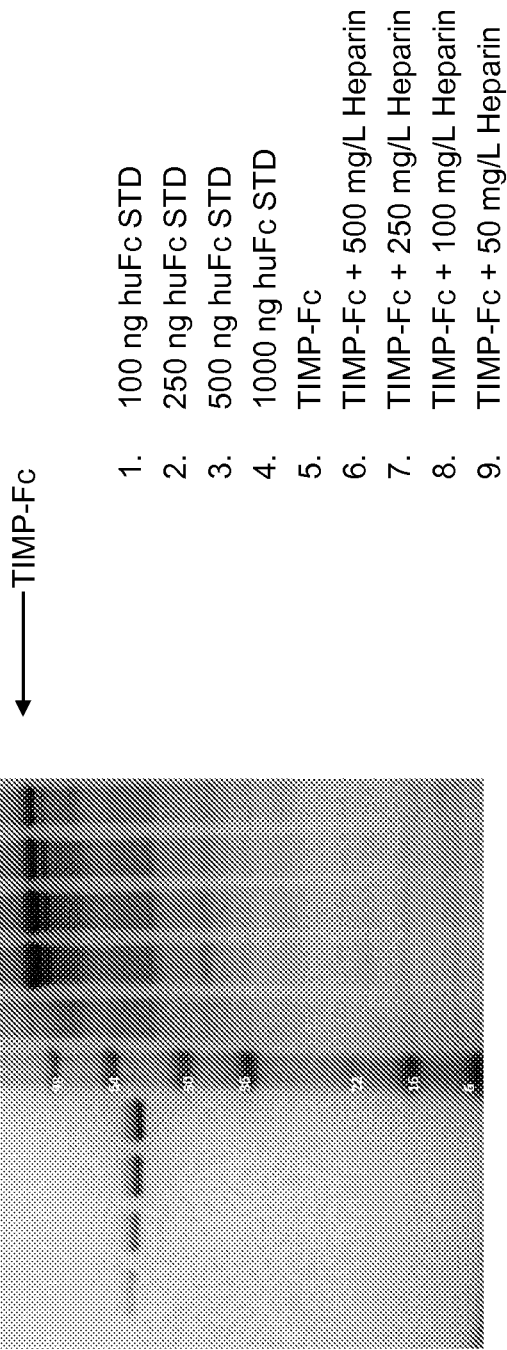
FIG. 1 is a reproduction of an SDS-PAGE gel illustrating the amount of a TIMP-3 fusion protein, N-TIMP-3 (AA 1-144) fused to Fc portion of an antibody ("TIMP-3-Fc"), produced in the presence of varying amounts of heparin. Lane #1-4 contained Fc standards ("STD"): Lane #1 contained 100 ng human Fc; Lane #2 contained 250 ng human Fc; Lane #3 contained 500 ng human Fc; and Lane #4 contained 1000 ng human Fc. Lanes #5-9 contained 10 µL samples from culture media from CHOK1 cells expressing TIMP-3-Fc grown in the absence of heparin (Lane #5), in the presence of 500 mg/L heparin (Lane #6), in the presence of 250 mg/L heparin (Lane #7), in the presence of 100 mg/L heparin (Lane #8), or in the presence of 50 mg/L heparin (Lane #9).

The invention provides compositions, kits, and methods relating to TIMP-3 polypeptides, variants, derivatives or muteins. Also provided are nucleic acids, and derivatives and fragments thereof, comprising a sequence of nucleotides that encodes all or a portion of such a TIMP-3 polypeptide, variant, derivative or mutein, e.g., a nucleic acid encoding all or part of such TIMP-3 polypeptides, variants, derivatives or muteins; plasmids and vectors comprising such nucleic acids, and cells or cell lines comprising such nucleic acids and/or vectors and plasmids. The provided methods include, for example, methods of making, identifying, or isolating TIMP-3 polypeptides, variants, derivatives or muteins that exhibit desirable properties.

Numerous conditions exist in which it would be advantageous to augment endogenous TIMP-3 in a mammal, or to increase the level of TIMP-3 in a particular tissue. Accordingly, also provided herein are methods of making compositions, such as pharmaceutical compositions, comprising a TIMP-3 polypeptide, variant, derivative or mutein, and methods for administering a composition comprising a TIMP-3 polypeptide, variant, derivative or mutein to a subject, for example, a subject afflicted with a condition in which dysregulation of matrix metalloproteinase activity results in excessive or inappropriate remodeling of tissue.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well-known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings:

The term "isolated" as used to characterize a molecule (where the molecule is, for example, a polypeptide, a polynucleotide, or an antibody) indicates that the molecule by virtue of its origin or source of derivation (1) is not associated with naturally associated components that accompany it in its native state, (2) is substantially free of other molecules from the same species (3) is expressed by a cell from a different species, or (4) does not occur in nature without human intervention. Thus, a molecule that is chemically synthesized, or synthesized in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification. In various embodiments, the invention provides an isolated TIMP-3 polypeptide, variant, derivative or mutein; an isolated nucleic acid encoding the TIMP-3 polypeptide, variant, derivative or mutein; and an isolated host cell comprising the nucleic acid or expression vector or producing the polypeptide, variant, derivative or mutein.

The terms "peptide," "polypeptide," and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently, or non-covalently, modified proteins. A peptide, polypeptide, or protein may be monomeric or polymeric.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence or a tag protein).

A "variant" or "mutein" of a polypeptide (e.g., a TIMP-3 variant or mutein) comprises an amino acid sequence wherein one or more amino acid residues are inserted into, deleted from and/or substituted into the amino acid sequence relative to another polypeptide sequence. Variants of the invention include fusion proteins. It will be understood that, unless context dictates otherwise, features of "polypeptides" or "proteins" described herein are also attributed to variants, muteins, and derivatives.

A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991), which are each incorporated herein by reference.

One way of referring to the degree of similarity of a variant or mutein to the native protein is by referring to the percent identity between the two (or more) polypeptide sequences, or the encoding nucleic acids sequences, being compared. The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

A "derivative" of a polypeptide is a polypeptide (e.g., a TIMP-3 polypeptide, variant or mutein) that has been chemically modified, e.g., via conjugation to another chemical moiety (such as, for example, polyethylene glycol or albumin, e.g., human serum albumin), phosphorylation, and/or glycosylation.

Polynucleotide and polypeptide sequences are indicated using standard one- or three-letter abbreviations. Unless otherwise indicated, each polypeptide sequence has an amino terminus at the left and a carboxy terminus at the right; each single-stranded nucleic acid sequence, and the top strand of each double-stranded nucleic acid sequence, has a 5' terminus at the left and a 3' terminus at the right. A particular polypeptide or polynucleotide sequence also can be described by explaining how it differs from a reference sequence. For example, substitutions of amino acids are designated herein as "n # m" where "n" designates the amino acid found in the native, full-length polypeptide, "#" designates the amino acid residue number, and "m" designates the amino acid that has been substituted.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding a TIMP-3 polypeptide, fragment, variant, derivative or mutein, of the invention. Nucleic acid sequences encoding TIMP-3 muteins, variants, or derivatives described herein are set forth in SEQ ID NOs: 27-50 and 61-70. Nucleotides 1-69 of SEQ ID NOs" 27-50 and 61-70 comprise the TIMP signal sequence. The invention includes a nucleic acid comprising a nucleotide sequence comprising at least 90% identity (e.g., at least 95% identity or 100% identity) to SEQ ID NOs: 27-50 and 61-70, as well as SEQ ID NOs: 27-50 and 61-70 lacking nucleotides 1-69.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06.

Naturally occurring extracellular proteins typically include a "signal sequence," which directs the protein into the cellular pathway for protein secretion and which is not present in the mature protein. The signal sequence may also be referred to as a "signal peptide" or "leader peptide" and is enzymatically cleaved from the extracellular protein. The protein that has been so processed (i.e., having the signal sequence removed) is often referred to as "mature" protein. A polynucleotide encoding a protein or polypeptide of the invention may encode a naturally occurring signal sequence or a heterologous signal sequence, numerous of which are known in the art.

As appreciated by one of skill in the art, recombinant proteins or polypeptides in accordance with the present embodiments can be expressed in cell lines, including mammalian cell lines. Sequences encoding particular proteins can be used for transformation of a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216; 4,912,040; 4,740,461; and 4,959,455 (which patents are hereby incorporated herein by reference). The transformation procedure used depends upon the host to be transformed. Methods for introduction of heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

A "host cell" is a cell that can be used to express a nucleic acid, e.g., a nucleic acid of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells.

Typically, a host cell is a cultured cell that can be transformed or transfected with a polypeptide-encoding nucleic acid, which can then be expressed in the host cell. In a "transient transfection," the nucleic acid is introduced into the host cell by one of several methods known in the art, and the recombinant protein is expressed for a finite period of time, typically up to about four days, before the nucleic acid is lost or degraded, for example, when the host cell undergoes mitosis. If a "stable transfection" is desired, the polypeptide-encoding nucleic acid may be introduced into the host cell along with a nucleic acid encoding a selectable marker. Use of a selectable marker allows one of skill in the art to select transfected host cells in which the polypeptide-encoding nucleic acid is integrated into the host cell genome in such a way that the polypeptide-encoding nucleic acid is maintained through mitosis, and can be expressed by progeny cells.

The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

As used herein, "TIMP-3 DNA," "TIMP-3-encoding DNA" and the like indicate a selected TIMP-3 encoding nucleic acid in which the TIMP-3 that is expressed therefrom may be either native TIMP-3 or a TIMP-3 variant or mutein as described herein. Likewise, "TIMP-3,""TIMP-3 protein" and "TIMP-3 polypeptide" are used to designate either a native TIMP-3 protein or a TIMP-3 protein comprising one or more mutations (i.e., a TIMP-3 polypeptide, variant, derivative or mutein). A particular mutein of TIMP-3 may be designated by the mutation or mutations, for example, "K45N" or "K45N TIMP-3" or "TIMP-3 K45N" or "K45N TIMP-3 polypeptide" indicates a polypeptide in which the lysine (K) at amino acid 45 of native TIMP-3 has been substituted with an asparagine (N).

The term "native TIMP-3" as used herein refers to wild type TIMP-3. TIMP-3 is expressed by various cells or tissues in a mammal and is present in the extracellular matrix; the TIMP-3 that is so expressed is also referred to herein as "endogenous" TIMP-3. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. The amino acid numbering system used in U.S. Pat. No. 6,562,596 designates the amino acids in the signal (or leader) peptide with negative numbers, and references the mature protein (i.e., the protein from which the signal or leader peptide has been removed) as amino acids 1-188. The numbering systems used herein refers to TIMP-3 with the first amino acid of the native leader peptide designated #1; the full-length TIMP-3 thus includes amino acids 1-211, and the mature form is amino acids 24-211. Those of ordinary skill in the art readily comprehend the differences in amino acid numbering that may occur by the use of these different numbering systems, and can thus easily apply the numbering system used herein to, for example, a TIMP-3 polypeptide in which the first amino acid of the mature form is referred to as #1. Thus, for example, K45N as designated herein would be designated K22N using the numbering system of U.S. Pat. No. 6,562,596.

TIMP-3 is formed of two domains, an N-terminal domain comprising amino acids 24 through 143 of TIMP-3 (i.e., about two-thirds of the molecule), and the C-terminal domain, which comprises amino acids 144 through 211. TIMP-3 exhibits complex disulphide bonds that facilitate formation of the secondary and tertiary structure TIMP-3. The N-terminal domain of TIMP-3, often referred to as "N-TIMP-3," has been found to exhibit at least some of the biological activities of TIMP-3; accordingly, TIMP-3 variants, derivatives and muteins as described herein include variants, derivatives and muteins of a fragment of TIMP-3 that comprises the N-terminal domain.

Native TIMP-3 protein presents several challenges for its use as a therapeutic molecule. For example, mammalian expression titers for TIMP-3 protein using standard mammalian expression techniques are too low to allow sufficient quantities of TIMP-3 to be produced at a scale that is suitable for a therapeutic protein. Moreover, the binding of TIMP-3 to extracellular matrix necessitates the inclusion of heparin (or a similar agent that reduces binding of TIMP-3 to extracellular matrix) in cell culture medium, and binding to the Low density lipoprotein Receptor-related Protein 1 (LRP1) scavenger protein exacerbates the challenge of secretion of recombinant TIMP-3 into the medium at a level that allows a production-scale process to be developed. Microbial production in prokaryotic cells of full-length TIMP-3 has proved difficult due to incorrect folding of the protein.

Accordingly, the TIMP-3 variants or muteins of the invention have been modified to overcome one or more of these challenges. Polypeptides of the invention include polypeptides that have been modified in any way and for any reason, for example, to: (1) reduce susceptibility to proteolysis, (2) reduce susceptibility to oxidation, (3) reduce the need for agents that inhibit binding of TIMP-3 to extracellular matrix in cell culture, (4) alter binding affinities for other moieties, for example scavenger receptors such as LRP-1, (5) confer or modify other physicochemical or functional properties, including pharmacokinetics and/or pharmacodynamics, or (6) facilitate expression and/or purification of recombinant protein. Analogs include muteins of a polypeptide. For example, single or multiple amino acid substitutions (e.g., conservative amino acid substitutions) may be made in the naturally occurring sequence (e.g., in the portion of the polypeptide outside the domain(s) forming intermolecular contacts). Consensus sequences can be used to select amino acid residues for substitution; those of skill in the art recognize that additional amino acid residues may also be substituted.

In one aspect of the invention, there is provided a TIMP-3 mutein or variant that exhibits an increase in expression levels of the mutein or variant over that observed with native TIMP-3; in another aspect of the invention the increased expression occurs in a mammalian cell expression system. Expression levels may be determined by any suitable method that will allow a quantitative or semi-quantitative analysis of the amount of recombinant TIMP-3 (native, variant or mutein) in cell culture supernatant fluid, i.e., conditioned media (CM). In one embodiment, samples or CM are assessed by Western blot; in another embodiment, CM samples are assessed using a standard human TIMP-3 ELISA.

In one embodiment, the increase in expression is observed in a transient expression system; in another embodiment, the increase in expression is observed in a stable transfection system. One embodiment provides a TIMP-3 mutein or variant for which the increase in expression observed is two-fold (2×) greater than that observed for native TIMP-3; another embodiment provides a TIMP-3 mutein or variant for which the increase in expression observed is five-fold (5×) greater than that observed for native TIMP-3. Further embodiments include TIMP-3 muteins or variants for which the increase in expression is three-fold (3×), four-fold (4×) or six-fold (6×). In one embodiment, the expression of the TIMP-3 mutein or variant is ten-fold (10×) greater than that observed with native TIMP-3; in another embodiment, the observed expression is more than ten-fold, for example, 20-fold (20×) or greater, than that observed with native TIMP-3.

In another aspect of the invention, there are provided TIMP-3 muteins (or variants) that exhibit reduced requirement for the addition of heparin (or another agent that inhibits binding of TIMP-3 to extracellular matrix) to cell culture media (i.e., heparin independence). The reduction in the amount of heparin (or other agent) may be described in a semi-quantitative manner, i.e., the reduction may be partial, moderate, substantial, or complete. In another embodiment, the reduction is expressed as a percentage, for example the amount of heparin (or similar agent) may be reduced by 10%, 20%, 30%, 40%, 50%, or more (for example by 60%, 70% 80%, 90% or 100%). Examples of TIMP-3 muteins with at least some degree of heparin independence include, but are not limited to, TIMP-3 K45S, F57N fused to HSA; TIMP-3 K45N/V47T, P56N/G58T, K94N/E96T, R138T (SEQ ID NO: 4); TIMP-3 K45N/V47T, K94N/E96T, D110N/K112T, G173T (SEQ ID NO: 9); TIMP-3 H78N/Q80T, K94N/E96T, D110N/K112T, R138T (SEQ ID NO: 26); and TIMP-3 H78N/Q80T, K94N/E96T, D110N/K112T, R138T (SEQ ID NO: 26) fused to HSA. N-TIMP-3 fused to HSA can be produced using reduced levels of heparin. In one embodiment, there are provided TIMP-3 variants or muteins comprising inserted glycosylation sites. As is known in the art, glycosylation patterns can depend on both the sequence of the protein (e.g., the presence or absence of particular glycosylation amino acid residues, discussed below), or the host cell or organism in which the protein is produced. Particular expression systems are discussed below. The presence, absence, or degree of glycosylation may be determined by any method that is known to one of skill in the art, including semiqualitative measures of shifts in molecular weight (MW) as observed by western blotting or from coomassie stained SDS-PAGE gels, while quantitative measures can include utilizing mass spectrophotometer techniques and observation of MW shifts corresponding to addition of asparagine-linked glycosylation, or through observation of mass shift with the removal of asparagine-linked glycosylation by an enzyme such as Peptide-N-Glycosidase F (PNGase-F; SigmaAldrich, St. Louis, Mo.).

Glycosylation of polypeptides is typically either N-linked or O-linked. N-linked refers to the attachment of the carbohydrate moiety to the side chain of an asparagine residue. The tri-peptide sequences asparagine-X-serine (N X S) and asparagine-X-threonine (N X T), where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to a protein (e.g., TIMP-3) is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the protein amino acid sequence is preferably altered through changes at the DNA level, particularly by mutating the DNA encoding the target polypeptide at preselected bases such that codons are generated that will translate into the desired amino acids.

Accordingly, N-linked glycosylation sites may be adding by altering a codon for a single amino acid. For example, codons encoding N-X-z (where z is any amino acid) can be altered to encode N-X-T (or N-13 X-S), or codons encoding y-X-T/S can be altered to encode N-X-T/S. Alternatively, codons encoding two amino acids can be simultaneously changed to introduce an N-linked glycosylation site (for example, codons for y-X-z can be altered to encode N-13 X-T/S). In this manner, from one to twelve N-linked glycosylation sites can be inserted. Glycosylation insertion may also be useful for expression improvement (see, for example, Enhancing the Secretion of Recombinant Proteins by Engineering N-Glycosylation Sites. Liu Y. et al, Amer Inst Chem Eng 2009, pg. 1468).

In addition to inserting N-linked glycosylation sites into TIMP-3, any glycosylation sites that are present in native TIMP-3 can be modified, for example in an effort to stabilize the structure of the molecule. Thus, for example, the A at residue 208 may be substituted with a different residue, such as Y, V, or G. Additional modifications at the 'N-13 X-T' site at residues 206-208 include substituting F for I at residue 205, or Y for I at residue 205, in combination with one of the aforementioned substitutions at residue 208.

Thus, in another embodiment, a sub-set of solvent exposed sites developed by computational analysis are screened for N-glycosylation likelihood. For methods involving insertion of glycosylation sites, an N-glycosylation prediction tool is useful in selecting sites that may be mutated to facilitate potential N-linked glycosylation, for example by identifying residues that could be mutated to form a canonical N-x-T glycosylation site (where N is asparagine, x is any amino acid and T is threonine). In a further embodiment, structure based methods are used to identify all solvent exposed amino acids (including those amino acids with sidechain exposure >20 Å$^2$). An additional embodiment includes the mutation of LRP1 interacting lysines on TIMP-3, based upon the crystal structure of LRP1/RAP (Receptor Associated Protein) with interacting RAP lysines mapped against TIMP-3.

Additional combinations are contemplated herein. For example, any mutation disclosed herein can be made in combination with a mutation at a lysine residue, wherein the lysine residue is any lysine in TIMP-3. In one embodiment, a single lysine is mutated; in another embodiment, two, three, four or five lysine residues are mutated. In certain embodiments, lysine residues at amino acid 45 and/or 133 can be mutated. In another example, a mutation introduces a single N-linked glycosylation site; this mutation can be made with additional mutations to introduce additional glycosylation sites, or with other mutations designed to affect another property of TIMP-3. Contemplated herein are TIMP-3 muteins or variants, that comprise one introduced N-linked glycosylation site, that comprise two, three or four introduced N-linked glycosylation sites, and that comprise five or more introduced N-linked glycosylation sites.

Figure 2:
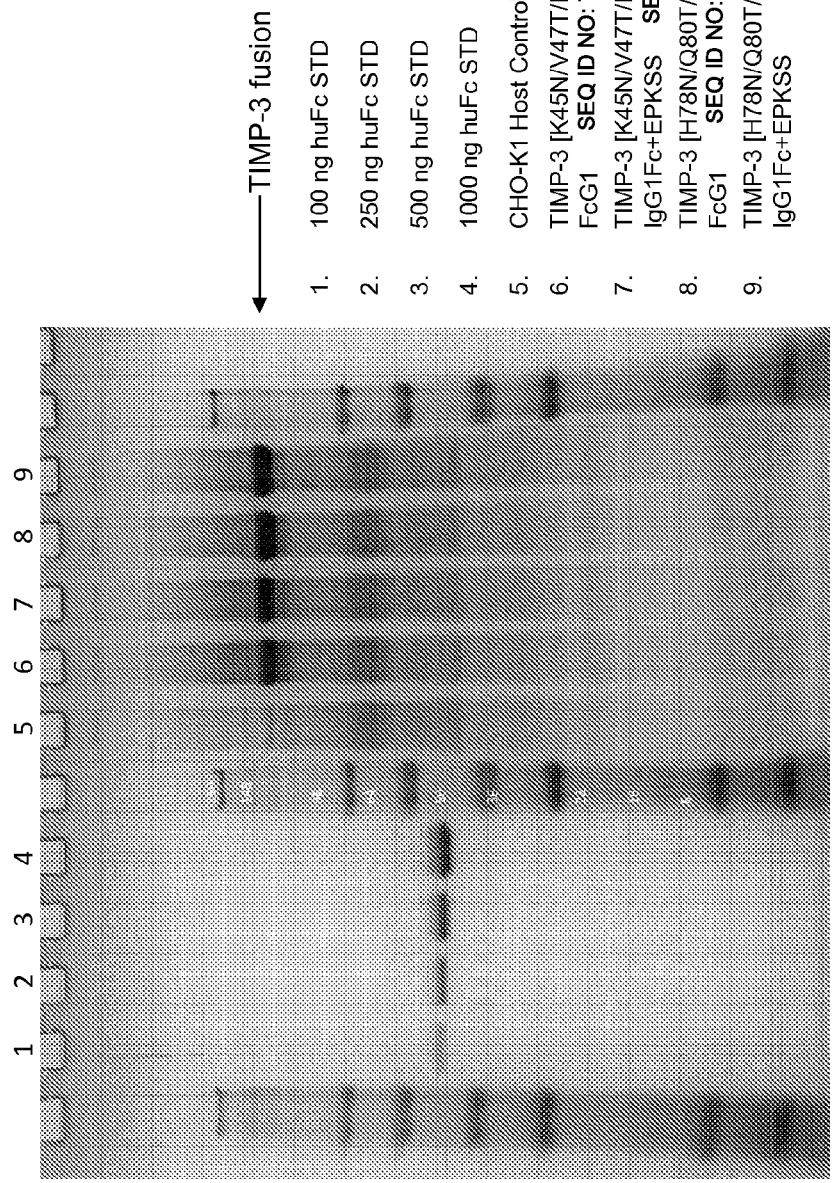
FIG. 2 is a reproduction of an SDS-PAGE gel illustrating the amount of a TIMP-3 mutein fused to Fc portion of an antibody produced in the absence of heparin. Lane #1-4 contained Fc standards ("STD"): Lane #1 contained 100 ng human Fc; Lane #2 contained 250 ng human Fc; Lane #3 contained 500 ng human Fc; and Lane #4 contained 1000 ng human Fc. Lane #5 represented a host cell control sample. Lanes #6-9 contained 10 µL samples from culture media of CHOK1 cells expressing TIMP-3 mutein-Fc: TIMP-3 [K45N/V47T/K94N/E96T/D110N/K112T/G173T]-FcG1 fusion (Lane #6), TIMP-3 [K45N/V47T/K94N/E96T/D110N/K112T/G173T]-IgG1Fc+EPKSS fusion (Lane #7), TIMP-3 [H78N/Q80T/K94N/E96T/D110N/K112T/R138T]-FcG1 fusion (Lane #8), or TIMP-3 [H78N/Q80T/K94N/E96T/D110N/K112T/R138T]-IgG1Fc+EPKSS fusion (Lane #9).

Particular mutations are shown in FIGS. 1 and 2 of U.S. application Ser. No. 14/207,178, filed 12 Mar. 2014, and PCT Application PCT/US2014/026811, filed 13 Mar. 2014, the disclosures of which are incorporated by reference herein. Those Figures present an alignment of native, full-length human TIMP-3 and a mutated form of full-length human TIMP-3 in which the letter "X" has been substituted for particular amino acids within the sequence. The signal sequence is underlined; other signal sequences can be substituted therefore, as described herein.

The amino acid sequences of selected muteins are presented herein in the Sequence Listing. Full length protein sequences are provided. In many instances, a signal sequence is not present in the sequences set forth for the various muteins in the sequence listing to facilitate a consistent amino acid residue numbering system and the understanding of those of skill in the art of the amino acid designations used herein. The invention includes the mutein sequences set forth herein further comprising a signal sequence which is, in various embodiments, the sequence provided in SEQ ID NO:2 as amino acids 1-23 (i.e., MTPWLGLIVLLGSWSLGDWGAEA). SEQ ID NO:2 is a representative native TIMP-3 amino acid sequence. One of skill in the art will appreciate that the signal peptide is removed during processing of the protein to result in a mature protein with an N-terminus starting with the amino acid cysteine. In various embodiments, the N-terminal cysteine is preserved in the TIMP-3 mutein. One of skill in the art will also appreciate that between expression of TIMP-3 mutein DNA in a cell and isolation of the protein, post-translational modification of the protein occurs. Specific examples of post-translational modifications include glycosylation (e.g., N-linked glycosylation) and removal of the signal peptide; further modifications including phosphorylation, ubiquitination, nitrosylation, methylation, acetylation, lipidation, proteolysis, and the like also are contemplated.

It is known that the native TIMP-3 signal sequence can be used to express TIMP-3 muteins, or another signal sequence can be substituted. Thus, the amino acid at residue 1 can be M or another amino acid; the amino acid at residue 2 can be T or another amino acid, the amino acid at residue 3 can be P or another amino acid, etc. through amino acid 23. Additionally, a signal sequence can comprise additional amino acids (i.e., be longer than the signal sequence of naïve TIMP-3), or can comprise fewer amino acids than 23 (i.e., be shorter than the signal sequence of naïve TIMP-3). Regardless of the length of the signal sequence, those of ordinary skill in the art will be able to utilize the numbering system herein to prepare the presently disclosed TIMP-3 muteins, as well as other muteins that could be made.

Certain substitutions are envisioned in the mature form of TIMP-3, and are designated herein as "n # m" where "n" designates the amino acid found in the native, full-length TIMP-3, "#" designates the amino acid residue number, and "m" designates the amino acid that has been substituted. Thus, for example, "K45N" indicates that the lysine (K) at amino acid 45 has been substituted with asparagine (N). The mutated forms of human TIMP-3 exemplified herein comprise the following mutations (alone, or in combination): K45N; V47T; K50N; V52T H78N; K94N; E96T; D110N; K112T; R138T; and G173T. Combinations of these mutations are also contemplated, and can include from two to twelve (i.e., 2, 3, 4, 5, 6, 7 8, 9, 10, 11 or 12) of the afore-mentioned substitutions. For example, in one embodiment, the TIMP-3 mutein comprises (or consists of) amino acids 24-211 of SEQ ID NO:2 having the following substitutions: H78N, Q80T, K94N, E96T, D110N, K112T, and R138T.

Specific combinations of mutations include K50N/V52T, D110N/K112T, R138T, G173T; K45N/V47T, D110N/K112T, R138T, G173T; H78N/Q80T, D110N/K112T, R138T, G173T; K45N/V47T, K50N/V52T, H78N/A80T, R138T; K45N/V47T, H78N/Q80T D110N/K112T,G173T; K45N/V47T, H78N/Q80T, R138T, G173T; K50N/V52T, H78N/Q80T, K94N/E96T,G173T; K50N/V52T, H78N/Q80T, D110N/K112T, R138T; K45N/V47T, K50N/V52T, H78N/Q80T, D110N/K112T; K50N/V52T, H78N/Q80T, R138T, G173T; K45N/V47T, H78N/Q80T, R138T, G173T; K45N/V47T, H78N/Q80T, D110N/K112T, R138T; K45N/V47T, K50N/V52T, H78N/Q80T, D110N/K112T, G173T; K45N/V47T, K50N/V52T, H78N/Q80T, D110N/K112T, R138T; K45N/V47T, K50N/V52T, H78N/Q80T, R138T, G173T; K45N/V47T, K50N/V52T, H78N/Q80T, K94N/E96T, G173T; K45N/V47T, H78N/Q80T, K94N/E96T,R138T, G173T; K50N/V52T, H78N/Q80T, K94N/E96T, R138T, G173T; K45N/V47T, H78N/Q80T, D110N/K112T, R138T, G173T; K50N/V52T, H78N/Q80T, D110N/K112T, R138T, G173T; and K45N/V52T, K50N/V52T, H78N/Q80T, D110N/K112T, R138T.

Additional combinations include K50N/V52T, D110N/K112T, R138T, G173T; K45N/V47T, D110N/K112T, R138T, G173T; H78N/Q80T, D110N/K112T, R138T, G173T; K45N/V47T, K50N/V52T, H78N/A80T, R138T; K45N/V47T, H78N/Q80T D110N/K112T,G173T; K45N/V47T, H78N/Q80T, R138T, G173T; K50N/V52T, H78N/Q80T, K94N/E96T,G173T; K50N/V52T, H78N/Q80T, D110N/K112T, R138T; K45N/V47T, K50N/V52T, H78N/Q80T, D110N/K112T; K50N/V52T, H78N/Q80T, R138T, G173T; K45N/V47T, H78N/Q80T, R138T, G173T; K45N/V47T, H78N/Q80T, D110N/K112T, R138T; K45N/V47T, K50N/V52T, H78N/Q80T, D110N/K112T,G173T; K45N/V47T, K50N/V52T, H78N/Q80T, R138T, G173T; K45N/V47T, K50N/V52T, H78N/Q80T, K94N/E96T,G173T; K45N/V47T, H78N/Q80T, K94N/E96T,R138T, G173T; K50N/V52T, H78N/Q80T, K94N/E96T, R138T, G173T; K45N/V47T, H78N/Q80T, D110N/K112T, R138T,G173T; K50N/V52T, H78N/Q80T, D110N/K112T, R138T,G173T; and K45N/V47T, K50N/V52T, H78N/Q80T, D110N/K112T, R138T.

In various embodiments, the mutein is K45N, V47T, P56N, G58T, Q126N, R138T (SEQ ID NO:3); K45N, V47T, P56N, G58T, K94N, E96T, R138T (SEQ ID NO:4); K45N, V47T, P56N, G58T, R138T, G173T (SEQ ID NO:5); K45N, V47T, F57N, K94N, E96T, D110N, K112T (SEQ ID NO:6); K45N, V47T, F57N, K94N, E96T, R138T (SEQ ID NO:7); K45N, V47T, H78N, Q80T, K94N, E96T, R138T, G173T (SEQ ID NO:8); K45N, V47T, K94N, E96T, D110N, K112T, R138T (SEQ ID NO:9); K45N, V47T, K94N, E96T, D110N, K112T, G173T (SEQ ID NO:10); K45N, V47T, K94N, E96T, R138T, G173T (SEQ ID NO:11); K45S, F57N, K94N, E96T, D110N, K112T, R138T (SEQ ID NO:12); K45S, F57N, H78N, Q80T, K94N, E96T, R138T (SEQ ID NO:13); K50N, V52T P56N, G58T, K94N, E96T, D110N, K112T, R138T (SEQ ID NO:14); K50N, V52T, H78N, Q80T, K94N, E96T, R138T, G173T (SEQ ID NO:15); K50N, V52T, K94N, E96T, D110N, K112T, R138T (SEQ ID NO:16); K50N, V52T, K94N, E96T, D110N, K112T, R138T, G173T (SEQ ID NO:17); K50N, V52T, K94N, E96T, R138T, G173T (SEQ ID NO:18); K50N, V52T, Q126N, R138T, G173T (SEQ ID NO:19); P56N, G58T, H78N, Q80T, K94N, E96T, R138T (SEQ ID NO:20); P56N, G58T K94N, E96T, Q126N, R138T (SEQ ID NO:21); P56N, G58T, K94N, E96T, D110N, K112T, R138T (SEQ ID NO:22); P56N, G58T, H78N, Q80T, K94N, E96T, G173T (SEQ ID NO:23); P56N, G58T, Q126N, R138T, G173T (SEQ ID NO:24); H78N, Q80T, K94N, E96T, R138T, G173T (SEQ ID NO:25).

The TIMP-3 variants, muteins or derivative have an amino acid sequence that is quite similar to that of native TIMP-3. In one embodiment, a TIMP-3 variant, mutein or derivative will be at least 85% identical to native TIMP-3; in another embodiment, a TIMP-3 variant, mutein or derivative will be at least 90% identical to native TIMP-3; in another embodiment, a TIMP-3 variant, mutein or derivative will be at least 95% identical to native TIMP-3. In further embodiments, a TIMP-3 variant, mutein or derivative is at least 96% identical, 97% identical, 98% identical or 99% identical to native TIMP-3. As used herein, the percent identities refer to a comparison of the mature, full-length variant, mutein or derivative to the mature, full-length form of native TIMP-3, i.e., TIMP-3 lacking a signal peptide (amino acids 24 through 211 of TIMP-3). Those of skill in the art will readily understand that a similar comparison can be made between a variant, mutein or derivative of the N-terminal domain of TIMP-3 and the N-terminal domain of native TIMP-3.

Similarity can also be expressed by the number of amino acids that differ between a mutein or variant and a native TIMP-3. For example, a TIMP-3 variant or mutein can vary from native TIMP-3 by one amino acid, two amino acids, three amino acids, four amino acids, five amino acids, six amino acids, seven amino acids, eight amino acids, nine amino acids, or ten amino acids. A variant or mutein that differs from native TIMP-3 at ten amino acids will be about 95% identical to native TIMP-3. In further embodiments, a TIMP-3 variant or mutein differs from native mature TIMP-3 at 11, 12, 13, 14, 15, 16, 17, 18, 19 or 20 amino acids Additional changes can be made in a nucleic acid encoding a TIMP-3 polypeptide (either native, mutein, variant or derivative) to facilitate expression. For example, the signal peptide of native TIMP-3 can be substituted with a different signal peptide.

Other derivatives of TIMP-3 polypeptides within the scope of this invention include covalent or aggregative conjugates of TIMP-3 polypeptides, or fragments thereof, with other proteins or polypeptides, such as by expression of recombinant fusion proteins comprising heterologous polypeptides fused to the N-terminus or C-terminus of a TIMP-3 polypeptide. For example, the conjugated peptide may be a heterologous signal (or leader) peptide, e.g., the yeast alpha-factor leader, or a peptide such as an epitope tag. Those of ordinary skill in the art understand that a heterologous signal peptide may differ in length from the native TIMP-3 signal peptide, but can correctly identify the location of muteins with respect to the amino acid sequence of mature TIMP-3 by aligning the N-terminal cysteine residues of TIMP-3 polypeptides produced using a heterologous signal peptide.

TIMP-3 polypeptide-containing fusion proteins can comprise peptides added to facilitate purification or identification of the TIMP-3 polypeptide (e.g., poly-His). Another tag peptide is the FLAG® peptide described in Hopp et al., *Bio/Technology* 6:1204, 1988, and U.S. Pat. No. 5,011,912. The FLAG® peptide is highly antigenic and provides an epitope reversibly bound by a specific monoclonal antibody (mAb), enabling rapid assay and facile purification of expressed recombinant protein. Reagents useful for preparing fusion proteins in which the FLAG® peptide is fused to a given polypeptide are commercially available (Sigma, St. Louis, Mo.).

In various embodiments, the TIMP-3 polypeptide described herein (e.g., any one of the TIMP-3 muteins described herein) is fused to a moiety that extends the half-life of the polypeptide in vivo. Exemplary moieties include, but are not limited to, an antibody (e.g., IgG) or a fragment thereof (e.g., the Fc portion of an antibody such as an IgG) or albumin (e.g., human serum albumin). Alternatively or in addition, the TIMP-3 polypeptide comprises an albumin binding domain or fatty acid that binds albumin when administered in vivo. An example of an albumin binding domain is "albu-tag," a moiety derived from on 4-(p-iodophenyl)-butanoic acid (Dumelin et al., Angew Chem Int Ed Engl 47:3196-3201 (2008)). The moiety may be fused to the N-terminus of the TIMP-3 polypeptide or fused to the C-terminus, and the moiety itself may be in any orientation (i.e., connected by the moiety N- or C-terminus). Optionally, the moiety is attached to the TIMP-3 polypeptide via a linker, such as a flexible peptide linker (e.g., a linker comprising 1-10 or 2-4 glycines, for example, four glycines, or EPKSS (SEQ ID NO: 75)). Examples of fusion partners for the TIMP-3 polypeptides described herein include, but are not limited to human serum albumin of SEQ ID NO: 71, human FcG1 of SEQ ID NO: 72, Fc-mono of SEQ ID NO: 73, and human Fc-mono Ndel5 of SEQ ID NO: 74. The invention contemplates fusion proteins comprising any of the muteins described herein (e.g., SEQ ID NOs: 3-26) fused to any of the fusion partners described herein (e.g., SEQ ID NOs: 71-74).

Covalent modifications are also considered derivatives of the TIMP-3 polypeptides and are included within the scope of this invention, and are generally, but not always, done post-translationally. For example, several types of covalent modifications of the TIMP-3 are introduced into the molecule by reacting specific amino acid residues of the antigen binding protein with an organic derivatizing agent that is capable of reacting with selected side chains or the N- or C-terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Accordingly, in one aspect of the invention, cysteinyl residues are added to the native TIMP-3 sequence, for example by altering selected codon(s) to encode Cys. Such Cys substitution can be made in regions of TIMP-3 that are shown to be important for expression, folding or other properties as shown herein.

The number of carbohydrate moieties on the proteins of the invention can be increased by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, *CRC Crit. Rev. Biochem.*, pp. 259-306.

Removal of carbohydrate moieties present on the starting recombinant protein may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et aL, 1987, Arch. Biochem. Biophys. 259:52 and by Edge et aL, 1981, *Anal. Biochem.* 118:131. Enzymatic cleavage of carbohydrate moieties on polypeptides can be achieved by the use of a variety of endo- and exo-glycosidases as described by Thotakura et aL, 1987,

*Meth. Enzymol.* 138:350. Glycosylation at potential glycosylation sites may be prevented by the use of the compound tunicamycin as described by Duskin et al., 1982, *J. Biol. Chem.* 257:3105. Tunicamycin blocks the formation of protein-N-glycoside linkages.

Another type of covalent modification of the antigen binding protein comprises linking the protein to various nonproteinaceous polymers, including, but not limited to, various polyols such as polyethylene glycol (e.g., PEG approximately 40 kD, 30 kD, 20 kD, 10, kD, 5 kD, or 1 kD in size), polypropylene glycol or polyoxyalkylenes, in the manner set forth in U.S. Pat. Nos. 4,640,835; 4,496,689; 4,301,144; 4,670,417; 4,791,192 or 4,179,337. Other useful polymers include, but are not limited to, monomethoxypolyethylene glycol, dextran, hydroxyethyl starch, cellulose, poly-(N-vinyl pyrrolidone)-polyethylene glycol, propylene glycol homopolymers, a polypropylene oxide/ethylene oxide co-polymer, polysialic acid (PSA), polyoxyethylated polyols (e.g., glycerol) and polyvinyl alcohol, as well as mixtures of any of the foregoing. In one aspect, the TIMP-3 polypeptide of the invention is a PEGylated peptide. In addition, as is known in the art, amino acid substitutions may be made in various positions within the protein to facilitate the addition of such polymers.

In various aspects, the modifications to the native TIMP-3 amino acid sequence to arrive at the TIMP-3 variant, mutein, or derivative of the invention does not substantially diminish native TIMP-3 activity. For example, the TIMP-3 variant, mutein, or derivative preferably inhibits one or more matrix metalloproteinases (e.g., MMP-2, MMP-9, and/or MMP-13), inhibits one or more aggrecanases (ADAMS) (e.g., ADAMTS4 and/or ADAMTS5), inhibits tumor-necrosis factor alpha (TNF-alpha)-converting enzyme (TACE), inhibits TNF-alpha production in vitro or in vivo, inhibits extracellular matrix degradation, and/or inhibits inflammation. Exemplary methods of characterizing the activity of a TIMP-3 polypeptide are provided in the Examples. Optionally, the TIMP-3 variant, mutein, or derivative exhibits at least about 30%, at least about 40%, at least about 50%, at least about 60%, at least about 70%, at least about 80%, at least about 90%, at least about 95%, or about 100% of any one of the activities associated with native TIMP-3, including the activities set forth above. Alternatively or in addition, the TIMP-3 variant, mutein, or derivative optionally exhibits no more than a 10-fold decrease, no more than a 5-fold decrease, or no more than a 2-fold decrease in activity (e.g., MMP-2 or MMP-9 inhibition) compared to native TIMP-3.

Expression of TIMP-3 Polypeptides

Any expression system known in the art can be used to make the recombinant polypeptides of the invention. In general, host cells are transformed with a recombinant expression vector that comprises DNA encoding a desired TIMP-3 polypeptide (including TIMP-3 muteins or variants). Among the host cells that may be employed are prokaryotes, yeast or higher eukaryotic cells. Prokaryotes include gram negative or gram positive organisms, for example E. coli or bacilli. Higher eukaryotic cells include insect cells and established cell lines of mammalian origin. Examples of suitable mammalian host cell lines include the COS-7 line of monkey kidney cells (ATCC CRL 1651) (Gluzman et aL, 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CVI/EBNA cell line derived from the African green monkey kidney cell line CVI (ATCC CCL 70) as described by McMahan et aL, 1991, EMBO J. 10: 2821. Appropriate cloning and expression vectors for use with bacterial, fungal, yeast, and mammalian cellular hosts are described by Pouwels et al. (*Cloning Vectors: A Laboratory Manual*, Elsevier, New York, 1985).

Mammalian cell expression can provide advantages for the production of TIMP-3 polypeptides, in facilitating folding and adoption of conformation that closely resembles that of native TIMP-3. Numerous mammalian cell expression systems are known in the art, and/or are commercially available; the latter includes systems such as Gibco®Freedom® CHO-S® (a product designed for ease of use with all aspects of cloning and expression of recombinant proteins in Chinese Hamster Ovary (CHO)-derived suspension culture; ProBioGen, Life Technologies; Carlsbad, Calif.), GS Gene Expression System™ (a transfection system designed to provide development of high-yielding, stable, cGMP-compatible mammalian cell lines; Lonza Biologics, Slough, UK), PER.C6® technology (a package of tools designed to facilitate the large-scale production of recombinant proteins, utilizing a continuously dividing set of cells derived from a single, immortalized human cell; Crucell, Leiden, The Netherlands), or immortalized amniocyte cells such as CAP and CAP-T (human cell-based expression systems for the expression and production of complex proteins; Cevec, Cologne, Germany).

Additional cell expression systems include systems such as the Selexis SUREtechnology Platform™ (a technology platform that can be applied to a variety of cell lines to facilitate development cell lines for the production of recombinant proteins; Selexis Inc., Switzerland); ProFection® Mammalian Transfection Systems (a transfection system that provides high-efficiency transfections of cells for the production of recombinant proteins; Promega, Madison Wis.); the Expi293™ Expression System (a high-density mammalian transient protein expression system, Life Technologies, Grand Island, N.Y.); and MaxCyte® VLXTM and STX™ Transient Transfection Systems (a scalable transfection system for use in the production of recombinant proteins, including antibodies; MaxCyte, Gaithersurg, Md.). Those of skill in the art are further aware of other expression systems, such as techniques originally described by Wigler et al. (Cell 1979:777) and additional techniques that are described, for example, by the National Research Council of Canada on their website.

Various vessels are known in the art to be suitable for the culture of transformed cells and production of recombinant proteins. These include 24-deep well plates, 250 ml and 1 L shakeflasks; and various bioreactors of various sizes, for example, 2 L, 5 L, 10 L, 30 L, 100 L, 1000 L, 10000 L and larger Bioreactors. Other suitable vessels for cell culture are known in the art and can also be used as described herein.

Cell culture media formulations are well known in the art; typically, a culture medium provides essential and non-essential amino acids, vitamins, energy sources, lipids, and trace elements required by the cell for minimal growth and/or survival, as well as buffers, and salts. A culture medium may also contain supplementary components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source; as described herein, cell-cycle inhibitors can be added to a culture medium. In certain embodiments, a medium is advantageously formulated to a pH and salt concentration optimal for cell survival and proliferation. In certain embodiments, the medium is a feed medium that is added after the beginning of the cell culture. In certain embodiments, the cell culture medium is a mixture of a starting nutrient solution and any feed medium that is added after the beginning of the cell culture.

Various tissue culture media, including defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (JRH Biosciences, Lenexa, Kans.), among others. Serum-free versions of such culture media are also available. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters.

The transformed cells can be cultured under conditions that promote expression of the polypeptide, and the polypeptide recovered by conventional protein purification procedures. One such purification procedure includes the use of affinity chromatography as well as other methods that are known in the art. One method to isolate TIMP-3 parent or TIMP-3 muteins from mammalian supernatants is to utilize a TIMP-3 that is fused to a carboxy-terminal 6×-Histidine tag in combination a 6×-Histidine affinity Ni-Sepharose resin (for example, Immobilized Metal Affinity Chromatography (IMAC); general procedures are known in the art, and reagents for, and examples of such procedures are outlined by QIAGEN, Germantown, Md. and GE Healthcare, Pittsburg, Pa.). Cation exchange chromatography (e.g. SP-HP Sepharose®, GE Healthcare) can be utilized to further isolate TIMP-3 post IMAC elution, or as an alternative strategy without the use of IMAC to capture TIMP-3 from mammalian supernatants (elution of TIMP-3 and muteins thereof occurs with the use of a sodium chloride gradient at neutral pH). Size Exclusion Chromatography (e.g., Superdex 200®, GE Heathcare, (mobile phase example: 10 mM $Na_2HPO_4$, 1.8 mM KH2PO4, 137 mM NaCl, 2.7 mM KCl),) is a general strategy that can be used to further isolate TIMP-3 or muteins thereof (in combination with an IMAC process or ion exchange chromatography. These and other methods are known in the art; see for example, Protein Purification: Principles: High Resolution Methods, and Applications, Third Edition (2012, John Wiley and Sons; Hoboken, N.J.).

The amount of polypeptide (native TIMP-3 or a TIMP-3 mutein or variant) can be determined by any suitable, quantitative or semi-quantitative method that will allow analysis of the amount of recombinant TIMP-3 (native, variant or mutein) in cell culture supernatant fluid, i.e., conditioned media (CM). Suitable qualitative or semi-quantitative methods include Western Blot and Coomassie stained SDS PAGE gels. Quantitative measurements could include use of an enzyme immunoassay such as a human TIMP-3 ELISA (R&D Systems Inc., Minneapolis, Minn.), or ForteBio Octet® (Pall ForteBio Corp, Menlo Park, Calif.) with antibody mediated capture of TIMP-3, or direct UV (ultraviolet) absorbance (280 nm) measurements on purified TIMP-3.

Thus, the effects of a particular mutation in TIMP-3 can be evaluated by comparing the amount of recombinant mutein made to the amount of native protein made under similar culture conditions. A TIMP-3 mutein or variant can be expressed at levels that are 1×, 2×, 3×, 4×, 5×, 10× or greater than levels observed for native TIMP-3. If desired, the specific productivity of a particular transformed or transfected cell line can be determined to allow comparison or the specific productivity for various forms of TIMP-3. Specific productivity, or qP, is expressed in picograms of recombinant protein per cell per day (pg/c/d), and can be readily determined by applying methods known in the art to quantitated the cells in a culture and the above-mentioned methods of quantifying recombinant protein.

Uses for TIMP-3 Polypeptides

TIMP-3 polypeptides, variants, muteins or derivatives can be used, for example, in assays, or they can be employed in treating any condition in which a greater level of TIMP-3 activity is desired (i.e., conditions in which matrix metalloproteases (MMPs) and/or other proteinases that are inhibited or inhibitable by TIMP-3 play a causative or exacerbating role), including but not limited to inflammatory conditions, osteoarthritis, and other conditions in which excessive or inappropriate MMP activity occurs (for example, myocardial ischemia, reperfusion injury, vasculopathy, neointima formation, and during the progression to chronic heart failure (e.g., congestive heart failure)). Inflammatory conditions include asthma, chronic obstructive pulmonary disease (COPD), and idiopathic pulmonary fibrosis (IPF), inflammatory bowel disease (for example, ulcerative colitis, Crohn's disease, and celiac disease), psoriases, myocarditis including viral myocarditis, inflammation related to atherosclerosis, and arthritic conditions including rheumatoid arthritis, psoriatic arthritis, and the like.

The TIMP-3 polypeptide, variant, mutein or derivative compositions described herein modify the pathogenesis and provide a beneficial therapy for diseases or conditions characterized by matrix degradation and/or inflammation, i.e., those in which metalloproteinases play a deleterious role. The compositions may be used alone or in conjunction with one or more agents used in treating such conditions. Accordingly, the present TIMP-3 polypeptide, variant, mutein or derivative compositions may be useful in the treatment of any disorder where excessive matrix loss (degradation) is caused by metalloproteinase activity. The inventive TIMP-3 variant, mutein or derivative compositions are useful, alone or in combination with other drugs, in the treatment of various disorders linked to the overproduction of collagenase, gelatinase, aggrecanase, or other matrix-degrading or inflammation-promoting enzyme(s), including dystrophic epidermolysis bullosa, osteoarthritis, pseudogout, rheumatoid arthritis including juvenile rheumatoid arthritis, ankylosing spondylitis, scleroderma, periodontal disease, ulceration including corneal, epidermal, or gastric ulceration, wound healing after surgery, and restenosis. Other pathological conditions in which excessive collagen and/or proteoglycan degradation may play a role and thus where TIMP-3 polypeptide, variant, mutein or derivative compositions can be applied, include emphysema, Paget's disease of bone, osteoporosis, scleroderma, pressure atrophy of bone or tissues as in bedsores, cholesteatoma, and abnormal wound healing. Additional conditions that are, directly or indirectly, a result of decreased amounts of TIMP-3 or increased amounts of metalloproteases (for example, in myocardial ischemia, reperfusion injury, and during the progression to congestive heart failure) may also be treated with the presently described compositions, either alone or in conjunction with other drugs commonly used to treat individuals afflicted with such conditions. The compositions described herein are useful for vascular plaque stabilization and inhibition of vascular neointima formation. TIMP-3 polypeptide, variant, mutein or derivative compositions can additionally be applied as an adjunct to other wound healing promoters, e.g., to modulate the turnover of collagen during the healing process.

Many metalloproteinases also exhibit pro-inflammatory activity; accordingly, additional embodiments include methods of treating inflammation and/or autoimmune disorders, wherein the disorders include, but are not limited to, cartilage inflammation, and/or bone degradation, arthritis, rheumatoid arthritis, pauciarticular rheumatoid arthritis, polyarticular rheumatoid arthritis, systemic onset rheumatoid arthritis, ankylosing spondylitis, enteropathic arthritis, reactive arthritis, SEA Syndrome (Seronegativity, Enthesopathy, Arthropathy Syndrome), dermatomyositis, psoriatic arthritis, scleroderma, systemic lupus erythematosus, vasculitis, myolitis, polymyolitis, dermatomyolitis, osteoarthritis, polyarteritis nodossa, Wegener's granulomatosis, arteritis, polymyalgia rheumatica, sarcoidosis, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease, ulcerative colitis, Crohn's disease, Celiac disease (nontropical Sprue), enteropathy associated with seronegative arthropathies, microscopic or collagenous colitis, eosinophilic gastroenteritis, or pouchitis resulting after proctocolectomy and ileoanal anastomosis, pancreatitis, insulin-dependent diabetes mellitus, mastitis, cholecystitis, cholangitis, pericholangitis, multiple sclerosis (MS), asthma (including extrinsic and intrinsic asthma as well as related chronic inflammatory conditions, or hyperresponsiveness, of the airways), chronic obstructive pulmonary disease (COPD. i.e., chronic bronchitis, emphysema), Acute Respiratory Disorder Syndrome (ARDS), respiratory distress syndrome, cystic fibrosis, pulmonary hypertension, pulmonary vasoconstriction, acute lung injury, allergic bronchopulmonary aspergillosis, hypersensitivity pneumonia, eosinophilic pneumonia, bronchitis, allergic bronchitis bronchiectasis, tuberculosis, hypersensitivity pneumonitis, occupational asthma, asthma-like disorders, sarcoid, reactive airway disease (or dysfunction) syndrome, byssinosis, interstitial lung disease, hyper-eosinophilic syndrome, rhinitis, sinusitis, and parasitic lung disease, airway hyperresponsiveness associated with viral-induced conditions (for example, respiratory syncytial virus (RSV), parainfluenza virus (PIV), rhinovirus (RV) and adenovirus), Guillain-Barre disease, Graves' disease, Addison's disease, Raynaud's phenomenon, autoimmune hepatitis, GVHD, and the like. TIMP-3 polypeptides, variants, muteins or derivatives also have application in cases where decreased relative levels of TIMP-3 (i.e., a decrease in the ratio of endogenous TIMP-3 to metalloproteases, which may be a result of decreased amounts of TIMP-3 or increased amounts of metalloproteases) are associated with pathological effects, for example, in myocardial ischemia, reperfusion injury, and during the progression to chronic heart failure.

Based on the ability of TIMP-3 to inhibit connective tissue degradation, TIMP-3 polypeptides, variants, muteins or derivatives have application in cases where inhibition of angiogenesis is useful, e.g., in preventing or retarding tumor development, and the prevention of the invasion of parasites. For example, in the field of tumor invasion and metastasis, the metastatic potential of some particular tumors correlates with the increased ability to synthesize and secrete collagenases, and with the inability to synthesize and secrete significant amounts of a metalloproteinase inhibitor. The presently disclosed TIMP-3 proteins also have therapeutic application in inhibiting tumor cell dissemination during removal of primary tumors, during chemotherapy and radiation therapy, during harvesting of contaminated bone marrow, and during shunting of carcinomatous ascites. Diagnostically, correlation between absence of TIMP-3 production in a tumor specimen and its metastatic potential is useful as a prognostic indicator as well as an indicator for possible prevention therapy.

MMPs also act on the basal lamina and tight junction proteins in the brain, as part of the pathway for opening the blood-brain barrier (BBB), facilitating the entrance of cells and soluble mediators of inflammation into the brain. Accordingly, the present compositions and methods are useful in the treatment of disorders of the nervous system characterized by excessive or inappropriate permeabilization of the BBB. Additionally, degradation of matrix proteins around neurons can result in loss of contact and cell death; thus, the disclosed TIMP-3 compositions may protect nerve cells from damage by preserving the basement membrane surrounding nerve cells. The inventive TIMP-3 compositions are useful in treating or ameliorating the neuroinflammatory response to injury, for example, cerebral ischemia, or for traumatic brain injury. The compositions disclosed herein will also be useful in the treatment of neurodegenerative diseases where inflammation is an underlying cause of the disease, for example, multiple sclerosis, as well as in treatment of various forms of neuropathy and/or myopathy, spinal cord injury, and amyotrophic lateral sclerosis (ALS). Accordingly, uses of the inventive compositions may involve co-administration with BDNF, NT-3, NGF, CNTF, NDF, SCF, or other nerve cell growth or proliferation modulation factors. In addition, the present compositions and methods may be applicable for cosmetic purposes, in that localized inhibition of connective tissue breakdown may alter the appearance of tissue.

TIMP-3 polypeptides, variants, muteins or derivatives may be employed in an in vitro procedure, or administered in vivo to augment endogenous TIMP-3 activity and/or enhance a TIMP-3-induced biological activity. The inventive TIMP-3 polypeptides, variants, muteins or derivative may be employed in vivo under circumstances in which endogenous TIMP-3 is downregulated or present at low levels. Disorders caused or exacerbated (directly or indirectly) by TIMP-3-inhibitable proteinases, examples of which are provided herein, thus may be treated. In one embodiment, the present invention provides a therapeutic method comprising in vivo administration of a TIMP-3 polypeptide, variant, mutein, or derivative or a nucleic acid encoding the TIMP3 polypeptide, variant, mutein, or derivative (for example, present in an expression vector, such as a viral vector (e.g., adenoviral, retroviral, or adeno-associated viral vector) to a mammal in need thereof in an amount effective for increasing a TIMP-3-induced biological activity. In another embodiment, the invention provides a therapeutic method comprising in vivo administration of a TIMP-3 polypeptide, variant, mutein or derivative to a mammal in need thereof in an amount effective for elevating endogenous levels of TIMP-3.

For example, the invention provides a method of treating a disorder, such as any one of the disorders described above, comprising administering to a subject in need thereof an amount of TIMP-3 variant, mutein or derivative effective to treat the disorder. The invention further provides use of the TIMP-3 variant, mutein or derivative described herein in the treatment of a disorder, such as any one of the disorders described above, as well as use of the TIMP-3 variant, mutein or derivative in the preparation of a medicament for the treatment of a disorder. It will be appreciated that "treating" and "treatment" refers to any reduction in the severity and/or onset of symptoms associated with a disorder. Any degree of protection from, or amelioration of, a disorder or symptom associated therewith is beneficial to a subject, such as a human patient.

Included in the invention is a method of inhibiting cardiac extracellular matrix (ECM) degradation and/or adverse remodeling, optionally associated myocardial infarction (e.g., acute myocardial infarction). The method comprises administering to a subject in need thereof a therapeutically effective amount of TIMP-3 variant, mutein or derivative, thereby inhibiting ECM degradation and/or adverse remodeling. Complete inhibition is not required in the context of the invention; any degree of reduction in ECM degradation and/or adverse cardiac remodeling is contemplated. ECM homeostasis is disrupted in the hours following infarction, causing ECM instability and adverse cardiac remodeling. Adverse cardiac remodeling results in structural and functional changes in the heart, such as ventricular wall thinning, left ventricular dilation (LV EDV increase), systolic and diastolic dysfunction (% ejection fraction (EF) decrease), infarct expansion and, ultimately, heart failure. Maintaining ECM homeostasis (in whole or in part) reduces the severity of tissue damage and improves cardiac function. Accordingly, the method in one aspect is performed as soon as possible after it has been determined that a subject is at risk for myocardial infarction (or any of the disorders described herein) or as soon as possible after myocardial infarction is detected. For example, in at least one embodiment, the TIMP-3 variant, mutein or derivative is administered within 1, 2, 3, 4, 5, 6, 7, 8, 12, or 24 hours of myocardial infarction. Optionally, administration of the TIMP-3 variant, mutein or derivative results in at least a 3%, at least a 5%, at least a 10%, or at least a 15% improvement in ejection fraction (compared to EF in a subject not administered the TIMP-3 variant, mutein or derivative) following myocardial infarction, and/or an improvement in cardiac output, and/or a reduction in left ventricular wall thinning, and/or increase or maintenance of end-systolic volume or end-diastolic volume.

In another aspect, the present invention provides TIMP-3 polypeptides, variants, muteins or derivatives having improved half-life in vivo. In one embodiment, the half-life of a TIMP-3 mutein is at least twice that of native TIMP-3; in another embodiment, the half-life is at least three times, four times, five times, six times, eight times or ten times greater than that of native TIMP-3. Alternatively or in addition, the TIMP-3 variant, mutein or derivative has a half-life that is at least 0.5 hours longer, at least 1 hour longer, at least 1.5 hour longer, at least 2 hours longer, at least 3 hours longer, at least 6 hours longer, at least 8 hours longer, at least 10 hours longer, at least 12 hours longer, or at least 24 hours longer than native TIMP-3 (e.g., SEQ ID NO: 2 or amino acids 1-144 of SEQ ID NO: 2). In one embodiment, the half-life is determined in a non-human mammal; in another embodiment, the half-life is determined in a human subject. In various embodiments, the TIMP-3 mutein, variant, or derivative has a half-life of at least two hours, at least three hours, at least four hours, at least five hours, or more, e.g., up to 24 hours, up to 18 hours, up to 13 hours, or up to 12 hours. Further embodiments provide a TIMP-3 mutein or variant that has a half-life of at least one day in vivo (e.g., when administered to a human subject). In one embodiment, the TIMP-3 polypeptides, variants, muteins or derivatives have a half-life of at least three days. In another embodiment, the TIMP-3 polypeptides, variants, muteins or derivatives have a half-life of four days or longer or five days or longer. In another embodiment, the TIMP-3 polypeptides, variants, muteins or derivatives have a half-life of eight days or longer. Systemic half-life can be measured (e.g., in plasma) or local, in situ half-life can be measured (e.g., in cardiac tissue or tissue adjacent to local administration sites).

In another embodiment, the TIMP-3 polypeptide, variants, or muteins is derivatized or modified such that it has a longer half-life as compared to the underivatized or unmodified TIMP-3 binding protein. The derivatized polypeptide can comprise any molecule or substance that imparts a desired property to the polypeptide, such as increased half-life in a particular use. The derivatized polypeptide can comprise, for example, a detectable (or labeling) moiety (e.g., a radioactive, colorimetric, antigenic or enzymatic molecule, a detectable bead (such as a magnetic or electro-dense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the polypeptide for a particular use (e.g., administration to a subject, such as a human subject, or other in vivo or in vitro uses).

In one such example, the polypeptide is derivatized with a ligand that specifically binds to articular cartilage tissues, for example as disclosed in WO2008063291 and/or Rothenfluh et al., Nature Materials 7:248 (2008). Examples of molecules that can be used to derivatize a polypeptide include albumin (e.g., human serum albumin) and polyethylene glycol (PEG). Albumin-linked and PEGylated derivatives of polypeptides can be prepared using techniques well known in the art. In one embodiment, the polypeptide is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols (US Pat. App. No. 20030195154).

Compositions

The invention includes pharmaceutical compositions comprising effective amounts of polypeptide products (i.e, TIMP-3 polypeptides, variants, muteins or derivatives) of the invention together with pharmaceutically acceptable diluents, preservatives, solubilizers, emulsifiers, adjuvants and/or carriers useful in TIMP-3 therapy (i.e., conditions in which increasing the endogenous levels of TIMP-3 or augmenting the activity of endogenous TIMP-3 are useful). Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); covalent attachment of polymers such as polyethylene glycol to the protein (as discussed supra, see, for example U.S. patent 4,179,337 hereby incorporated by reference); incorporation of the material into particulate preparations of polymeric compounds such as polylactic acid, polyglycolic acid, etc. or into liposomes. Such compositions will influence the physical state, stability, rate of in vivo release, and rate of in vivo clearance of TIMP-3 binding proteins. See, e.g., Remington's Pharmaceutical Sciences, 18th Ed. (1990, Mack Publishing Co., Easton, Pa. 18042) pages 1435-1712 which are herein incorporated by reference.

Generally, an effective amount of the present polypeptides will be determined by the age, weight and condition or severity of disease of the recipient. See, Remingtons Pharmaceutical Sciences, supra, at pages 697-773, herein incorporated by reference. Typically, a dosage of between about 0.001 g/kg body weight to about 1 g/kg body weight (or 1 mg-1000 mg), may be used, but more or less, as a skilled practitioner will recognize, may be used. For local (i.e., non-systemic) applications, such as topical or intra-articular applications, the dosing may be between about 0.001 g/cm$^2$ to about 1 g/cm$^2$. In the context of reducing or inhibiting ECM degradation and/or adverse cardiac tissue remodeling, a direct injection (or series of injections that constitute a single administration) into myocardium optionally comprises 1 mg-50 mg of TIMP-3 polypeptide (e.g., 3 mg-40 mg, 5 mg-30 mg, or 10 mg-25 mg). Dosing may be one or more times daily, or less frequently, and may be in conjunction with other compositions as described herein. An administration of TIMP-3 variant, mutein or derivative may be applied one, two, three, four, five, six, or seven days a week as needed. Alternatively, the TIMP-3 variant, mutein or derivative is administered once a week, once every two weeks, once every three weeks, or once every four weeks (once monthly). In various embodiments, the treatment regimen comprises a single administration of TIMP-3 polypeptide; for example, intervention following or during myocardial infarction may comprise a single administration directly into the heart, optionally during a surgical procedure. It should be noted that the present invention is not limited to the dosages recited herein.

As is understood in the pertinent field, pharmaceutical compositions comprising the molecules of the invention are administered to a subject in a manner appropriate to the indication. Pharmaceutical compositions may be administered by any suitable technique, including but not limited to parenterally, topically, locally or by inhalation. If injected, the pharmaceutical composition can be administered, for example, via intravenous, intramuscular, intralesional, intraperitoneal or subcutaneous routes, by bolus injection, or continuous infusion.

Localized administration, e.g., at a site of disease or injury is contemplated, as are transdermal delivery and sustained release from implants or patches. Other alternatives include eyedrops; oral preparations including pills, syrups, lozenges or chewing gum; and topical preparations such as lotions, gels, sprays, and ointments. For example, localized administration to joints or the musculoskeletal systems includes periarticular, intra-articular, intrabursal, intracartilaginous, intrasynovial and intratendinous administration. Administration to the respiratory system includes intrapulmonary, intraplural, intrapulmonary, intratracheal, intrasinal and intrabronchial delivery, and can be facilitated, for example, by an inhaler or a nebulizer. Intrathecal delivery and other methods that are useful to introduce compositions into the brain and/or nervous system are also contemplated herein, for example, epidural, intradural or peridural, administration, as well as perineural, intracaudal, intracerebral, intracisternal, and intraspinal administration.

Further examples of local administration include delivery to tissue in conjunction with surgery or another medical procedure. For example, a pharmaceutical composition of the invention can be administered to heart tissue during surgery that is performed to treat or ameliorate cardiac symptoms, or during a procedure such as cardiac catheterization (for example, percutaneous coronary intervention or angioplasty). Delivery may be via intracoronary, intracardial, intramyocardial, epicardial, and/or transendocardial route, for example, and may be guided by endocardial angiography or electromechanical maps of the area of the heart to be injected, or by the use of other techniques, such as magnetic resonance imaging (MRI). Compositions can also be delivered via inclusion in a cardiac patch, intracoronary catheter or in the coating of a stent or other device useful in cardiac conditions. An example of a suitable delivery device is described in U.S. Provisional Patent Application No. 62/037,743, filed Aug. 15, 2014, which is hereby incorporated by reference in its entirety.

In addition to eye drops, the use of ointments, creams or gels to administer the present compositions to the eye is also contemplated. Direct administration to the interior of the eye may be accomplished by periocular, conjunctival, intracorneal, subconjunctival, subtenons, retrobulbar, intraocular, and/or intravitreal injection or administration. These and other techniques are discussed, for example, in Gibaldi's Drug Delivery Systems in Pharmaceutical Care (2007, American Society of Healthe-Sytem Pharmacists, Bethesda, Md.).

A plurality of agents act in concert in order to maintain the dynamic equilibrium of the extracellular matrix and tissues. In treatment of conditions where the equilibrium is skewed, one or more of the other agents may be used in conjunction with the present polypeptides. These other agents may be co-administered or administered in seriatim, or a combination thereof. Generally, these other agents may be selected from the list consisting of the metalloproteinases, serine proteases, inhibitors of matrix degrading enzymes, intracellular enzymes, cell adhesion modulators, and factors regulating the expression of extracellular matrix degrading proteinases and their inhibitors. While specific examples are listed below, one skilled in the art will recognize other agents performing equivalent functions, including additional agents, or other forms of the listed agents (such as those produced synthetically, via recombinant DNA techniques, and analogs and derivatives).

Other degradation inhibitors may also be used if increased or more specific prevention of extracellular matrix degradation is desired. Inhibitors may be selected from the group consisting of alpha$_2$ macroglobulin, pregnancy zone protein, ovostatin, alpha$_1$-proteinase inhibitor, alpha$_2$-antiplasmin, aprotinin, protease nexin-1, plasminogen activator inhibitor (PAI)-1, PAI-2, TIMP-1, TIMP-2, and TIMP-4. Others may be used, as one skilled in the art will recognize.

Intracellular enzymes may also be used in conjunction with the present polypeptides. Intracellular enzymes also may affect extracellular matrix degradation, and include lysozomal enzymes, glycosidases and cathepsins.

Cell adhesion modulators may also be used in combination with the present polypeptides. For example, one may wish to modulate cell adhesion to the extracellular matrix prior to, during, or after inhibition of degradation of the extracellular matrix using the present polypeptides. Cells which have exhibited cell adhesion to the extracellular matrix include osteoclasts, macrophages, neutrophils, eosinophils, killer T cells and mast cells. Cell adhesion modulators include peptides containing an "RGD" motif or analog or mimetic antagonists or agonists.

Factors regulating expression of extracellular matrix degrading proteinases and their inhibitors include cytokines, such as IL-1 and TNF-alpha, TGF-beta, glucocorticoids, and retinoids. Other growth factors effecting cell proliferation and/or differentiation may also be used if the desired effect is to inhibit degradation of the extracellular matrix using the present polypeptides, in conjunction with such cellular effects. For example, during inflammation, one may desire the maintenance of the extracellular matrix (via inhibition of enzymatic activity) yet desire the production of neutrophils; therefore one may administer G-CSF. Other factors include erythropoietin, interleukin family members, SCF, M-CSF, IGF-I, IGF-II, EGF, FGF family members such as KGF, PDGF, and others. One may wish additionally the activity of interferons, such as interferon alpha's, beta's, gamma's, or consensus interferon. Intracellular agents include G-proteins, protein kinase C and inositol phosphatases. The use of the present polypeptides may provide therapeutic benefit with one or more agents involved in inflammation therapy.

Cell trafficking agents may also be used. For example, inflammation involves the degradation of the extracellular matrix, and the movement, or trafficking of cells to the site of injury. Prevention of degradation of the extracellular matrix may prevent such cell trafficking. Use of the present polypeptides in conjunction with agonists or antagonists of cell trafficking-modulation agents may therefore be desired in treating inflammation. Cell trafficking-modulating agents may be selected from the list consisting of endothelial cell surface receptors (such as E-selectins and integrins); leukocyte cell surface receptors (L-selectins); chemokines and chemoattractants. For a review of compositions involved in inflammation, see Carlos et al., Immunol. Rev. 114: 5-28 (1990), which is herein incorporated by reference.

Moreover, compositions may include neu differentiation factor, "NDF," and methods of treatment may include the administration of NDF before, simultaneously with, or after the administration of TIMP-3. NDF has been found to stimulate the production of TIMP-2, and the combination of NDF, TIMP-1, -2 and/or -3 may provide benefits in treating tumors.

Polypeptides of the invention may be "labeled" by association with a detectable marker substance (e.g., radiolabeled with $^{125}$I, or labeled with a fluorophore such as AlexaFluor® [LifeTechnologies, Grand Island N.Y.]) or IR dyes [DyLight 800 NHS ester, Thermo Scientific] to provide reagents useful in detection and quantification of TIMP-3 in solid tissue and fluid samples such as blood or urine. Nucleic acid products of the invention may also be labeled with detectable markers (such as radiolabels and non-isotopic labels such as biotin) and employed in hybridization processes to identify relevant genes, for example.

As described above, the present TIMP-3 polypeptide, variant, mutein or derivative compositions have wide application in a variety of disorders. Thus, another embodiment contemplated herein is a kit including the present compositions and optionally one or more of the additional compositions described above for the treatment of a disorder involving the degradation of extracellular matrix. An additional embodiment is an article of manufacture comprising a packaging material and a pharmaceutical agent within said packaging material, wherein said pharmaceutical agent contains the present polypeptide(s), variant(s), mutein(s) or derivative(s) and wherein said packaging material comprises a label which indicates a therapeutic use for TIMP-3. In some aspects, the article of manufacture comprises TIMP-3 polypeptide, variant, mutein or derivative in a desired amount (e.g., 1-1000 mg, 1-100 mg, 1-50 mg, or any of the other amounts disclosed herein). In one embodiment, the pharmaceutical agent may be used for an indication selected from the group consisting of: cancer, inflammation, arthritis (including osteoarthritis and the like), dystrophic epidermolysis bullosa, periodontal disease, ulceration, emphysema, bone disorders, scleroderma, wound healing, erythrocyte deficiencies, cosmetic tissue reconstruction, fertilization or embryo implant modulation, and nerve cell disorders. This article of manufacture may optionally include other compositions or label descriptions of other compositions.

The following examples are provided for the purpose of illustrating specific embodiments or features of the instant invention and do not limit its scope.

EXAMPLES

Example 1:

This Example describes a method used to determine the effects, if any, of a mutation or mutations in TIMP-3 on expression in a mammalian expression system. This Example describes a general vector and host cell system, numerous vector and host cell systems are known in the art, described herein, and are suitable for determination of the effects, if any, of particular mutations in a TIMP-3 sequence on the expression of recombinant protein.

In general, a TIMP-3-encoding DNA is ligated into an expression vector under conventional conditions (i.e, the TIMP-3 encoding DNA is operably linked to other sequences in the vector so as to be expressible), and suitable mammalian cells are transformed or transfected with the vector. The transformed or transfected cells are cultured under appropriate conditions, and the recombinant protein is expressed and the amount evaluated, either qualitatively/semi-quantitatively, for example by Western blot or SDS=PAGE, or more quantitatively using an assay such as an ELSA (R&D Systems, Minneapolis Minn.) or ForteBio Octet® (Pall ForteBio Corp, Menlo Park, Calif.) In this manner, the effects of various mutations on the ability of mammalian cells to express a TIMP-3 protein, mutein or variant can be determined.

If the mutation or mutations were made to introduce N-linked glycosylation sites into a TIMP-3 polypeptide, or to enhance the native glycosylation site, it may be desirable to evaluate the presence and/or degree of glycosylation. Cells are transformed or transfected as described previously and semi-quantitative measures (e.g. western blots) can be used to determine if N-linked glycosylation was not successfully incorporated, partially incorporated, or fully incorporated.

Example 2:

This Example describes a method used to determine whether a mutation or mutations in TIMP-3 resulted in increased heparin independence. Cells are transformed or transfected and cultured in the presence or absence of heparin. The heparin can be added in varying amounts, to develop a semi-quantitative notion of the degree of heparin dependence. The amounts of TIMP-3 protein, mutein or variant expressed under various conditions is then determined, and a comparison is made to determine whether a particular mutation has any effect on whether or not heparin is required for release of the TIMP-3 protein, mutein or variant from the extracellular matrix, or whether the amount or heparin required is reduced.

Figure 3:
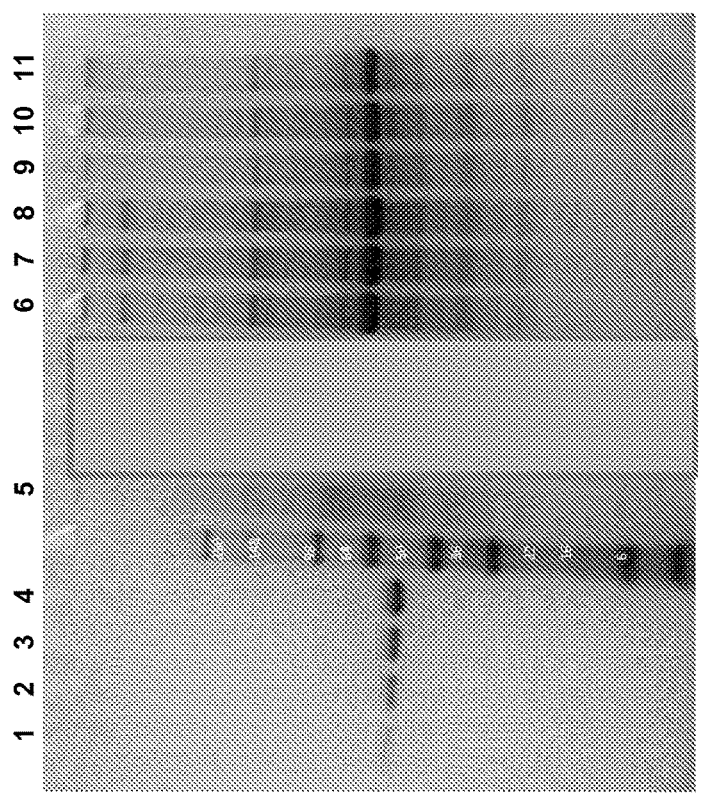
FIG. 3 is a reproduction of an SDS-PAGE gel illustrating the amount of a native N-TIMP-3 fused to human serum albumin (HSA) produced in the presence and absence of heparin. Lane #1-4 contained Fc standards ("STD"): Lane #1 contained 100 ng human Fc; Lane #2 contained 250 ng human Fc; Lane #3 contained 500 ng human Fc; and Lane #4 contained 1000 ng human Fc. Lane #5 represented a host cell control sample. Lanes #6-11 contained 10 µL samples from different pools of culture media of CHOK1-expressing TIMP-3-HSA: Pool 1 cultured with heparin (Lane #6), Pool 2 cultured with heparin (Lane #7), Pool 3 cultured with heparin (Lane #8), Pool 1 cultured without ("wo") heparin (Lane #9), Pool 2 cultured without heparin (Lane #10), Pool 3 cultured without heparin (Lane #11).
Figure 4:
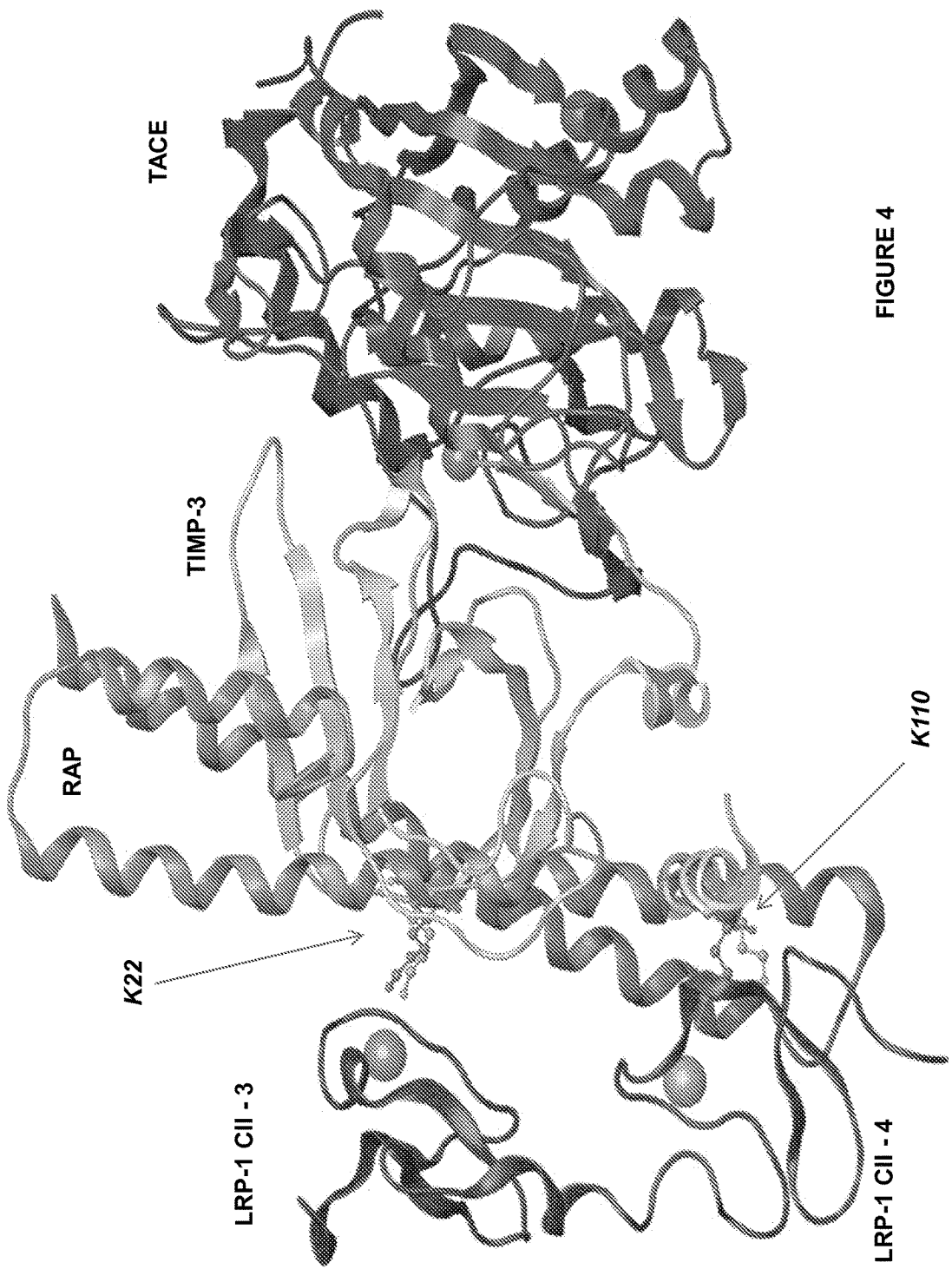
FIG. 4 is an illustration of the three dimensional structure of TIMP-3 associated with TACE, RAP, and LPR-1. TIMP-3 lysines at positions 22 and 110 are labeled. See also Wisniewska et al., J. Mol. Biol., 381, 1307-1319 (2008).

Using the method described above, the heparin dependence of various TIMP-3 muteins was determined. CHOK1 cells were stably transfected (selected with puromycin) to produce TIMP-3 or TIMP-3 muteins. When cell viability reached greater than 90%, the cells were seeded into a production media and cultured in the presence or absence of heparin (up to 500 ug/mL) for six days. The amounts of TIMP-3 protein was determined via SDS-PAGE (4-20% Tris-Glycine; Non-reduced+Iodoacetamide). Representative data is illustrated in FIGS. 1-3.

In the absence of heparin, expression of a fusion protein comprising an TIMP-3 fragment fused to an Fc was not detected in culture media. FIG. 1, Lane 5. As the amount of heparin supplied to the culture media increased, the amount of fusion protein detected in the culture media correspondingly increased. FIG. 1, Lanes 6-9.

Introduction of glycosylation sites affected heparin dependence of TIMP-3 muteins. TIMP-3 variants [H78N/Q80T/K94N/E96T/D110N/K112T/R138T] and [K45N/V47T/K94N/E96T/D110N/K112T/G173T] fused to an Fc were produced in CHOK1 cells in the absence of heparin. Expression of the TIMP-3 muteins was detected after six days of incubation, indicating a reduced dependence on heparin. Compare FIG. 2 with FIG. 1. The expression estimates in mg/mL (ForteBio Protein A) are set forth in Table 1.

TABLE 1

| TIMP-3 Mutein | Lane | Expression Estimate | SEQ ID NO: |
|---|---|---|---|
| [K45N/V47T/K94N/E96T/D110N/K112T/G173T]-FcG1 | 6 | 95 | 76 |
| [K45N/V47T/K94N/E96T/D110N/K112T/G173T]-IgG1Fc + EPKSS fusion | 7 | 89 | 77 |
| [H78N/Q80T/K94N/E96T/D110N/K112T/R138T]-FcG1 | 8 | 113 | 78 |
| [H78N/Q80T/K94N/E96T/D110N/K112T/R138T]-IgG1Fc + EPKSS fusion | 9 | 117 | 79 |

Heparin dependence is also affected by the choice of fusion partner. Unlike the Fc fusion, fusion of a native TIMP-3 fragment (AA 1-144) to human serum albumin (HSA) reduced the dependence on heparin. FIG. 3 illustrates the robust expression of the N-TIMP-3-HSA fusion. Similarly, fusion of TIMP-3 variant [F57N/K45S] to HSA resulted in strong expression of the protein in the absence of heparin, whereas fusion to Fc (instead of HSA) did not abrogate heparin dependence.

This Example demonstrates that TIMP-3 muteins described herein exhibit reduced dependence on heparin for production in culture media.

Example 3:

This Example describes MMP Inhibition Assays in which MMP activity is measured by using fluorimetric methods; other methods are known in the art. For example, fluorescence signal is increased upon cleaving a quenched MMP subtype 5-FAM/QXL 520 fluorescence resonance energy transfer (FRET) peptide substrate by an activated MMP subtype or subtype specific catalytic domain. FRET peptides are available for a number of different MMP, for example, from Anaspec (Fremont, Calif.) or R&D Systems (Minneapolis, Minn.). The TIMP-3 proteins used herein may be either nativeTIMP-3 or TIMP-3 mutein, variant or derivative; the proteins to be tested are referred to as test molecules.

For MMP2 activity assay, human pro-MMP2 (Anaspec, Fremont, Calif.) is activated with 1 mM 4-aminophenylmercuric acetate (APMA, Anaspec, Fremont, Calif.) for 1 hour at 37° C. before incubating with MMP2 sensitive 5-FAM/QXL 520 FRET peptide in assay buffer provided by the vendor against various concentrations of test molecules in a black 384-well Optiplate (Perkin Elmer, Waltham, Mass.) at 37° C. After 2 hours of incubation, fluorescence signal from the reaction plate is measured at excitation (490 nm) and emission (520 nm) on EnVision multilabel microplate reader (PerkinElmer, Waltham, Mass.). Data in relative fluorescence unit (RFU) is plotted against tested test molecule concentrations in GraphPad Prism 5.0 (GraphPad, San Diego, Calif.) to estimate half maximal inhibition constant (IC50).

For MMP9 activity measurement, a catalytic domain of human MMP9 (Anaspec, Fremont, Calif.) is incubated with MMP9 sensitive 5-FAM/QXL 520 FRET peptide and various concentrations of test molecules in a black 384-well Optiplate (Perkin Elmer, Waltham, Mass.) at 37° C. After 2 hours of incubation, fluorescence signal is measured at excitation (490 nm) and emission (520 nm) on EnVision multilabel microplate reader (PerkinElmer, Waltham, Mass.). Data in relative fluorescence unit (RFU) is plotted against tested test molecule concentrations in GraphPad Prism 5.0 (GraphPad, San Diego, Calif.) to estimate half maximal inhibition constant (IC50).

For MMP13 activity, test molecules are titrated in assay buffer (20 mM Tris, 10 mM $CaCl_2$, 10uM $ZnCl_2$, 0.01% Brij 35 (Calbiochem/EMD, San Diego, Calif.), pH 7.5) and added to black polystyrene 96 or 384 well assay plate (Griener Bio-One, Germany). Active MMP13 (Calbiochem/EMD) is diluted in assay buffer and added to the test molecule titration and incubated for 10 minutes at room temperature in a final volume of 50 microL. Alternatively, pro-MMP-13 (R & D Systems, Minneapolis, Minn.) is activated with APMA for 2 hours at 37 degrees C., and used in the assay. A fluorogenic substrate such as Mca-PLGL-Dpa-AR-NH2 Fluorogenic MMP Substrate or Mca-KPLGL-Dpa-AR-NH2 Fluorogenic Peptide Substrate (R & D Systems) is prepared, and added to the MMP-13 enzyme/huTIMP-3/test molecule solution. MMP-13 activity is measured kinetically, for example for 20 minutes using Molecular Devices fluorescent plate reader (or equivalent).

The effect of the molecules being tested may be expressed as percent of expected maximum TIMP-3 inhibition of MMP enzymatic activity. Alternatively, a quantitative evaluation of MMP inhibitory activity may not be necessary; rather, individual test molecules can be evaluated as to whether they inhibit MMP or not. Those of ordinary skill in the art recognize that the parameters outlined herein can be varied by the application of routine experimentation. For example, preliminary experiments are performed using previously tested TIMP-3 and other materials to determine an appropriate concentration of an MMP or pro-MPP. Similarly, the type and appropriate concentration of substrate can also be determined. Thus, for example, MMP can be titrated and compared to a previously tested batch of MMP to optimize the assay parameters. Additionally, those of ordinary skill in the art can utilize similar assays to evaluate the effects, if any, or various TIMP-3 mutations on ability to of a TIMP-3 mutein or variant to inhibit other MMPs including TNF alpha converting enzyme (TACE).

Example 4:

Using standard techniques of molecular biology, nucleic acids encoding numerous muteins of TIMP-3 were prepared and expressed in mammalian cells, substantially as described previously. The effects of the mutations on the expression of the encoded TIMP-3 muteins were evaluated. The listing of mutations made includes K45N; V47T; K50N; V52T; P56N; F57N; G58T; H78N; Q80T; K94N; E96T; D110N; K112T; R138T; G173T; and combinations thereof This Table summarizes expression and MMP inhibition results obtained with numerous TIMP-3 muteins that did express in mammalian cells. The increase in the level of expression demonstrating the fold increase in expression as compared to that observed for wild-type TIMP-3 is determined either qualitatively through the use of western blots or SDS-PAGE Coomassie stained gels, or through the measurement of expression titers as measured using a ForteBio Octet® readout using an anti TIMP-3 antibody to capture TIMP-3 (such antibodies are publicly available, for example from EMD Millipore, Billerica, Mass.: AbCam®, Cambridge, Mass.:, or R&D Systems, Minneapolis, Minn.).

TABLE 2

| Variant | # EG | HI | Titer | MMP2 | MMP9 | TACE |
|---|---|---|---|---|---|---|
| K45N, V47T, P56N, G58T, Q126N, R138T (SEQ ID NO: 3) | 4 | no | + | nd | nd | nd |
| K45N, V47T, P56N, G58T, K94N, E96T, R138T (SEQ ID NO: 4) | 4 | Yes | ++++ | 1 | 9 | none |
| K45N, V47T, P56N, G58T, R138T, G173T (SEQ ID NO: 5) | 4 | nd | – | nd | nd | nd |
| K45N, V47T, F57N, K94N, E96T, D110N, K112T (SEQ ID NO: 6) | 4 | Yes | +++ | 2 | 59 | none |
| K45N, V47T, F57N, K94N, E96T, R138T (SEQ ID NO: 7) | 4 | Yes | +++ | 2 | 38 | none |
| K45N, V47T, H78N, Q80T, K94N, E96T, R138T, G173T (SEQ ID NO: 8) | 5 | nd | – | nd | nd | nd |
| K45N, V47T, K94N, E96T, D110N, K112T, R138T (SEQ ID NO: 9) | 4 | nd | – | nd | nd | nd |
| K45N, V47T, K94N, E96T, D110N, K112T, G173T (SEQ ID NO: 10) | 4 | Yes | +++ | 2 | 9 | 2 |
| K45N, V47T, K94N, E96T, R138T, G173T (SEQ ID NO: 11) | 4 | no | + | nd | nd | nd |
| K45S, F57N, K94N, E96T, D110N, K112T, R138T (SEQ ID NO: 12) | 4 | No | +++ | 3 | 74 | none |
| K45S, F57N, H78N, Q80T, K94N, E96T, R138T (SEQ ID NO: 13) | 4 | no | + | nd | nd | nd |
| K50N, V52T P56N, G58T, K94N, E96T, D110N, K112T, R138T (SEQ ID NO: 14) | 5 | Yes | +++ | 2 | 19 | none |
| K50N, V52T, H78N, Q80T, K94N, E96T, R138T, G173T (SEQ ID NO: 15) | 5 | yes | + | nd | nd | nd |
| K50N, V52T, K94N, E96T, D110N, K112T, R138T (SEQ ID NO: 16) | 4 | Partial | +++ | 3 | 10 | 0.6 |
| K50N, V52T, K94N, E96T, D110N, K112T, R138T, G173T (SEQ ID NO: 17) | 5 | Partial | +++ | 5 | 21 | 2 |
| K50N, V52T, K94N, E96T, R138T, G173T (SEQ ID NO: 18) | 4 | no | + | nd | nd | nd |
| K50N, V52T, Q126N, R138T, G173T (SEQ ID NO: 19) | 4 | no | + | nd | nd | nd |
| P56N, G58T, H78N, Q80T, K94N, E96T, R138T (SEQ ID NO: 20) | 4 | Partial | ++++ | 2 | 15 | none |
| P56N, G58T K94N, E96T, Q126N, R138T (SEQ ID NO: 21) | 4 | Yes | ++++ | 2 | 22 | none |
| P56N, G58T, K94N, E96T, D110N, K112T, R138T (SEQ ID NO: 22) | 4 | Yes | ++++ | 2 | 20 | none |
| P56N, G58T, H78N, Q80T, K94N, E96T, G173T (SEQ ID NO: 23) | 4 | nd | – | nd | nd | nd |
| P56N, G58T, Q126N, R138T, G173T (SEQ ID NO: 24) | 4 | no | + | nd | nd | nd |
| H78N, Q80T, K94N, E96T, R138T, G173T (SEQ ID NO: 25) | 4 | nd | – | nd | nd | nd |
| H78N, Q80T, K94N, E96T, D110N, K112T, R138T (SEQ ID NO: 26) | 4 | Yes | +++ | 2 | 6 | 0.4 |

1: "# EG" = number of engineered glycosylation sites

2: "HI" indicates heparin independence, 'Yes,' ;No,' or 'Partial' as described in the Example 3: "Titer" refers to relative titer as compared to wild-type: '+': 1-10 mg/L, '++': 10-25 mg/L, '+++' 50-100 mg/L, '++++' >100 mg/L 4: "MMP2" lists the shift in MMP2 inhibitory activity (i.e., fold decrease) as compared to wild-type 5: "MMP9" lists the shift in MMP9 inhibitory activity (i.e., fold decrease) as compared to wild-type 6: "TACE" lists the shift in TACE inhibitory activity (i.e., fold decrease) as compared to wild-type nd = no data Additional studies were conducted to characterize fusion proteins of the invention using the methods described herein. TIMP-3 [H78N, Q80T, K94N, E96T, D110N, K112T, R138T] (SEQ ID NO:26) inhibited MMP2 and MMP9 ($EC_{50}$ of 1 nM and 2.5 nM, respectively). TIMP-3 [H78N, Q80T, K94N, E96T, D110N, K112T, R138T] (SEQ ID NO:26) fused to HSA, Fc, and IgG maintained inhibitory activity: HSA fusion, MMP2 $EC_{50}$=1.4 nM, MMP9 $EC_{50}$=5.1 nM; Fc fusion, MMP2 $EC_{50}$=13.3 nM, MMP9 $EC_{50}$=32.9 nM; IgG fusion, MMP2 $EC_{50}$=14 nM, MMP9 $EC_{50}$=26 nM. For comparison, N-TIMP3 exhibited MMP2 $EC_{50}$=7.6 nM, MMP9 $EC_{50}$=1.7 nM. Fusion of HSA to N-TIMP3 resulted in MMP2 $EC_{50}$=38.7 nM, MMP9 $EC_{50}$=36.5 nM, and fusion of Fc resulted in MMP2 $EC_{50}$=6.9 nM, MMP9 $EC_{50}$=1.6 nM.

Additional muteins are described, including those shown in Table 3 below. In the Table, particular mutations are listed in the heading; an "x" below a particular heading indicates that that mutation is present. The heading "#Gly" indicates the number of engineered glycosylation sites, and the heading "Designation" indicates the combination of mutations contemplated. These muteins can be made and tested as described herein.

TABLE 3

| K45N, V47T | K50N, V52T | H78N, Q80T | K94N, E96T | D110N K112T | R138T | G173T | #Glyc | Designation |
|---|---|---|---|---|---|---|---|---|
|  | x |  |  | x | x | x | 4 | K50N/V52T, D110N/K112T, R138T, G173T |
| x |  |  |  | x | x | x | 4 | K45N/V47T, D110N/K112T, R138T, G173T |
|  |  | x |  | x | x | x | 4 | H78N/Q80T, D110N/K112T, R138T, G173T |
| x | x | x |  |  | x |  | 4 | K45N/V47T, K50N/V52T, H78N/A80T, R138T |
| x |  | x |  | x |  | x | 4 | K45N/V47T, H78N/Q80T D110N/K112T, G173T |
| x |  | x |  |  | x | x | 4 | K45N/V47T, H78N/Q80T, R138T, G173T |
|  | x | x | x |  | x |  | 4 | K50N/V52T, H78N/Q80T K94N/E96T, G173T |
|  | x | x |  | x | x |  | 4 | K50N/V52T, H78N/Q80T D110N/K112T, R138T |
| x | x | x |  | x |  |  | 4 | K45N/V47T, K50N/V52T, H78N/Q80T, D110N/K112T |
|  | x |  |  | x | x | x | 4 | K50N/V52T, H78N/Q80T, R138T, G173T |
| x |  | x |  |  | x | x | 4 | K45N/V47T, H78N/Q80T, R138T, G173T |
| x |  | x |  | x | x |  | 4 | K45N/V47T, H78N/Q80T, D110N/K112T, R138T |
| x | x | x |  | x |  | x | 5 | K45N/V47T, K50N/V52T, H78N/Q80T, D110N/K112T, G173T |
| x | x | x |  |  | x | x | 5 | K45N/V47T, K50N/V52T, H78N/Q80T, R138T, G173T |
| x | x | x | x |  |  | x | 5 | K45N/V47T, K50N/V52T, H78N/Q80T, K94N/E96T, G173T |
| x |  | x | x |  | x | x | 5 | K45N/V47T, H78N/Q80T, K94N/E96T, R138T, G173T |
|  | x | x | x |  | x | x | 5 | K50N/V52T, H78N/Q80T, K94N/E96T, R138T, G173T |
| x |  | x |  | x | x | x | 5 | K45N/V47T, H78N/Q80T, D110N/K112T, R138T, G173T |
|  | x | x |  | x | x | x | 5 | K50N/V52T, H78N/Q80T, D110N/K112T, R138T, G173T |
| x | x | x |  | x | x |  | 5 | K45N/V52T, K50N/V52T, H78N/Q80T, D110N/K112T, R138T |

Example 5:

This Example describes an assay to evaluate the ability of a TIMP-3 protein to bind to HTB-94™ cells (a chondrocytic cell line available from the American Type Culture Collection, Manassas, Va.) by fluorescence activated cell sorter (FACS) analysis. HTB-94™ cells express high levels of LRP1 and ECM protein and are useful for monitoring TIMP-3 mutein binding to cells. HTB-94 cells are cultured in HTB-94 culture medium (high-glucose DMEM containing 10% fetal bovine serum [FBS] and 2 mM L Glutamine) at 37 C in 5% $CO_2$. Cells are seeded at a cell density of $2.5 \times 10^4$ cells/ml in standard tissue culture flasks for 6-12 weeks prior to staining and are passaged every 3-4 days after removal from flask via trypsinization. Approximately 16 hours prior to FACS stain, HTB-94 cells are seeded at 100,000 cells per well onto standard tissue culture 12-well plates in 2 ml volume HTB94 medium and incubated at 37 C in 5% $CO_2$. Cell are 80-90% confluent prior to stain.

After approximately 16 hours, the HTB94 culture medium is removed from the 12-well plates by aspiration and 1 ml 4 C stain buffer (phosphate buffered saline [PBS] 2% FBS 0.15% $NaN_3$) is applied per well. Cell plates are incubated 1 h on ice. Stain buffer is aspirated and TIMP-3 HIS-Myc tagged proteins (either native TIMP-3 or TIMP-3 variant) diluted in stain buffer to 80 microg/ml is added, 0.9 ml/well; the same volume of buffer only is added to a negative control well. Cell plates are incubated 30 min on ice, aspirated and washed twice with 1 ml/well stain buffer. After the second wash buffer is aspirated, and mouse anti-pentaHIS AlexaFluor488 conjugated antibody (Qiagen, Valencia, Calif.) diluted in stain buffer to 20 ug/ml is added, 0.9 mL/well. In parallel, irrelevant $mlgG_1$ AlexaFluor488 conjugated antibody (eBioscience, San Diego, Calif.) negative control stain reagent diluted in stain buffer to 20 microg/ml is added in parallel to a replicate well stained with known binder TIMP3 HIS-Myc (for example, K45S, F57N, SEQ ID NO:23).

Cell plates are incubated 30 min on ice while protected from light, aspirated and washed twice with 1 ml/well stain buffer. After the second wash buffer is aspirated, 1 mL per well cell-dissociation buffer (enzyme-free, PBS, catalog # 13151-014; Life Technologies, Grand Island N.Y.) is added. Cell plates are incubated 5min at 37 C, and cells are transferred to 4 ml FACS tubes. Plate wells are rinsed with 1 ml/well 25 C PBS and the rinses are added to corresponding FACS tubes containing cells in cell dissociation buffer. Tubes are centrifuged 5 min at 1000 RPM to form a cell pellet, and aspirated. Cells are resuspended in 300 microL 4% paraformaldehyde in PBS (PFA) and may be stored at 4 C protected from light until run on FACS.

Within two days of TIMP3 staining, 8000 fixed HTB94 cell events are acquired, for example on a Becton Dickinson FACS Calibur using FL1 for detecting AlexaFluor488 fluorescence. The forward scatter (FSC) detector's voltage is set at E00, and the side-scatter (SSC) detector's voltage is set at 316. Used in combination, these detectors measure light reflected off of cells as 'forward scatter' and 'side scatter,' which allows for the HTB-94 cell gate to be defined, also referred to as 'gated', and separated from non-cell material in the tube based on cell size and granularity. The FL1 detector's voltage is set at 370. Analysis is done, for example, using FlowJo vX.0.6.

Using the methods described above, it was determined that TIMP-3 [K45N, V47T, K94N, E96T, D110N, K112T, G173T] (SEQ ID NO:10) only weakly bound HTB-94™ cells, and TIMP-3 [K45S, F57N, K94N, E96T, D110N, K112T, R138T] (SEQ ID NO:12), TIMP-3 [K50N, V52T, K94N, E96T, D110N, K112T, R138T] (SEQ ID NO:16), TIMP-3 [P56N, G58T, K94N, E96T, D110N, K112T, R138T] (SEQ ID NO:22), and TIMP-3 [H78N, Q80T, K94N, E96T, D110N, K112T, R138T] (SEQ ID NO:26) did not bind HTB-94™ cells.

It was also determined that TIMP-3 [H78N, Q80T, K94N, E96T, D110N, K112T, R138T] (SEQ ID NO:26) does not bind LRP1. Reduced binding to components of the extracellular matrix (as indicated by reduced binding to HTB-94 cells) and LRP-1 scavenger proteins simplifies production by reducing reliance on heparin, improves yield, and increases availability of the molecule in vivo, all of which address complications in TIMP-3 production and therapy suffered by prior TIMP-3 polypeptides. Thus, the TIMP-3 muteins described herein provide unique advantages over previously identified TIMP-3 polypeptides.

Example 6:

This Example describes pharmacokinetic properties of TIMP-3 muteins described herein.

Sprague Darley rats with jugular vein cannulation (200 g-300 g, Charles River Labs, San Diego, Calif.) were anesthetized with 5% isofluorine before administering with TIMP-3 proteins (3-6 mg/kg) through the jugular vein. Blood samples (0.2 mL) were collected at each desired time point from 5 minutes to 72 hours in EDTA-treated syringe tubes and centrifuged for serum and blood cell separation. The collected serum samples were analyzed by either immunoassays in Gyros (Gyrolabs, Uppsala, Sweden) with TIMP-3 specific monoclonal antibody (10A7, Amgen) as capture antibody and anti-penta histidine antibody (Qiagen, Alameda, Calif.) or anti-Fc antibody (Amgen) as detection antibody. Additionally, TIMP-3 specific fragment was quantified via LC-MS/MS method. Serum samples (25 μL) were incubated with TIMP-3-specific 10A7 capture antibody before trypsin digestion at 37° C. overnight. TIMP-3 signature peptide fragments (WDQLTLSQR and TQYLLTGR) were quantified by extrapolating from standard curves generated with the peptides.

TABLE 4

| TIMP-3 polypeptide | Clearance (mL/hr/kg) | Half-life ($t_{1/2}$, hr) | Vss (mL/kg) |
| --- | --- | --- | --- |
| TIMP-3 [H78N, Q80T, K94N, E96T, D110N, K112T, R138T] | 48 ± 3 | 3.8 ± 0.2 | 134 ± 16 |
| TIMP-3 [K45S, F57N] | 189 ± 23 | 1.1 ± 0.1 | 71 ± 7 |
| TIMP-3 [K45S, F57N]-hetero Fc fusion | 45 ± 0 | 13.6 ± 3.5 | 208 ± 20 |

Introduction of N-linked glycosylation sites increased half-life and Vss and reduced clearance of TIMP-3 muteins. TIMP-3 [H78N, Q80T, K94N, E96T, D110N, K112T, R138T] (SEQ ID NO: 26) demonstrated substantially improved pharmacokinetic properties compared to TIMP-3 [K45S, F57N], having fewer N-linked glycosylation sites. Fusion of a half-life extension moiety (a hetero Fc fusion) to TIMP-3 [K45S, F57N] substantially improved pharmacokinetics properties compared to TIMP-3 [K45S, F57N] lacking the Fc portion.

Systemic half-life was also determined for TIMP-3 [K45N, V47T, P56N, G58T, K94N, E96T, R138T] (SEQ ID NO:4) (2.7 hours), TIMP-3 [K50N, V52T, K94N, E96T, D110N, K112T, R138T, G173T] (SEQ ID NO:17) (2 hours), TIMP-3 [K45N, V47T, K94N, E96T, D110N, K112T, G173T] (SEQ ID NO:10) (1.4 hours), and TIMP-3 [K50N, V52T, K94N, E96T, D110N, K112T, R138T] (SEQ ID NO:16) (2 hours) using similar methods. The TIMP-3 muteins demonstrated increased system half-life compared to native TIMP-3 and the N-terminal domain of native TIMP-3 (both 0.8 hours).

Area under the curve (AUC; hr*µg/mL) was examined for TIMP-3 [H78N, Q80T, K94N, E96T, D110N, K112T, R138T] and TIMP-3 [K45S, F57N]. An intravenous bolus of 3 mg/kg of TIMP-3 polypeptide was administered to rats. AUC for TIMP-3 [H78N, Q80T, K94N, E96T, D110N, K112T, R138T] was 62.5±4.0 compared to 16.0±1.9 for TIMP-3 [K45S, F57N]. TIMP-3 [H78N, Q80T, K94N, E96T, D110N, K112T, R138T] exhibited improvement in clearance and exposure in vivo compared to TIMP-3 [K45S, F57N].

Example 7:

This Example describes representative in vivo studies of TIMP-3 polypeptides in clinically-acceptable animal models. TIMP-3 and TIMP-3 muteins were administered to porcine or rat hearts to determine half-life and effect on cardiac function.

Mature Yorkshire pigs (25-30 kg) were acclimated and handled with pre-operative procedures according to IACUC protocol. The region encompassing the right femoral artery was prepared in a sterile fashion and the main branch of the femoral artery surgically exposed. A catheter introducer (6F Input Introducer Sheath, Medtronic) was positioned and stabilized in the artery, and the sheath was placed with an initial heparin bolus (4000 units, IV) followed by an additional bolus every hour (1000 units, IV). Under fluoroscopic guidance (GE OEC 9600, UT), a coronary angiography catheter/launcher (5F Launcher guiding catheter, Medtronic) was placed in the left coronary ostia. An angioplasty balloon catheter containing an injection lumen (3 mm×10 mm Sprinter OTW balloon catheter, Medtronic) was positioned in the lower portion of the left anterior descending artery (LAD). The LAD was occluded by balloon inflation (12 ATM balloon inflation pressure, Everest 30 Disposable inflation device, Medtronic) and maintained for 90 minutes. When imaging was performed, IR800 dye (DyLight 800 NHS ester, Thermo Scientific) labeled TIMP-3 (5 mg) was slowly infused through the lumen of the balloon occlusion catheter to the ischemic myocardial region just prior to reperfusion. The balloon was then deflated, and the catheter system was disengaged and removed. The femoral artery was ligated and the incision closed. Post-operative analgesia was facilitated by buprenorphine (0.05 mg/kg, IM) administered pre-operatively, as well as a fentanyl patch (25 ug/hr, 72 hr) placed pre-operatively and three days post-operatively. Additional lidocaine (1 mg/kg, IV) and amiodarone (200 mg PO) was administered for three days post-operatively, and aspirin (81 mg PO) was administered each day until the terminal procedure.

Figure 7:
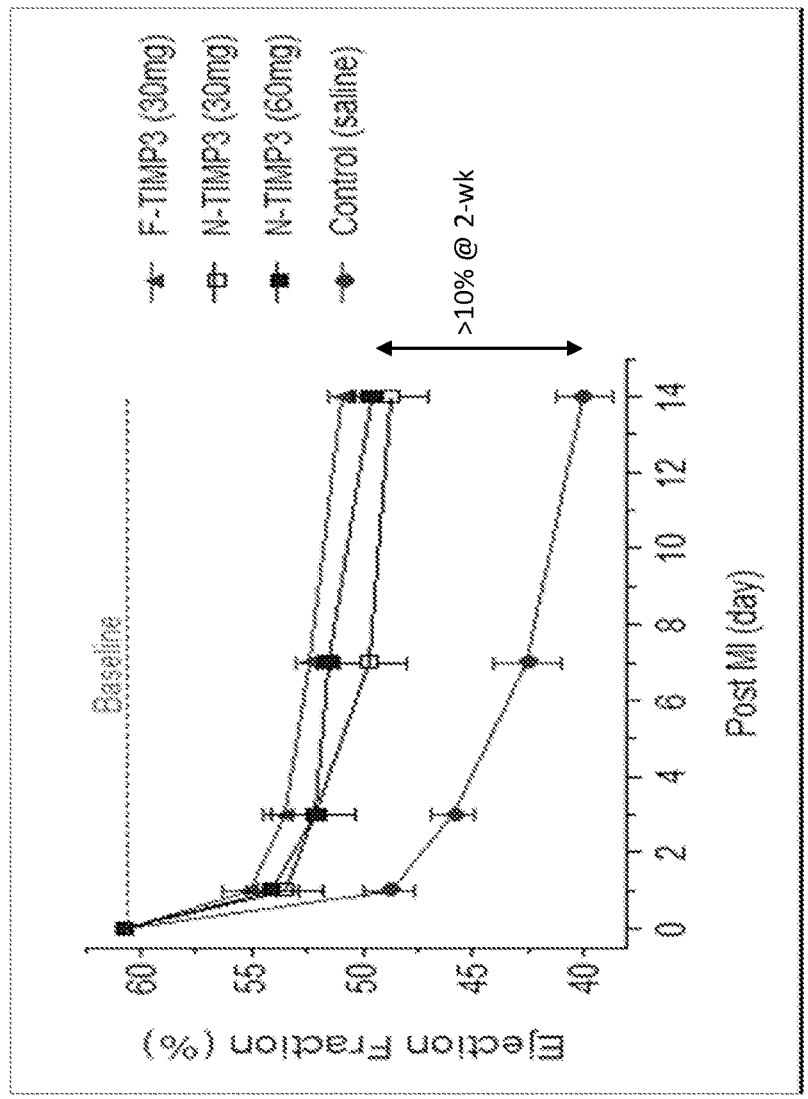
FIG. 7 is a line graph illustrating ejection fraction (%) (y-axis) observed over time (day, x-axis) post-myocardial infarction following administration of TIMP-3 polypeptides. Triangle=full length TIMP-3 (30 mg); Open square=N-terminal domain of TIMP-3 (N-TIMP3) (30 mg); Closed square=N-TIMP3 (30 mg), Circle=control (saline).
Figure 9:
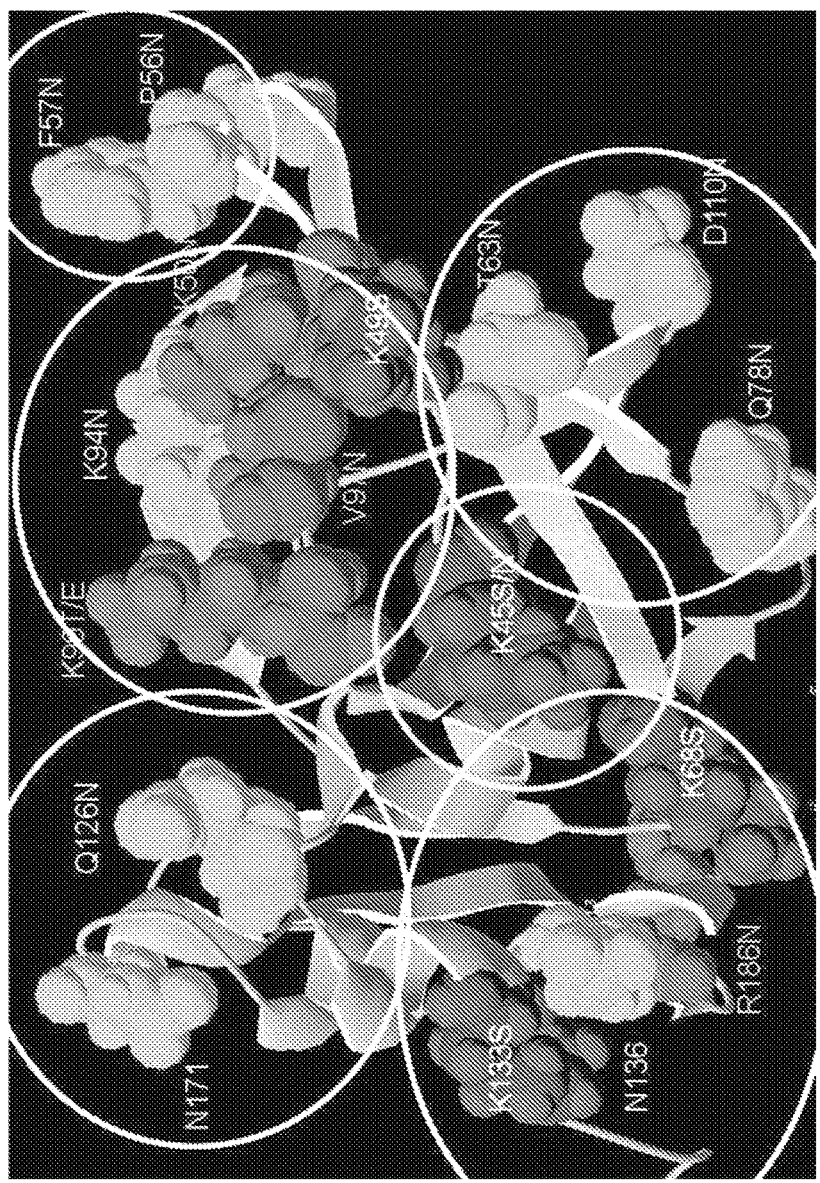
FIG. 9 is an illustration of the three dimensional structure of TIMP-3 noting the positions of various amino acids.

Full length native TIMP-3 (F-TIMP3) and the N-terminal TIMP-3 domain (AA 1-144, N-TIMP3) was directly injected into porcine myocardium following ligation-induced myocardial infarction. Administration of the polypeptides significantly improved cardiac function; ejection fraction was improved greater than 10% compared to saline injection at two weeks post-infarction. See FIG. 7.

For imaging procedures, at the designated post I/R time point (3 hrs, 1 day, 3 days, 7 days, and 14 days), the pigs were anesthetized with isoflurane (5%) and the LV was harvested. The entire LV was prepared for analysis. Full circumferential sections of the apical, mid (2 sections) and base regions were subjected to whole mount imaging to compute TIMP-3 distribution as a function of LV area. The sections were placed on ice and immediately subjected to imaging. The circumferential LV section from each region was subjected to epi-illumination imaging (Xenogen IVIS, PerkinElmer, Inc, MA). The settings for the imaging system was predicated upon the IRDye800 spectra (745/800 ex/em), and the signal was collected over a 0.5 sec exposure window. The digitized images (Living Image Software, PerkinElmer Inc., MA) were subjected to planimetry (Image J Software, Research Services Branch, MD) to determine the total LV circumferential area for that region. For the mid LV region, whereby duplicate measurements were made, the averages for both were computed. The final results were expressed as the area occupied by IR800-TIMP-3, and expressed as a percent of the total LV regional area. For additional quantitative measures of TIMP-3 distribution, LV sections (70-100 mg) from each region and from each sector were subjected to fluorescence/spectroscopy (Li-Cor Odyssey CLx, Li-Cor Biosciences, NE). Sections from the harvested organs (~100 mg) and plasma samples (200 uL) were also placed in a 96 well, black walled microplate subjected to analysis. Following correction for background, the spectroscopic signal from the sample well plate (20 min) was then normalized to absolute sample weights (mg) or plasma volume (mL).

Figure 5:
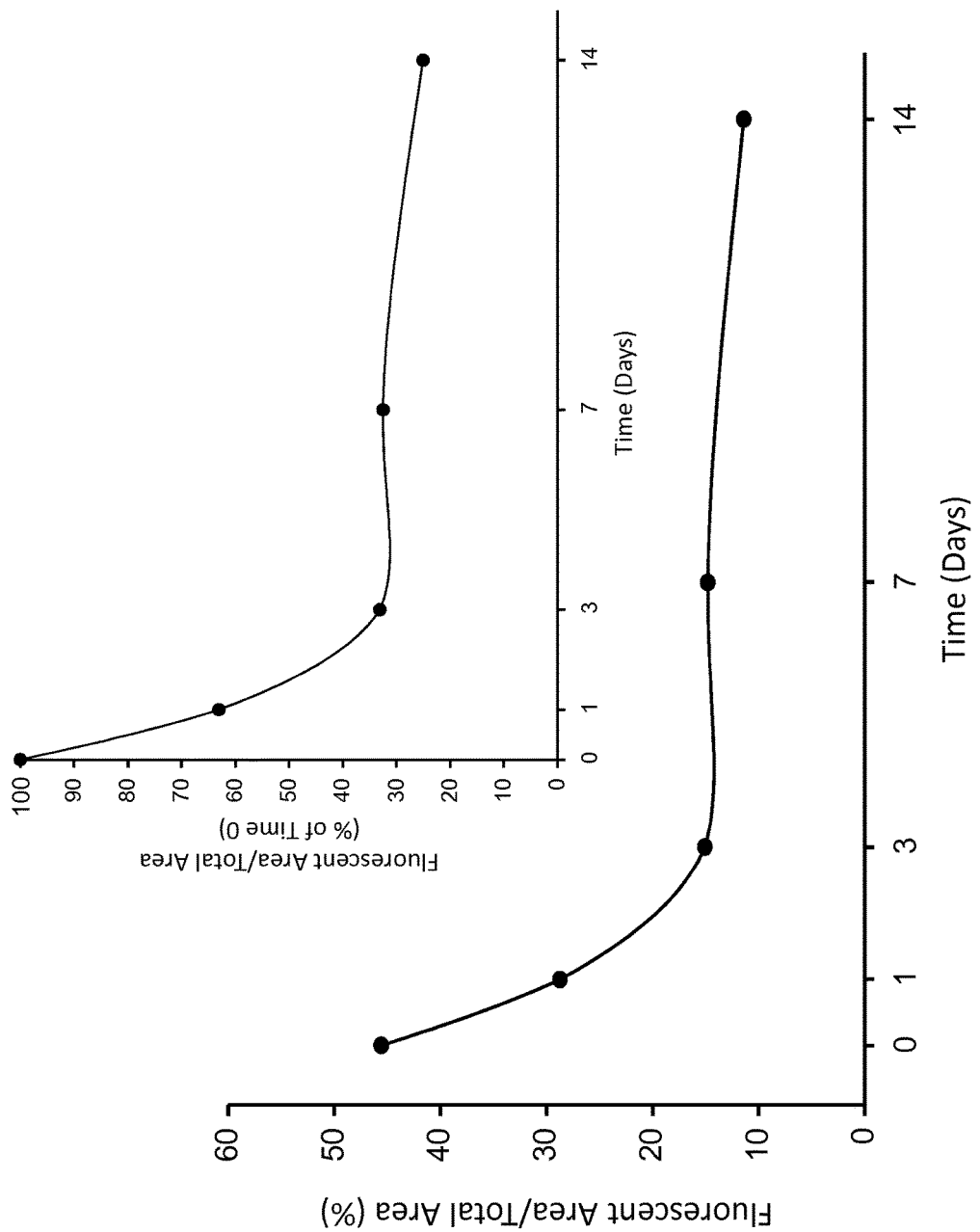
FIG. 5 contains two line graphs illustrating pharmacokinetic properties of TIMP-3 [K45S, F56N], comparing fluorescent area/total area (%) or fluorescent area/total area (% of time 0) (y-axis) to days post infarction (x-axis).
Figure 6:
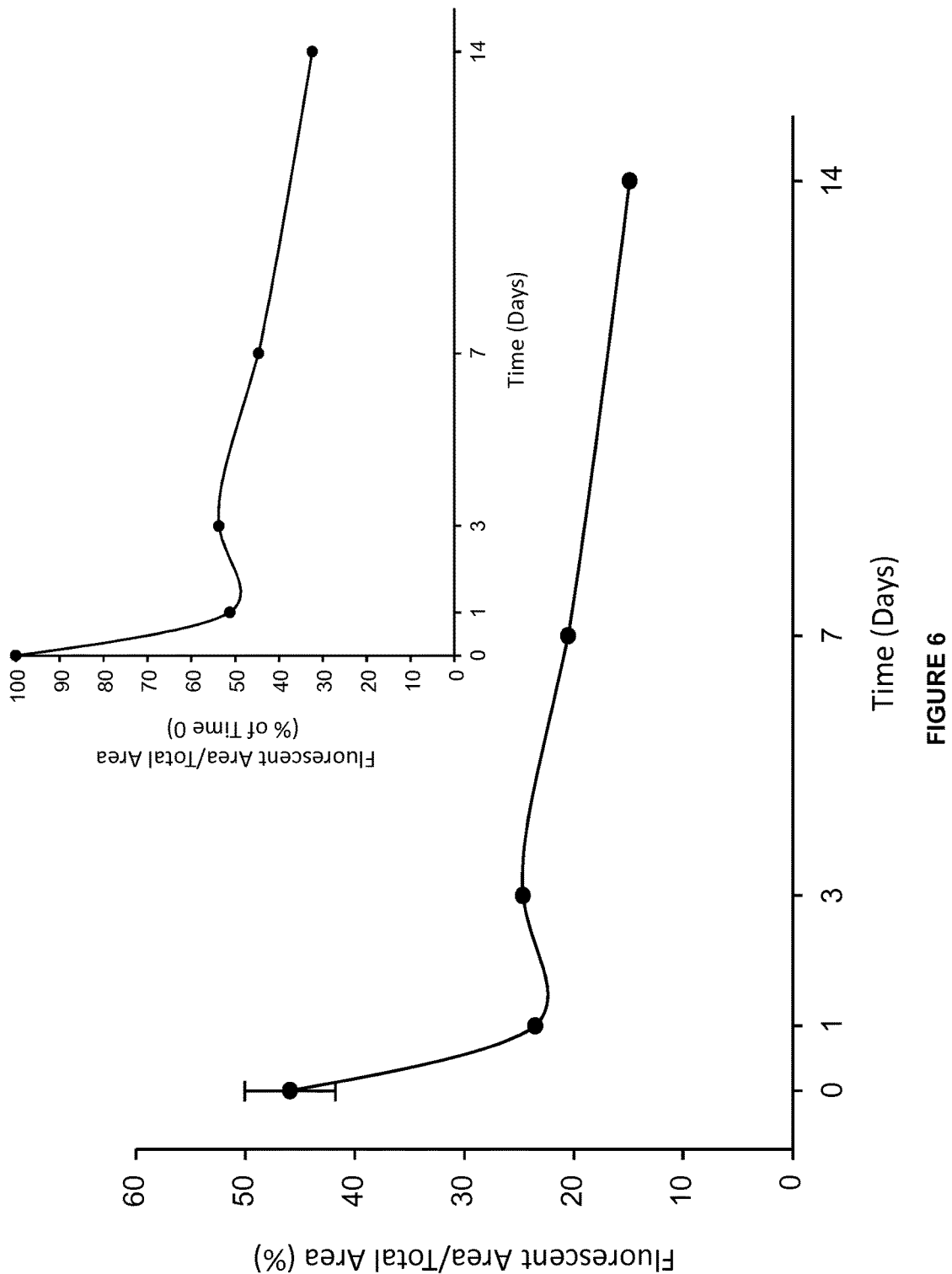
FIG. 6 contains two line graphs illustrating pharmacokinetic properties of TIMP-3 [H78N, Q80T, K94N, E96T, D110N, K112T, R138T] (SEQ ID NO:26), comparing fluorescent area/total area (%) or fluorescent area/total area (% of time 0) (y-axis) to days post infarction (x-axis).

TIMP-3 is rapidly cleared when administered systemically; the half-life of TIMP-3 when administered intravenously is less than one hour. Using imaging procedures similar to those described above, it was determined that the half-life of full length native TIMP-3 (F-TIMP3) and the N-terminal TIMP-3 domain (AA 1-144, N-TIMP3) was about 5 days and 3.4 days, respectively, in cardiac tissue following direct injection after ligation-induced myocardial infarction. Similarly, a longer cardiac retention of TIMP-3 polypeptides following intracoronary catheter delivery is expected because TIMP3 has high binding affinity toward extracellular matrix proteins in the myocardium. Cardiac tissue half-life of TIMP-3 [K45S, F57N] was approximately 3 days in the porcine myocardial infarct model. See FIG. 5 ($t_{1/2}$=y=a*e$^{(-b*x)}$). Cardiac tissue half-life of TIMP-3 [H78N, Q80T, K94N, E96T, D110N, K112T, R138T] (SEQ ID NO:26) was approximately 5.43 days (i.e., improved greater than 50-fold longer than intravenous administration). See FIG. 6.

Using methods similar to those described above for porcine, myocardial infarction was instituted in rat hearts and TIMP-3 [H78N, Q80T, K94N, E96T, D110N, K112T, R138T] (SEQ ID NO:26) was administered to observe the impact on cardiac function. Rats were administered vehicle (PBS, n=9) or 4 mg of TIMP-3 [H78N, Q80T, K94N, E96T, D110N, K112T, R138T] (n=8) via myocardial injection. Ejection fraction (EF %) was measured via echocardiography at day 3 and day 7 post-injection. Animals administered TIMP-3 [H78N, Q80T, K94N, E96T, D110N, K112T, R138T] demonstrated significantly enhanced EF on both days compared to control (more than 20% increase compared to control). See FIG. 8A. End-systolic volume (ESV) and end-diastolic volume (EDV) are indicators of cardiac remodeling; left ventricular (LV) remodeling after acute myocardial infarction is marked by a progressive increase of EDV and ESV compared to baseline. As illustrated in FIGS. 8B and 8C, TIMP-3 [H78N, Q80T, K94N, E96T, D110N, K112T, R138T] reduced ESV and EDV compared to control.

This results described above demonstrate that a representative TIMP-3 mutein of the invention has increased half-life compared to native TIMP-3, reduces adverse cardiac remodeling, and improves cardiac function following acute myocardial infarction.

---

What is claimed is:

1. An isolated Tissue Inhibitor of Metalloproteinase Type Three (TIMP-3) mutein having a mature region that is at least 90% identical in amino acid sequence to the mature region of TIMP-3 set forth in SEQ ID NO:2, selected from the group consisting of:
   a) a TIMP-3 mutein having two or more pairs of mutations selected from the group consisting of K45N/V47T; K50N/V52T; P56N/G58T; H78N/Q80T; K94N/E96T; and D110N/K112T;
   b) a TIMP-3 mutein having one or more pairs of mutations selected from the group consisting of K45N/V47T; K50N/V52T; P56N/G58T; H78N/Q80T; K94N/E96T; and D110N/K112T; and an additional mutation that is selected from the group consisting of R138T; G173T, and both R138T and G173T; and
   c) the TIMP-3 mutein according to a) or b) that further comprises the mutation F57N.

2. A Tissue Inhibitor of Metalloproteinase Type Three (TIMP-3) mutein having a mature region that is at least 90% identical in amino acid sequence to amino acids 24-211 of SEQ ID NO:2, selected from the group consisting of:
   a) a TIMP-3 mutein having two or more pairs of mutations selected from the group consisting of K45N/V47T; K50N/V52T; P56N/G58T; H78N/Q80T; K94N/E96T; and D110N/K112T;
   b) a TIMP-3 mutein having one or more pairs of mutations selected from the group consisting of K45N/V47T; K50N/V52T; P56N/G58T; H78N/Q80T; K94N/E96T; and D110N/K112T; and an additional mutation that is selected from the group consisting of R138T; G173T, and both R138T and G173T; and c) the TIMP-3 mutein according to a) or b) that further comprises the mutation F57N.

3. The TIMP-3 mutein of claim 1, comprising a group of mutations selected from the group consisting of:
   (i) K45N/V47T, P56N/G58T, Q126N, and R138T;
   (ii) K45N/V47T, P56N/G58T, K94N/E96T, and R138T;
   (iii) K45N/V47T, P56N/G58T, R138T and G173T;
   (iv) K45N/V47T, K94N/E96T, D110N/K112T, and F57N;
   (v) K45N/V47T, K94N/E96T, F57N and R138T;
   (vi) K45N/V47T, H78N/Q80T, K94N/E96T, R138T, and G173T;
   (vii) K45N/V47T, K94N/E96T, D110N/K112T, and R138T;
   (viii) K45N/V47T, K94N/E96T, D110N/K112T, and G173T;
   (ix) K45N/V47T, K94N/E96T, R138T and G173T;
   (x) K94N/E96T, D110N/K112T, K45S, F57N, and R138T;
   (xi) H78N/Q80T, K94N/E96T, K45S, F57N and R138T;
   (xii) K50N/V52T, P56N/G58T, K94N/E96T, D110N/K112T, R138T;
   (xiii) K50N/V52T, H78N/Q80T, K94N/E96T, R138T and G173T;
   (xiv) K50N/V52T, K94N/E96T, D110N/K112T, and R138T;
   (xv) K50N/V52T, K94N/E96T, D110N/K112T, R138T and G173T;
   (xvi) K50N/V52T, K94N/E96T, R138T and G173T;
   (xvii) K50N/V52T, Q126N, R138T, and G173T;
   (xviii) P56N/G58T, H78N/Q80T, K94N/E96T, and R138T;
   (xix) P56N/G58T, K94N/E96T, Q126N and R138T;
   (xx) P56N/G58T, K94N/E96T, D110N/K112T, and R138T;
   (xxi) P56N/G58T, H78N/Q80T, K94N/E96T, and G173T;
   (xxii) P56N/G58T, Q126N, R138T, and G173T;
   (xxiii) H78N/Q80T, K94N/E96T, R138T and G173T;
   (xxiv) H78N/Q80T, K94N/E96T, D110N/K112T, and R138T;
   (xxv) K50N/V52T, D110N/K112T, R138T and G173T;
   (xxvi) K45N/V47T, D110N/K112T, R138T and G173T;
   (xxvii) H78N/Q80T, D110N/K112T, R138T and G173T;
   (xxviii) K45N/V47T, K50N/V52T, H78N/Q80T, R138T;
   (xxix) K45N/V47T, H78N/Q80T, D110N/K112T, and G173T;
   (xxxx) K45N/V47, H78N/Q80T, R138T and G173T;
   (xxxi) K50N/V52T, H78N/Q80T, K94N/E96T, and G173T;

(xxxii) K50N/V52T, H78N/Q80T, D110N/K112T, and R138T;
(xxxiii) K45N/V47T, K50N/V52T, H78N/Q80T, and D110N/K112T;
(xxxiv) K50N/V52T, H78N/Q80T, R138T and G173T;
(xxxv) K45N/V47T, H78N/Q80T, R138T and G173T;
(xxxvi) K45N/V47T, H78N/Q80T, and D110N/K112T, and R138T;
(xxxvii) K45N/V47T, K50N/V52T, H78N/Q80T, D110N/K112T, and G173T;
(xxxviii) K45N/V47T, K50N/V52T, H78N/Q80T, and R138T and G173T;
(xxxix) K45N/V47T, K50N/V52T, H78N/Q80T, K94N/E96T, and G173T;
(xl) K45N/V47T, H78N/Q80T, K94N/E96T, R138T and G173T;
(xli) K50N/V52T, H78N/Q80T, K94N/E96T, R138T and G173T;
(xlii) K45N/V47T, H78N/Q80T, and D110N/K112T, R138T and G173T;
(xliii) K50N/V52T, H78N/Q80T, D110N/K112T, R138T and G173T; and
(xliv) K45N/V52T, K50N/V52T, H78N/Q80T, D110N/K112T, and R138T.

4. The TIMP-3 mutein of claim 3, comprising an amino acid sequence selected from the group consisting of SEQ ID NOs: 3-26.

5. The TIMP-3 mutein of claim 1 fused or conjugated to a moiety that extends half-life of a polypeptide.

6. The TIMP-3 mutein of claim 5 fused to an antibody, an Fc portion of an antibody, the heavy chain or light chain of an antibody, or human serum albumin.

7. The TIMP-3 mutein of claim 5 conjugated to polyethylene glycol.

8. An isolated nucleic acid that encodes a Tissue Inhibitor of Metalloproteinase Type Three (TIMP-3) mutein according to claim 1.

9. An expression vector comprising the isolated nucleic acid of claim 8.

10. An isolated host cell transformed or transfected with the expression vector of claim 9.

11. A method of producing a recombinant Tissue Inhibitor of Metalloproteinase Type Three (TIMP-3) mutein comprising culturing the transformed or transfected host cell of claim 10 under conditions promoting expression of the TIMP-3 mutein, and recovering the TIMP-3 mutein.

12. A composition comprising the Tissue Inhibitor of Metalloproteinase Type Three (TIMP-3) mutein of claim 1 and a physiologically acceptable diluent, excipient or carrier.

13. A method of inhibiting cardiac extracellular matrix (ECM) degradation or adverse cardiac remodeling in a subject, the method comprising administering to a subject in need thereof an amount of composition of claim 12 effective to inhibit ECM degradation and/or adverse cardiac remodeling.

14. The method of claim 13, wherein the subject has suffered a myocardial infarction.

15. The method of claim 13, wherein the composition is administered via intracoronary administration or direct injection into the myocardium.

16. The isolated TIMP-3 mutein of claim 1, comprising the mutations H78N/Q80T, K94N/E96T, and D110N/K112T.

17. The isolated TIMP-3 mutein of claim 16, further comprising one or more mutations selected from the group consisting of K45N/V47T, K50N/V52T, and P56N/G58T.

18. The isolated TIMP-3 mutein of claim 16, further comprising a mutation selected from the group consisting of R138T, G173T, and both R138T and G173T.

19. The isolated TIMP-3 mutein of claim 16, further comprising the mutation F57N.

20. The isolated TIMP-3 mutein of claim 2, comprising the mutations H78N/Q80T, K94N/E96T, and D110N/K112T.

21. The isolated TIMP-3 mutein of claim 20, further comprising one or more mutations selected from the group consisting of K45N/V47T, K50N/V52T, and P56N/G58T.

22. The isolated TIMP-3 mutein of claim 20, further comprising a mutation selected from the group consisting of R138T, G173T, and both R138T and G173T.

23. The isolated TIMP-3 mutein of claim 20, further comprising the mutation F57N.

24. A composition comprising the Tissue Inhibitor of Metalloproteinase Type Three (TIMP-3) mutein of claim 16 and a physiologically acceptable diluent, excipient or carrier.

25. A composition comprising the TIMP-3 mutein of claim 20 and a physiologically acceptable diluent, excipient or carrier.

26. A method of inhibiting cardiac extracellular matrix (ECM) degradation or adverse cardiac remodeling in a subject, the method comprising administering to a subject in need thereof an amount of composition of claim 24 effective to inhibit ECM degradation and/or adverse cardiac remodeling.

27. A method of inhibiting cardiac extracellular matrix (ECM) degradation or adverse cardiac remodeling in a subject, the method comprising administering to a subject in need thereof an amount of composition of claim 25 effective to inhibit ECM degradation and/or adverse cardiac remodeling.

* * * * *

SEQUENCE LISTING

<160> NUMBER OF SEQ ID NOS: 79

<210> SEQ ID NO 1
<211> LENGTH: 633
<212> TYPE: DNA
<213> ORGANISM: Homo sapiens

<400> SEQUENCE: 1

```
atgacccctt ggctcgggct catcgtgctc ctgggcagct ggagcctggg ggactggggc      60
gccgaggcgt gcacatgctc gcccagccac ccccaggacg ccttctgcaa ctccgacatc     120
gtgatccggg ccaaggtggt ggggaagaag ctggtaaagg aggggccctt cggcacgctg     180
gtctacacca tcaagcagat gaagatgtac cgaggcttca ccaagatgcc ccatgtgcag     240
tacatccaca cggaagcttc cgagagtctc tgtggcctta agctggaggt caacaagtac     300
cagtacctgc tgacaggtcg cgtctatgat ggcaagatgt acacggggct gtgcaacttc     360
gtggagaggt gggaccagct caccctctcc cagcgcaagg gctgaactac tcggtatcac     420
ctgggttgta actgcaagat caagtcctgc tactacctgc cttgctttgt gacttccaag     480
aacgagtgtc tctggaccga catgctctcc aatttcggtt accctggcta ccagtccaaa     540
cactacgcct gcatccggca gaagggcggc tactgcagct ggtaccgagg atgggccccc     600
ccggataaaa gcatcatcaa tgccacagac ccc                                  633
```

<210> SEQ ID NO 2
<211> LENGTH: 211
<212> TYPE: PRT
<213> ORGANISM: Homo sapiens

<400> SEQUENCE: 2

```
Met Thr Pro Trp Leu Gly Leu Ile Val Leu Leu Gly Ser Trp Ser Leu
1               5                   10                  15

Gly Asp Trp Gly Ala Glu Ala Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175
```

-continued

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210

<210> SEQ ID NO 3
<211> LENGTH: 188
<212> TYPE: PRT
<213> ORGANISM: Homo sapiens

<400> SEQUENCE: 3

Cys Thr Cys Ser Pro Ser His Pro Gln Asp Ala Phe Cys Asn Ser Asp
1               5                   10                  15

Ile Val Ile Arg Ala Asn Val Thr Gly Lys Lys Leu Val Lys Glu Gly
            20                  25                  30

Asn Phe Thr Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Lys Leu Glu Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Asn Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185

<210> SEQ ID NO 4
<211> LENGTH: 188
<212> TYPE: PRT
<213> ORGANISM: Homo sapiens

<400> SEQUENCE: 4

Cys Thr Cys Ser Pro Ser His Pro Gln Asp Ala Phe Cys Asn Ser Asp
1               5                   10                  15

Ile Val Ile Arg Ala Asn Val Thr Gly Lys Lys Leu Val Lys Glu Gly
            20                  25                  30

Asn Phe Thr Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
                100                 105                 110

Asn Tyr Thr Tyr His Leu Gly Cys Asn Cys Lys Ile Lys Ser Cys Tyr
            115                 120                 125

Tyr Leu Pro Cys Phe Val Thr Ser Lys Asn Glu Cys Leu Trp Thr Asp
        130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185

<210> SEQ ID NO 5
<211> LENGTH: 188
<212> TYPE: PRT
<213> ORGANISM: Homo sapiens

<400> SEQUENCE: 5

Cys Thr Cys Ser Pro Ser His Pro Gln Asp Ala Phe Cys Asn Ser Asp
1               5                   10                  15

Ile Val Ile Arg Ala Asn Val Thr Gly Lys Lys Leu Val Lys Glu Gly
            20                  25                  30

Asn Phe Thr Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Lys Leu Glu Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
                100                 105                 110

Asn Tyr Thr Tyr His Leu Gly Cys Asn Cys Lys Ile Lys Ser Cys Tyr
            115                 120                 125

Tyr Leu Pro Cys Phe Val Thr Ser Lys Asn Glu Cys Leu Trp Thr Asp
        130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185

<210> SEQ ID NO 6
<211> LENGTH: 188
<212> TYPE: PRT
<213> ORGANISM: Homo sapiens

<400> SEQUENCE: 6

Cys Thr Cys Ser Pro Ser His Pro Gln Asp Ala Phe Cys Asn Ser Asp
1               5                   10                  15

Ile Val Ile Arg Ala Asn Val Thr Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

-continued

Gly Phe Thr Lys Met Pro His Val Gln Tyr Ile His Thr Glu Ala Ser
            50                  55                  60

Glu Ser Leu Cys Gly Leu Asn Leu Thr Val Asn Lys Tyr Gln Tyr Leu
 65                  70                  75                  80

Leu Thr Gly Arg Val Tyr Asn Gly Thr Met Tyr Thr Gly Leu Cys Asn
                 85                  90                  95

Phe Val Glu Arg Trp Asp Gln Leu Thr Leu Ser Gln Arg Lys Gly Leu
                100                 105                 110

Asn Tyr Arg Tyr His Leu Gly Cys Asn Cys Lys Ile Lys Ser Cys Tyr
            115                 120                 125

Tyr Leu Pro Cys Phe Val Thr Ser Lys Asn Glu Cys Leu Trp Thr Asp
130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
                180                 185

<210> SEQ ID NO 7
<211> LENGTH: 188
<212> TYPE: PRT
<213> ORGANISM: Homo sapiens

<400> SEQUENCE: 7

Cys Thr Cys Ser Pro Ser His Pro Gln Asp Ala Phe Cys Asn Ser Asp
 1               5                  10                  15

Ile Val Ile Arg Ala Asn Val Thr Gly Lys Lys Leu Val Lys Glu Gly
                 20                  25                  30

Pro Asn Gly Thr Leu Val Tyr Thr Ile Lys Gln Met Lys Met Tyr Arg
                 35                  40                  45

Gly Phe Thr Lys Met Pro His Val Gln Tyr Ile His Thr Glu Ala Ser
            50                  55                  60

Glu Ser Leu Cys Gly Leu Asn Leu Thr Val Asn Lys Tyr Gln Tyr Leu
 65                  70                  75                  80

Leu Thr Gly Arg Val Tyr Asp Gly Lys Met Tyr Thr Gly Leu Cys Asn
                 85                  90                  95

Phe Val Glu Arg Trp Asp Gln Leu Thr Leu Ser Gln Arg Lys Gly Leu
                100                 105                 110

Asn Tyr Thr Tyr His Leu Gly Cys Asn Cys Lys Ile Lys Ser Cys Tyr
            115                 120                 125

Tyr Leu Pro Cys Phe Val Thr Ser Lys Asn Glu Cys Leu Trp Thr Asp
130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
                180                 185

<210> SEQ ID NO 8
<211> LENGTH: 188
<212> TYPE: PRT
<213> ORGANISM: Homo sapiens

<400> SEQUENCE: 8

```
Cys Thr Cys Ser Pro Ser His Pro Gln Asp Ala Phe Cys Asn Ser Asp
1               5                   10                  15

Ile Val Ile Arg Ala Asn Val Thr Gly Lys Lys Leu Val Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro Asn Val Thr Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
                100                 105                 110

Asn Tyr Thr Tyr His Leu Gly Cys Asn Cys Lys Ile Lys Ser Cys Tyr
            115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185

<210> SEQ ID NO 9
<211> LENGTH: 188
<212> TYPE: PRT
<213> ORGANISM: Homo sapiens

<400> SEQUENCE: 9

Cys Thr Cys Ser Pro Ser His Pro Gln Asp Ala Phe Cys Asn Ser Asp
1               5                   10                  15

Ile Val Ile Arg Ala Asn Val Thr Gly Lys Lys Leu Val Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
                100                 105                 110

Asn Tyr Thr Tyr His Leu Gly Cys Asn Cys Lys Ile Lys Ser Cys Tyr
            115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
```

```
                180             185

<210> SEQ ID NO 10
<211> LENGTH: 188
<212> TYPE: PRT
<213> ORGANISM: Homo sapiens

<400> SEQUENCE: 10

Cys Thr Cys Ser Pro Ser His Pro Gln Asp Ala Phe Cys Asn Ser Asp
1               5                   10                  15

Ile Val Ile Arg Ala Asn Val Thr Gly Lys Lys Leu Val Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185

<210> SEQ ID NO 11
<211> LENGTH: 188
<212> TYPE: PRT
<213> ORGANISM: Homo sapiens

<400> SEQUENCE: 11

Cys Thr Cys Ser Pro Ser His Pro Gln Asp Ala Phe Cys Asn Ser Asp
1               5                   10                  15

Ile Val Ile Arg Ala Asn Val Thr Gly Lys Lys Leu Val Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
```

```
            130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185

<210> SEQ ID NO 12
<211> LENGTH: 188
<212> TYPE: PRT
<213> ORGANISM: Homo sapiens

<400> SEQUENCE: 12

Cys Thr Cys Ser Pro Ser His Pro Gln Asp Ala Phe Cys Asn Ser Asp
1               5                   10                  15

Ile Val Ile Arg Ala Ser Val Val Gly Lys Lys Leu Val Lys Glu Gly
                20                  25                  30

Pro Asn Gly Thr Leu Val Tyr Thr Ile Lys Gln Met Lys Met Tyr Arg
            35                  40                  45

Gly Phe Thr Lys Met Pro His Val Gln Tyr Ile His Thr Glu Ala Ser
        50                  55                  60

Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185

<210> SEQ ID NO 13
<211> LENGTH: 188
<212> TYPE: PRT
<213> ORGANISM: Homo sapiens

<400> SEQUENCE: 13

Cys Thr Cys Ser Pro Ser His Pro Gln Asp Ala Phe Cys Asn Ser Asp
1               5                   10                  15

Ile Val Ile Arg Ala Ser Val Val Gly Lys Lys Leu Val Lys Glu Gly
                20                  25                  30

Pro Asn Gly Thr Leu Val Tyr Thr Ile Lys Gln Met Lys Met Tyr Arg
            35                  40                  45

Gly Phe Thr Lys Met Pro Asn Val Thr Tyr Ile His Thr Glu Ala Ser
        50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
```

```
                    85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185

<210> SEQ ID NO 14
<211> LENGTH: 188
<212> TYPE: PRT
<213> ORGANISM: Homo sapiens

<400> SEQUENCE: 14

Cys Thr Cys Ser Pro Ser His Pro Gln Asp Ala Phe Cys Asn Ser Asp
1               5                   10                  15

Ile Val Ile Arg Ala Lys Val Val Gly Lys Asn Leu Thr Lys Glu Gly
            20                  25                  30

Asn Phe Thr Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185

<210> SEQ ID NO 15
<211> LENGTH: 188
<212> TYPE: PRT
<213> ORGANISM: Homo sapiens

<400> SEQUENCE: 15

Cys Thr Cys Ser Pro Ser His Pro Gln Asp Ala Phe Cys Asn Ser Asp
1               5                   10                  15

Ile Val Ile Arg Ala Lys Val Val Gly Lys Asn Leu Thr Lys Glu Gly
            20                  25                  30

Pro Phe Gly Thr Leu Val Tyr Thr Ile Lys Gln Met Lys Met Tyr Arg
```

```
                35                  40                  45
Gly Phe Thr Lys Met Pro Asn Val Thr Tyr Ile His Thr Glu Ala Ser
 50                  55                  60

Glu Ser Leu Cys Gly Leu Asn Leu Thr Val Asn Lys Tyr Gln Tyr Leu
 65                  70                  75                  80

Leu Thr Gly Arg Val Tyr Asp Gly Lys Met Tyr Thr Gly Leu Cys Asn
                 85                  90                  95

Phe Val Glu Arg Trp Asp Gln Leu Thr Leu Ser Gln Arg Lys Gly Leu
                100                 105                 110

Asn Tyr Thr Tyr His Leu Gly Cys Asn Cys Lys Ile Lys Ser Cys Tyr
                115                 120                 125

Tyr Leu Pro Cys Phe Val Thr Ser Lys Asn Glu Cys Leu Trp Thr Asp
130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
                180                 185

<210> SEQ ID NO 16
<211> LENGTH: 188
<212> TYPE: PRT
<213> ORGANISM: Homo sapiens

<400> SEQUENCE: 16

Cys Thr Cys Ser Pro Ser His Pro Gln Asp Ala Phe Cys Asn Ser Asp
 1                5                  10                  15

Ile Val Ile Arg Ala Lys Val Val Gly Lys Asn Leu Thr Lys Glu Gly
                 20                  25                  30

Pro Phe Gly Thr Leu Val Tyr Thr Ile Lys Gln Met Lys Met Tyr Arg
                 35                  40                  45

Gly Phe Thr Lys Met Pro His Val Gln Tyr Ile His Thr Glu Ala Ser
 50                  55                  60

Glu Ser Leu Cys Gly Leu Asn Leu Thr Val Asn Lys Tyr Gln Tyr Leu
 65                  70                  75                  80

Leu Thr Gly Arg Val Tyr Asn Gly Thr Met Tyr Thr Gly Leu Cys Asn
                 85                  90                  95

Phe Val Glu Arg Trp Asp Gln Leu Thr Leu Ser Gln Arg Lys Gly Leu
                100                 105                 110

Asn Tyr Thr Tyr His Leu Gly Cys Asn Cys Lys Ile Lys Ser Cys Tyr
                115                 120                 125

Tyr Leu Pro Cys Phe Val Thr Ser Lys Asn Glu Cys Leu Trp Thr Asp
130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
                180                 185

<210> SEQ ID NO 17
<211> LENGTH: 188
<212> TYPE: PRT
<213> ORGANISM: Homo sapiens
```

<400> SEQUENCE: 17

Cys Thr Cys Ser Pro Ser His Pro Gln Asp Ala Phe Cys Asn Ser Asp
1               5                   10                  15

Ile Val Ile Arg Ala Lys Val Val Gly Lys Asn Leu Thr Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65              70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185

<210> SEQ ID NO 18
<211> LENGTH: 188
<212> TYPE: PRT
<213> ORGANISM: Homo sapiens

<400> SEQUENCE: 18

Cys Thr Cys Ser Pro Ser His Pro Gln Asp Ala Phe Cys Asn Ser Asp
1               5                   10                  15

Ile Val Ile Arg Ala Lys Val Val Gly Lys Asn Leu Thr Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65              70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

```
Pro Pro Asp Lys Ser Ile Ile Asn Ala Thr Asp Pro
            180                 185
```

<210> SEQ ID NO 19
<211> LENGTH: 188
<212> TYPE: PRT
<213> ORGANISM: Homo sapiens

<400> SEQUENCE: 19

```
Cys Thr Cys Ser Pro Ser His Pro Gln Asp Ala Phe Cys Asn Ser Asp
1               5                   10                  15

Ile Val Ile Arg Ala Lys Val Val Gly Lys Asn Leu Thr Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Lys Leu Glu Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Asn Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185
```

<210> SEQ ID NO 20
<211> LENGTH: 188
<212> TYPE: PRT
<213> ORGANISM: Homo sapiens

<400> SEQUENCE: 20

```
Cys Thr Cys Ser Pro Ser His Pro Gln Asp Ala Phe Cys Asn Ser Asp
1               5                   10                  15

Ile Val Ile Arg Ala Lys Val Val Gly Lys Lys Leu Val Lys Glu Gly
            20                  25                  30

Asn Phe Thr Thr Leu Val Tyr Thr Ile Lys Gln Met Lys Met Tyr Arg
        35                  40                  45

Gly Phe Thr Lys Met Pro Asn Val Thr Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125
```

```
Tyr Leu Pro Cys Phe Val Thr Ser Lys Asn Glu Cys Leu Trp Thr Asp
        130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185

<210> SEQ ID NO 21
<211> LENGTH: 188
<212> TYPE: PRT
<213> ORGANISM: Homo sapiens

<400> SEQUENCE: 21

Cys Thr Cys Ser Pro Ser His Pro Gln Asp Ala Phe Cys Asn Ser Asp
1               5                   10                  15

Ile Val Ile Arg Ala Lys Val Val Gly Lys Lys Leu Val Lys Glu Gly
                20                  25                  30

Asn Phe Thr Thr Leu Val Tyr Thr Ile Lys Gln Met Lys Met Tyr Arg
            35                  40                  45

Gly Phe Thr Lys Met Pro His Val Gln Tyr Ile His Thr Glu Ala Ser
        50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Asn Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
        130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185

<210> SEQ ID NO 22
<211> LENGTH: 188
<212> TYPE: PRT
<213> ORGANISM: Homo sapiens

<400> SEQUENCE: 22

Cys Thr Cys Ser Pro Ser His Pro Gln Asp Ala Phe Cys Asn Ser Asp
1               5                   10                  15

Ile Val Ile Arg Ala Lys Val Val Gly Lys Lys Leu Val Lys Glu Gly
                20                  25                  30

Asn Phe Thr Thr Leu Val Tyr Thr Ile Lys Gln Met Lys Met Tyr Arg
            35                  40                  45

Gly Phe Thr Lys Met Pro His Val Gln Tyr Ile His Thr Glu Ala Ser
        50                  55                  60

Glu Ser Leu Cys Gly Leu Asn Leu Thr Val Asn Lys Tyr Gln Tyr Leu
65                  70                  75                  80
```

Leu Thr Gly Arg Val Tyr Asn Gly Thr Met Tyr Thr Gly Leu Cys Asn
            85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
            115                 120                 125

Tyr Leu Pro Cys Phe Val Thr Ser Lys Asn Glu Cys Leu Trp Thr Asp
        130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185

<210> SEQ ID NO 23
<211> LENGTH: 188
<212> TYPE: PRT
<213> ORGANISM: Homo sapiens

<400> SEQUENCE: 23

Cys Thr Cys Ser Pro Ser His Pro Gln Asp Ala Phe Cys Asn Ser Asp
1               5                   10                  15

Ile Val Ile Arg Ala Lys Val Val Gly Lys Lys Leu Val Lys Glu Gly
            20                  25                  30

Asn Phe Thr Thr Leu Val Tyr Thr Ile Lys Gln Met Lys Met Tyr Arg
            35                  40                  45

Gly Phe Thr Lys Met Pro Asn Val Thr Tyr Ile His Thr Glu Ala Ser
        50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
            85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
            115                 120                 125

Tyr Leu Pro Cys Phe Val Thr Ser Lys Asn Glu Cys Leu Trp Thr Asp
        130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185

<210> SEQ ID NO 24
<211> LENGTH: 188
<212> TYPE: PRT
<213> ORGANISM: Homo sapiens

<400> SEQUENCE: 24

Cys Thr Cys Ser Pro Ser His Pro Gln Asp Ala Phe Cys Asn Ser Asp
1               5                   10                  15

Ile Val Ile Arg Ala Lys Val Val Gly Lys Lys Leu Val Lys Glu Gly
            20                  25                  30

Asn Phe Thr Thr Leu Val Tyr Thr Ile Lys Gln Met Lys Met Tyr Arg
            35                  40                  45

Gly Phe Thr Lys Met Pro His Val Gln Tyr Ile His Thr Glu Ala Ser
 50                  55                  60

Glu Ser Leu Cys Gly Leu Lys Leu Glu Val Asn Lys Tyr Gln Tyr Leu
 65                  70                  75                  80

Leu Thr Gly Arg Val Tyr Asp Gly Lys Met Tyr Thr Gly Leu Cys Asn
                 85                  90                  95

Phe Val Glu Arg Trp Asp Asn Leu Thr Leu Ser Gln Arg Lys Gly Leu
            100                 105                 110

Asn Tyr Thr Tyr His Leu Gly Cys Asn Cys Lys Ile Lys Ser Cys Tyr
            115                 120                 125

Tyr Leu Pro Cys Phe Val Thr Ser Lys Asn Glu Cys Leu Trp Thr Asp
            130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185

<210> SEQ ID NO 25
<211> LENGTH: 188
<212> TYPE: PRT
<213> ORGANISM: Homo sapiens

<400> SEQUENCE: 25

Cys Thr Cys Ser Pro Ser His Pro Gln Asp Ala Phe Cys Asn Ser Asp
1                   5                   10                  15

Ile Val Ile Arg Ala Lys Val Val Gly Lys Lys Leu Val Lys Glu Gly
                20                  25                  30

Pro Phe Gly Thr Leu Val Tyr Thr Ile Lys Gln Met Lys Met Tyr Arg
            35                  40                  45

Gly Phe Thr Lys Met Pro Asn Val Thr Tyr Ile His Thr Glu Ala Ser
 50                  55                  60

Glu Ser Leu Cys Gly Leu Asn Leu Thr Val Asn Lys Tyr Gln Tyr Leu
 65                  70                  75                  80

Leu Thr Gly Arg Val Tyr Asp Gly Lys Met Tyr Thr Gly Leu Cys Asn
                 85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
            115                 120                 125

Tyr Leu Pro Cys Phe Val Thr Ser Lys Asn Glu Cys Leu Trp Thr Asp
            130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185

<210> SEQ ID NO 26
<211> LENGTH: 188
<212> TYPE: PRT
<213> ORGANISM: Homo sapiens

<400> SEQUENCE: 26

```
Cys Thr Cys Ser Pro Ser His Pro Gln Asp Ala Phe Cys Asn Ser Asp
1               5                   10                  15

Ile Val Ile Arg Ala Lys Val Val Gly Lys Lys Leu Val Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro Asn Val Thr Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185
```

<210> SEQ ID NO 27
<211> LENGTH: 651
<212> TYPE: DNA
<213> ORGANISM: Homo sapiens

<400> SEQUENCE: 27

```
atgacccctt ggctcgggct catcgtgctc ctgggcagct ggagcctggg ggactggggc    60
gccgaggcgt gcacatgctc gcccagccac ccccaggacg ccttctgcaa ctccgacatc   120
gtgatccggg ccaatgtgac ggggaagaag ctggtaaagg aggggaactt caccacgctg   180
gtctacacca tcaagcagat gaagatgtac cgaggcttca ccaagatgcc ccatgtgcag   240
tacatccaca cggaagcttc cgagagtctc tgtggcctta agctggaggt caacaagtac   300
cagtacctgc tgacaggtcg cgtctatgat ggcaagatgt acacggggct gtgcaacttc   360
gtggagaggt gggacaatct cacccctctc cagcgcaagg ggctgaacta tacgtatcac   420
ctgggttgta actgcaagat caagtcctgc tactacctgc cttgctttgt gacttccaag   480
aacgagtgtc tctggaccga catgctctcc aatttcggtt accctggcta ccagtccaaa   540
cactacgcct gcatccggca aagggcgga tactgcagct ggtaccgagg atgggccccc   600
ccggataaaa gcatcatcaa tgccacagac ccccaccacc atcaccatca t            651
```

<210> SEQ ID NO 28
<211> LENGTH: 651
<212> TYPE: DNA
<213> ORGANISM: Homo sapiens

<400> SEQUENCE: 28

```
atgacccctt ggctcgggct catcgtgctc ctgggcagct ggagcctggg ggactggggc    60
```

| | |
|---|---|
| gccgaggcgt gcacatgctc gcccagccac ccccaggacg ccttctgcaa ctccgacatc | 120 |
| gtgatccggg ccaatgtgac ggggaagaag ctggtaaagg aggggaactt caccacgctg | 180 |
| gtctacacca tcaagcagat gaagatgtac cgaggcttca ccaagatgcc ccatgtgcag | 240 |
| tacatccaca cggaagcttc cgagagtctc tgtggcctta atctgacggt caacaagtac | 300 |
| cagtacctgc tgacaggtcg cgtctatgat ggcaagatgt acacggggct gtgcaacttc | 360 |
| gtggagaggt gggaccagct cacccctctcc cagcgcaagg ggctgaacta tacgtatcac | 420 |
| ctgggttgta actgcaagat caagtcctgc tactacctgc cttgctttgt gacttccaag | 480 |
| aacgagtgtc tctggaccga catgctctcc aatttcggtt accctggcta ccagtccaaa | 540 |
| cactacgcct gcatccggca aagggcggc tactgcagct ggtaccgagg atgggccccc | 600 |
| ccggataaaa gcatcatcaa tgccacagac ccccaccacc atcaccatca t | 651 |

<210> SEQ ID NO 29
<211> LENGTH: 651
<212> TYPE: DNA
<213> ORGANISM: Homo sapiens

<400> SEQUENCE: 29

| | |
|---|---|
| atgacccctt ggctcgggct catcgtgctc ctgggcagct ggagcctggg ggactggggc | 60 |
| gccgaggcgt gcacatgctc gcccagccac ccccaggacg ccttctgcaa ctccgacatc | 120 |
| gtgatccggg ccaatgtgac ggggaagaag ctggtaaagg aggggaactt caccacgctg | 180 |
| gtctacacca tcaagcagat gaagatgtac cgaggcttca ccaagatgcc ccatgtgcag | 240 |
| tacatccaca cggaagcttc cgagagtctc tgtggcctta agctggaggt caacaagtac | 300 |
| cagtacctgc tgacaggtcg cgtctatgat ggcaagatgt acacggggct gtgcaacttc | 360 |
| gtggagaggt gggaccagct cacccctctcc cagcgcaagg ggctgaacta tacgtatcac | 420 |
| ctgggttgta actgcaagat caagtcctgc tactacctgc cttgctttgt gacttccaag | 480 |
| aacgagtgtc tctggaccga catgctctcc aatttcactt accctggcta ccagtccaaa | 540 |
| cactacgcct gcatccggca aagggcggc tactgcagct ggtaccgagg atgggccccc | 600 |
| ccggataaaa gcatcatcaa tgccacagac ccccaccacc atcaccatca t | 651 |

<210> SEQ ID NO 30
<211> LENGTH: 651
<212> TYPE: DNA
<213> ORGANISM: Homo sapiens

<400> SEQUENCE: 30

| | |
|---|---|
| atgacccctt ggctcgggct catcgtgctc ctgggcagct ggagcctggg ggactggggc | 60 |
| gccgaggcgt gcacatgctc gcccagccac ccccaggacg ccttctgcaa ctccgacatc | 120 |
| gtgatccggg ccaatgtgac ggggaagaag ctggtaaagg aggggcccaa cggcacgctg | 180 |
| gtctacacca tcaagcagat gaagatgtac cgaggcttca ccaagatgcc ccatgtgcag | 240 |
| tacatccaca cggaagcttc cgagagtctc tgtggcctta atctgacggt caacaagtac | 300 |
| cagtacctgc tgacaggtcg cgtctataat ggcacgatgt acacggggct gtgcaacttc | 360 |
| gtggagaggt gggaccagct cacccctctcc cagcgcaagg ggctgaacta tcggtatcac | 420 |
| ctgggttgta actgcaagat caagtcctgc tactacctgc cttgctttgt gacttccaag | 480 |
| aacgagtgtc tctggaccga catgctctcc aatttcggtt accctggcta ccagtccaaa | 540 |
| cactacgcct gcatccggca aagggcggc tactgcagct ggtaccgagg atgggccccc | 600 |
| ccggataaaa gcatcatcaa tgccacagac ccccaccacc atcaccatca t | 651 |

<210> SEQ ID NO 31
<211> LENGTH: 651
<212> TYPE: DNA
<213> ORGANISM: Homo sapiens

<400> SEQUENCE: 31

| | | | | | |
|---|---|---|---|---|---|
| atgacccctt | ggctcgggct | catcgtgctc | ctgggcagct | ggagcctggg | ggactggggc | 60 |
| gccgaggcgt | gcacatgctc | gcccagccac | ccccaggacg | ccttctgcaa | ctccgacatc | 120 |
| gtgatccggg | ccaatgtgac | ggggaagaag | ctggtaaagg | aggggcccaa | cggcacgctg | 180 |
| gtctacacca | tcaagcagat | gaagatgtac | cgaggcttca | ccaagatgcc | ccatgtgcag | 240 |
| tacatccaca | cggaagcttc | cgagagtctc | tgtggcctta | atctgacggt | caacaagtac | 300 |
| cagtacctgc | tgacaggtcg | cgtctatgat | ggcaagatgt | acacggggct | gtgcaacttc | 360 |
| gtggagaggt | gggaccagct | caccctctcc | cagcgcaagg | ggctgaacta | tacgtatcac | 420 |
| ctgggttgta | actgcaagat | caagtcctgc | tactacctgc | cttgctttgt | gacttccaag | 480 |
| aacgagtgtc | tctggaccga | catgctctcc | aatttcggtt | accctggcta | ccagtccaaa | 540 |
| cactacgcct | gcatccggca | gaagggcggc | tactgcagct | ggtaccgagg | atgggccccc | 600 |
| ccggataaaa | gcatcatcaa | tgccacagac | ccccaccacc | atcaccatca | t | 651 |

<210> SEQ ID NO 32
<211> LENGTH: 651
<212> TYPE: DNA
<213> ORGANISM: Homo sapiens

<400> SEQUENCE: 32

| | | | | | |
|---|---|---|---|---|---|
| atgacccctt | ggctcgggct | catcgtgctc | ctgggcagct | ggagcctggg | ggactggggc | 60 |
| gccgaggcgt | gcacatgctc | gcccagccac | ccccaggacg | ccttctgcaa | ctccgacatc | 120 |
| gtgatccggg | ccaatgtgac | ggggaagaag | ctggtaaagg | aggggcccct | cggcacgctg | 180 |
| gtctacacca | tcaagcagat | gaagatgtac | cgaggcttca | ccaagatgcc | caatgtgacg | 240 |
| tacatccaca | cggaagcttc | cgagagtctc | tgtggcctta | atctgacggt | caacaagtac | 300 |
| cagtacctgc | tgacaggtcg | cgtctatgat | ggcaagatgt | acacggggct | gtgcaacttc | 360 |
| gtggagaggt | gggaccagct | caccctctcc | cagcgcaagg | ggctgaacta | tacgtatcac | 420 |
| ctgggttgta | actgcaagat | caagtcctgc | tactacctgc | cttgctttgt | gacttccaag | 480 |
| aacgagtgtc | tctggaccga | catgctctcc | aatttcactt | accctggcta | ccagtccaaa | 540 |
| cactacgcct | gcatccggca | gaagggcggc | tactgcagct | ggtaccgagg | atgggccccc | 600 |
| ccggataaaa | gcatcatcaa | tgccacagac | ccccaccacc | atcaccatca | t | 651 |

<210> SEQ ID NO 33
<211> LENGTH: 651
<212> TYPE: DNA
<213> ORGANISM: Homo sapiens

<400> SEQUENCE: 33

| | | | | | |
|---|---|---|---|---|---|
| atgacccctt | ggctcgggct | catcgtgctc | ctgggcagct | ggagcctggg | ggactggggc | 60 |
| gccgaggcgt | gcacatgctc | gcccagccac | ccccaggacg | ccttctgcaa | ctccgacatc | 120 |
| gtgatccggg | ccaatgtgac | ggggaagaag | ctggtaaagg | aggggcccct | cggcacgctg | 180 |
| gtctacacca | tcaagcagat | gaagatgtac | cgaggcttca | ccaagatgcc | ccatgtgcag | 240 |
| tacatccaca | cggaagcttc | cgagagtctc | tgtggcctta | atctgacggt | caacaagtac | 300 |

```
cagtacctgc tgacaggtcg cgtctataat ggcacgatgt acacgggct gtgcaacttc      360 gtggagaggt gggaccagct caccctctcc cagcgcaagg ggctgaacta tacgtatcac      420
ctgggttgta actgcaagat caagtcctgc tactacctgc cttgctttgt gacttccaag      480
aacgagtgtc tctggaccga catgctctcc aatttcggtt accctggcta ccagtccaaa      540
cactacgcct gcatccggca aagggcggc tactgcagct ggtaccgagg atgggccccc      600
ccggataaaa gcatcatcaa tgccacagac ccccaccacc atcaccatca t              651
```

<210> SEQ ID NO 34
<211> LENGTH: 651
<212> TYPE: DNA
<213> ORGANISM: Homo sapiens

<400> SEQUENCE: 34

```
atgacccctt ggctcgggct catcgtgctc ctgggcagct ggagcctggg ggactggggc       60
gccgaggcgt gcacatgctc gcccagccac cccaggacg ccttctgcaa ctccgacatc      120
gtgatccggg ccaatgtgac ggggaagaag ctggtaaagg aggggcccctt cggcacgctg    180 gtctacacca tcaagcagat gaagatgtac cgaggcttca ccaagatgcc ccatgtgcag     240
tacatccaca cggaagcttc cgagagtctc tgtggcctta atctgacggt caacaagtac     300
cagtacctgc tgacaggtcg cgtctataat ggcacgatgt acacgggct gtgcaacttc      360 gtggagaggt gggaccagct caccctctcc cagcgcaagg ggctgaacta tcggtatcac     420
ctgggttgta actgcaagat caagtcctgc tactacctgc cttgctttgt gacttccaag     480
aacgagtgtc tctggaccga catgctctcc aatttcactt accctggcta ccagtccaaa    540
cactacgcct gcatccggca aagggcggc tactgcagct ggtaccgagg atgggccccc      600
ccggataaaa gcatcatcaa tgccacagac ccccaccacc atcaccatca t              651
```

<210> SEQ ID NO 35
<211> LENGTH: 651
<212> TYPE: DNA
<213> ORGANISM: Homo sapiens

<400> SEQUENCE: 35

```
atgacccctt ggctcgggct catcgtgctc ctgggcagct ggagcctggg ggactggggc       60
gccgaggcgt gcacatgctc gcccagccac cccaggacg ccttctgcaa ctccgacatc      120
gtgatccggg ccaatgtgac ggggaagaag ctggtaaagg aggggcccctt cggcacgctg    180 gtctacacca tcaagcagat gaagatgtac cgaggcttca ccaagatgcc ccatgtgcag     240
tacatccaca cggaagcttc cgagagtctc tgtggcctta atctgacggt caacaagtac     300
cagtacctgc tgacaggtcg cgtctatgat ggcaagatgt acacgggct gtgcaacttc      360 gtggagaggt gggaccagct caccctctcc cagcgcaagg ggctgaacta tacgtatcac     420
ctgggttgta actgcaagat caagtcctgc tactacctgc cttgctttgt gacttccaag     480
aacgagtgtc tctggaccga catgctctcc aatttcactt accctggcta ccagtccaaa    540
cactacgcct gcatccggca aagggcggc tactgcagct ggtaccgagg atgggccccc      600
ccggataaaa gcatcatcaa tgccacagac ccccaccacc atcaccatca t              651
```

<210> SEQ ID NO 36
<211> LENGTH: 651
<212> TYPE: DNA
<213> ORGANISM: Homo sapiens

<400> SEQUENCE: 36

```
atgacccctt ggctcgggct catcgtgctc ctgggcagct ggagcctggg ggactggggc    60
gccgaggcgt gcacatgctc gcccagccac ccccaggacg ccttctgcaa ctccgacatc   120
gtgatccggg ccagcgtggt ggggaagaag ctggtaaagg aggggcccaa cggcacgctg   180
gtctacacca tcaagcagat gaagatgtac cgaggcttca ccaagatgcc ccatgtgcag   240
tacatccaca cggaagcttc cgagagtctc tgtggcctta atctgacggt caacaagtac   300
cagtacctgc tgacaggtcg cgtctataat ggcacgatgt acacggggct gtgcaacttc   360
gtggagaggt gggaccagct caccctctcc cagcgcaagg ggctgaacta tacgtatcac   420
ctgggttgta actgcaagat caagtcctgc tactacctgc cttgctttgt gacttccaag   480
aacgagtgtc tctggaccga catgctctcc aatttcggtt accctggcta ccagtccaaa   540
cactacgcct gcatccggca aagggcggc tactgcagct ggtaccgagg atgggccccc   600
ccggataaaa gcatcatcaa tgccacagac ccccaccacc atcaccatca t            651
```

<210> SEQ ID NO 37
<211> LENGTH: 651
<212> TYPE: DNA
<213> ORGANISM: Homo sapiens

<400> SEQUENCE: 37

```
atgacccctt ggctcgggct catcgtgctc ctgggcagct ggagcctggg ggactggggc    60
gccgaggcgt gcacatgctc gcccagccac ccccaggacg ccttctgcaa ctccgacatc   120
gtgatccggg ccagcgtggt ggggaagaag ctggtaaagg aggggcccaa cggcacgctg   180
gtctacacca tcaagcagat gaagatgtac cgaggcttca ccaagatgcc caatgtgacg   240
tacatccaca cggaagcttc cgagagtctc tgtggcctta atctgacggt caacaagtac   300
cagtacctgc tgacaggtcg cgtctatgat ggcaagatgt acacggggct gtgcaacttc   360
gtggagaggt gggaccagct caccctctcc cagcgcaagg ggctgaacta tacgtatcac   420
ctgggttgta actgcaagat caagtcctgc tactacctgc cttgctttgt gacttccaag   480
aacgagtgtc tctggaccga catgctctcc aatttcggtt accctggcta ccagtccaaa   540
cactacgcct gcatccggca aagggcggc tactgcagct ggtaccgagg atgggccccc   600
ccggataaaa gcatcatcaa tgccacagac ccccaccacc atcaccatca t            651
```

<210> SEQ ID NO 38
<211> LENGTH: 651
<212> TYPE: DNA
<213> ORGANISM: Homo sapiens

<400> SEQUENCE: 38

```
atgacccctt ggctcgggct catcgtgctc ctgggcagct ggagcctggg ggactggggc    60
gccgaggcgt gcacatgctc gcccagccac ccccaggacg ccttctgcaa ctccgacatc   120
gtgatccggg ccaaggtggt ggggaagaat ctgacaaagg agggaacctt caccacgctg   180
gtctacacca tcaagcagat gaagatgtac cgaggcttca ccaagatgcc ccatgtgcag   240
tacatccaca cggaagcttc cgagagtctc tgtggcctta atctgacggt caacaagtac   300
cagtacctgc tgacaggtcg cgtctataat ggcacgatgt acacggggct gtgcaacttc   360
gtggagaggt gggaccagct caccctctcc cagcgcaagg ggctgaacta tacgtatcac   420
ctgggttgta actgcaagat caagtcctgc tactacctgc cttgctttgt gacttccaag   480
aacgagtgtc tctggaccga catgctctcc aatttcggtt accctggcta ccagtccaaa   540
```

| | |
|---|---|
| cactacgcct gcatccggca aagggcggc tactgcagct ggtaccgagg atgggccccc | 600 |
| ccggataaaa gcatcatcaa tgccacagac ccccaccacc atcaccatca t | 651 |

<210> SEQ ID NO 39
<211> LENGTH: 651
<212> TYPE: DNA
<213> ORGANISM: Homo sapiens

<400> SEQUENCE: 39

| | |
|---|---|
| atgacccctt ggctcgggct catcgtgctc ctgggcagct ggagcctggg ggactggggc | 60 |
| gccgaggcgt gcacatgctc gcccagccac ccccaggacg ccttctgcaa ctccgacatc | 120 |
| gtgatccggg ccaaggtggt ggggaagaat ctgacaaagg aggggcccctt cggcacgctg | 180 |
| gtctacacca tcaagcagat gaagatgtac cgaggcttca ccaagatgcc caatgtgacg | 240 |
| tacatccaca cggaagcttc cgagagtctc tgtggcctta atctgacggt caacaagtac | 300 |
| cagtacctgc tgacaggtcg cgtctatgat ggcaagatgt acgggggct gtgcaacttc | 360 |
| gtggagaggt gggaccagct caccctctcc cagcgcaagg ggctgaacta tacgtatcac | 420 |
| ctgggttgta actgcaagat caagtcctgc tactacctgc cttgctttgt gacttccaag | 480 |
| aacgagtgtc tctggaccga catgctctcc aatttcactt accctggcta ccagtccaaa | 540 |
| cactacgcct gcatccggca aagggcggc tactgcagct ggtaccgagg atgggccccc | 600 |
| ccggataaaa gcatcatcaa tgccacagac ccccaccacc atcaccatca t | 651 |

<210> SEQ ID NO 40
<211> LENGTH: 651
<212> TYPE: DNA
<213> ORGANISM: Homo sapiens

<400> SEQUENCE: 40

| | |
|---|---|
| atgacccctt ggctcgggct catcgtgctc ctgggcagct ggagcctggg ggactggggc | 60 |
| gccgaggcgt gcacatgctc gcccagccac ccccaggacg ccttctgcaa ctccgacatc | 120 |
| gtgatccggg ccaaggtggt ggggaagaat ctgacaaagg aggggcccctt cggcacgctg | 180 |
| gtctacacca tcaagcagat gaagatgtac cgaggcttca ccaagatgcc ccatgtgcag | 240 |
| tacatccaca cggaagcttc cgagagtctc tgtggcctta atctgacggt caacaagtac | 300 |
| cagtacctgc tgacaggtcg cgtctataat ggcacgatgt acgggggct gtgcaacttc | 360 |
| gtggagaggt gggaccagct caccctctcc cagcgcaagg ggctgaacta tacgtatcac | 420 |
| ctgggttgta actgcaagat caagtcctgc tactacctgc cttgctttgt gacttccaag | 480 |
| aacgagtgtc tctggaccga catgctctcc aatttcggtt accctggcta ccagtccaaa | 540 |
| cactacgcct gcatccggca aagggcggc tactgcagct ggtaccgagg atgggccccc | 600 |
| ccggataaaa gcatcatcaa tgccacagac ccccaccacc atcaccatca t | 651 |

<210> SEQ ID NO 41
<211> LENGTH: 651
<212> TYPE: DNA
<213> ORGANISM: Homo sapiens

<400> SEQUENCE: 41

| | |
|---|---|
| atgacccctt ggctcgggct catcgtgctc ctgggcagct ggagcctggg ggactggggc | 60 |
| gccgaggcgt gcacatgctc gcccagccac ccccaggacg ccttctgcaa ctccgacatc | 120 |
| gtgatccggg ccaaggtggt ggggaagaat ctgacaaagg aggggcccctt cggcacgctg | 180 |
| gtctacacca tcaagcagat gaagatgtac cgaggcttca ccaagatgcc ccatgtgcag | 240 |

```
tacatccaca cggaagcttc cgagagtctc tgtggcctta atctgacggt caacaagtac      300
cagtacctgc tgacaggtcg cgtctataat ggcacgatgt acacgggcgt gtgcaacttc      360
gtggagaggt gggaccagct caccctctcc cagcgcaagg ggctgaacta tacgtatcac      420
ctgggttgta actgcaagat caagtcctgc tactacctgc cttgctttgt gacttccaag      480
aacgagtgtc tctggaccga catgctctcc aatttcactt accctggcta ccagtccaaa      540
cactacgcct gcatccggca gaagggcggc tactgcagct ggtaccgagg atgggccccc      600
ccggataaaa gcatcatcaa tgccacagac ccccaccacc atcaccatca t              651
```

<210> SEQ ID NO 42
<211> LENGTH: 651
<212> TYPE: DNA
<213> ORGANISM: Homo sapiens

<400> SEQUENCE: 42

```
atgacccctt ggctcgggct catcgtgctc ctgggcagct ggagcctggg ggactggggc       60
gccgaggcgt gcacatgctc gcccagccac ccccaggacg ccttctgcaa ctccgacatc      120
gtgatccggg ccaaggtggt ggggaagaat ctgacaaagg aggggccctt cggcacgctg      180
gtctacacca tcaagcagat gaagatgtac cgaggcttca ccaagatgcc ccatgtgcag      240
tacatccaca cggaagcttc cgagagtctc tgtggcctta atctgacggt caacaagtac      300
cagtacctgc tgacaggtcg cgtctatgat ggcaagatgt acacgggcgt gtgcaacttc      360
gtggagaggt gggaccagct caccctctcc cagcgcaagg ggctgaacta tacgtatcac      420
ctgggttgta actgcaagat caagtcctgc tactacctgc cttgctttgt gacttccaag      480
aacgagtgtc tctggaccga catgctctcc aatttcactt accctggcta ccagtccaaa      540
cactacgcct gcatccggca gaagggcggc tactgcagct ggtaccgagg atgggccccc      600
ccggataaaa gcatcatcaa tgccacagac ccccaccacc atcaccatca t              651
```

<210> SEQ ID NO 43
<211> LENGTH: 651
<212> TYPE: DNA
<213> ORGANISM: Homo sapiens

<400> SEQUENCE: 43

```
atgacccctt ggctcgggct catcgtgctc ctgggcagct ggagcctggg ggactggggc       60
gccgaggcgt gcacatgctc gcccagccac ccccaggacg ccttctgcaa ctccgacatc      120
gtgatccggg ccaaggtggt ggggaagaat ctgacaaagg aggggccctt cggcacgctg      180
gtctacacca tcaagcagat gaagatgtac cgaggcttca ccaagatgcc ccatgtgcag      240
tacatccaca cggaagcttc cgagagtctc tgtggcctta agctggaggt caacaagtac      300
cagtacctgc tgacaggtcg cgtctatgat ggcaagatgt acacgggcgt gtgcaacttc      360
gtggagaggt gggacaatct caccctctcc cagcgcaagg ggctgaacta tacgtatcac      420
ctgggttgta actgcaagat caagtcctgc tactacctgc cttgctttgt gacttccaag      480
aacgagtgtc tctggaccga catgctctcc aatttcactt accctggcta ccagtccaaa      540
cactacgcct gcatccggca gaagggcggc tactgcagct ggtaccgagg atgggccccc      600
ccggataaaa gcatcatcaa tgccacagac ccccaccacc atcaccatca t              651
```

<210> SEQ ID NO 44
<211> LENGTH: 651
<212> TYPE: DNA

<213> ORGANISM: Homo sapiens

<400> SEQUENCE: 44

| | |
|---|---|
| atgacccctt ggctcgggct catcgtgctc ctgggcagct ggagcctggg ggactggggc | 60 |
| gccgaggcgt gcacatgctc gcccagccac ccccaggacg ccttctgcaa ctccgacatc | 120 |
| gtgatccggg ccaaggtggt ggggaagaag ctggtaaagg aggggaactt caccacgctg | 180 |
| gtctacacca tcaagcagat gaagatgtac cgaggcttca ccaagatgcc caatgtgacg | 240 |
| tacatccaca cggaagcttc cgagagtctc tgtggcctta atctgacggt caacaagtac | 300 |
| cagtacctgc tgacaggtcg cgtctatgat ggcaagatgt acacggggct gtgcaacttc | 360 |
| gtggagaggt gggaccagct caccctctcc cagcgcaagg ggctgaacta tacgtatcac | 420 |
| ctgggttgta actgcaagat caagtcctgc tactacctgc cttgctttgt gacttccaag | 480 |
| aacgagtgtc tctggaccga catgctctcc aatttcggtt accctggcta ccagtccaaa | 540 |
| cactacgcct gcatccggca aagggcggc tactgcagct ggtaccgagg atgggccccc | 600 |
| ccggataaaa gcatcatcaa tgccacagac ccccaccacc atcaccatca t | 651 |

<210> SEQ ID NO 45
<211> LENGTH: 651
<212> TYPE: DNA
<213> ORGANISM: Homo sapiens

<400> SEQUENCE: 45

| | |
|---|---|
| atgacccctt ggctcgggct catcgtgctc ctgggcagct ggagcctggg ggactggggc | 60 |
| gccgaggcgt gcacatgctc gcccagccac ccccaggacg ccttctgcaa ctccgacatc | 120 |
| gtgatccggg ccaaggtggt ggggaagaag ctggtaaagg aggggaactt caccacgctg | 180 |
| gtctacacca tcaagcagat gaagatgtac cgaggcttca ccaagatgcc ccatgtgcag | 240 |
| tacatccaca cggaagcttc cgagagtctc tgtggcctta atctgacggt caacaagtac | 300 |
| cagtacctgc tgacaggtcg cgtctatgat ggcaagatgt acacggggct gtgcaacttc | 360 |
| gtggagaggt gggacaatct caccctctcc cagcgcaagg ggctgaacta tacgtatcac | 420 |
| ctgggttgta actgcaagat caagtcctgc tactacctgc cttgctttgt gacttccaag | 480 |
| aacgagtgtc tctggaccga catgctctcc aatttcggtt accctggcta ccagtccaaa | 540 |
| cactacgcct gcatccggca aagggcggc tactgcagct ggtaccgagg atgggccccc | 600 |
| ccggataaaa gcatcatcaa tgccacagac ccccaccacc atcaccatca t | 651 |

<210> SEQ ID NO 46
<211> LENGTH: 651
<212> TYPE: DNA
<213> ORGANISM: Homo sapiens

<400> SEQUENCE: 46

| | |
|---|---|
| atgacccctt ggctcgggct catcgtgctc ctgggcagct ggagcctggg ggactggggc | 60 |
| gccgaggcgt gcacatgctc gcccagccac ccccaggacg ccttctgcaa ctccgacatc | 120 |
| gtgatccggg ccaaggtggt ggggaagaag ctggtaaagg aggggaactt caccacgctg | 180 |
| gtctacacca tcaagcagat gaagatgtac cgaggcttca ccaagatgcc ccatgtgcag | 240 |
| tacatccaca cggaagcttc cgagagtctc tgtggcctta atctgacggt caacaagtac | 300 |
| cagtacctgc tgacaggtcg cgtctataat ggcacgatgt acacggggct gtgcaacttc | 360 |
| gtggagaggt gggaccagct caccctctcc cagcgcaagg ggctgaacta tacgtatcac | 420 |
| ctgggttgta actgcaagat caagtcctgc tactacctgc cttgctttgt gacttccaag | 480 |

```
aacgagtgtc tctggaccga catgctctcc aatttcggtt accctggcta ccagtccaaa    540
cactacgcct gcatccggca gaagggcggc tactgcagct ggtaccgagg atgggccccc    600
ccggataaaa gcatcatcaa tgccacagac ccccaccacc atcaccatca t             651
```

<210> SEQ ID NO 47
<211> LENGTH: 651
<212> TYPE: DNA
<213> ORGANISM: Homo sapiens

<400> SEQUENCE: 47

```
atgaccccttg gctcgggct catcgtgctc ctgggcagct ggagcctggg ggactggggc    60
gccgaggcgt gcacatgctc gcccagccac ccccaggacg ccttctgcaa ctccgacatc    120
gtgatccggg ccaaggtggt ggggaagaag ctggtaaagg aggggaactt caccacgctg    180
gtctacacca tcaagcagat gaagatgtac cgaggcttca ccaagatgcc caatgtgacg    240
tacatccaca cggaagcttc cgagagtctc tgtggcctta atctgacggt caacaagtac    300
cagtacctgc tgacaggtcg cgtctatgat ggcaagatgt acacggggct gtgcaacttc    360
gtggagaggt gggaccagct caccctctcc cagcgcaagg ggctgaacta tcggtatcac    420
ctgggttgta actgcaagat caagtcctgc tactacctgc cttgctttgt gacttccaag    480
aacgagtgtc tctggaccga catgctctcc aatttcactt accctggcta ccagtccaaa    540
cactacgcct gcatccggca gaagggcggc tactgcagct ggtaccgagg atgggccccc    600
ccggataaaa gcatcatcaa tgccacagac ccccaccacc atcaccatca t             651
```

<210> SEQ ID NO 48
<211> LENGTH: 651
<212> TYPE: DNA
<213> ORGANISM: Homo sapiens

<400> SEQUENCE: 48

```
atgaccccttg gctcgggct catcgtgctc ctgggcagct ggagcctggg ggactggggc    60
gccgaggcgt gcacatgctc gcccagccac ccccaggacg ccttctgcaa ctccgacatc    120
gtgatccggg ccaaggtggt ggggaagaag ctggtaaagg aggggaactt caccacgctg    180
gtctacacca tcaagcagat gaagatgtac cgaggcttca ccaagatgcc ccatgtgcag    240
tacatccaca cggaagcttc cgagagtctc tgtggcctta agctggaggt caacaagtac    300
cagtacctgc tgacaggtcg cgtctatgat ggcaagatgt acacggggct gtgcaacttc    360
gtggagaggt gggacaatct caccctctcc cagcgcaagg ggctgaacta tacgtatcac    420
ctgggttgta actgcaagat caagtcctgc tactacctgc cttgctttgt gacttccaag    480
aacgagtgtc tctggaccga catgctctcc aatttcactt accctggcta ccagtccaaa    540
cactacgcct gcatccggca gaagggcggc tactgcagct ggtaccgagg atgggccccc    600
ccggataaaa gcatcatcaa tgccacagac ccccaccacc atcaccatca t             651
```

<210> SEQ ID NO 49
<211> LENGTH: 651
<212> TYPE: DNA
<213> ORGANISM: Homo sapiens

<400> SEQUENCE: 49

```
atgaccccttg gctcgggct catcgtgctc ctgggcagct ggagcctggg ggactggggc    60
gccgaggcgt gcacatgctc gcccagccac ccccaggacg ccttctgcaa ctccgacatc    120
```

```
gtgatccggg ccaaggtggt ggggaagaag ctggtaaagg aggggcccct cggcacgctg      180
gtctacacca tcaagcagat gaagatgtac cgaggcttca ccaagatgcc caatgtgacg      240
tacatccaca cggaagcttc cgagagtctc tgtggcctta atctgacggt caacaagtac      300
cagtacctgc tgacaggtcg cgtctatgat ggcaagatgt acacggggct gtgcaacttc      360
gtggagaggt gggaccagct caccctctcc cagcgcaagg ggctgaacta tacgtatcac      420
ctgggttgta actgcaagat caagtcctgc tactacctgc cttgctttgt gacttccaag      480
aacgagtgtc tctggaccga catgctctcc aatttcactt accctggcta ccagtccaaa      540
cactacgcct gcatccggca aagggcggc tactgcagct ggtaccgagg atgggccccc      600
ccggataaaa gcatcatcaa tgccacagac ccccaccacc atcaccatca t              651

<210> SEQ ID NO 50
<211> LENGTH: 2391
<212> TYPE: DNA
<213> ORGANISM: Homo sapiens

<400> SEQUENCE: 50
atgacccctt ggctcgggct catcgtgctc ctgggcagct ggagcctggg ggactggggc       60
gccgaggcgt gcacatgctc gcccagccac ccccaggacg ccttctgcaa ctccgacatc      120
gtgatccggg ccaaggtggt ggggaagaag ctggtaaagg aggggcccct cggcacgctg      180
gtctacacca tcaagcagat gaagatgtac cgaggcttca ccaagatgcc caatgtgacg      240
tacatccaca cggaagcttc cgagagtctc tgtggcctta atctgacggt caacaagtac      300
cagtacctgc tgacaggtcg cgtctataat ggcacgatgt acacggggct gtgcaacttc      360
gtggagaggt gggaccagct caccctctcc cagcgcaagg ggctgaacta tacgtatcac      420
ctgggttgta actgcaagat caagtcctgc tactacctgc cttgctttgt gacttccaag      480
aacgagtgtc tctggaccga catgctctcc aatttcggtt accctggcta ccagtccaaa      540
cactacgcct gcatccggca aagggcggc tactgcagct ggtaccgagg atgggccccc      600
ccggataaaa gcatcatcaa tgccacagac ccgatgcac acaagagtga ggttgctcat      660
cgatttaaag atttgggaga agaaaatttc aaagccttgg tgttgattgc ctttgctcag      720
tatcttcagc agtgtccatt tgaagatcat gtaaaattag tgaatgaagt aactgaattt      780
gcaaaaacat gtgttgctga tgagtcagct gaaaattgtg acaaatcact tcataccctt      840
tttggagaca aattatgcac agttgcaact cttcgtgaaa cctatggtga aatggctgac      900
tgctgtgcaa acaagaaacc tgagagaaat gaatgcttct gcaacacaa agatgacaac      960 ccaaacctcc cccgattggt gagaccagag gttgatgtga tgtgcactgc ttttcatgac     1020
aatgaagaga cattttttgaa aaaatactta tatgaaattg ccagaagaca tccttacttt     1080
tatgccccgg aactcctttt ctttgctaaa aggtataaag ctgcttttac agaatgttgc     1140
caagctgctg ataaagctgc ctgcctgttg ccaaagctcg atgaacttcg ggatgaaggg     1200
aaggcttcgt ctgccaaaca gagactcaag tgtgccagtc tccaaaaatt tggagaaaga     1260
gctttcaaag catgggcagt agctcgcctg agccagagat ttcccaaagc tgagtttgca     1320
gaagtttcca gttagtgac agatcttacc aaagtccaca cggaatgctg ccatggagat     1380
ctgcttgaat gtgctgatga cagggcggac cttgccaagt atatctgtga aaatcaagat     1440
tcgatctcca gtaaactgaa ggaatgctgt gaaaaacctc tgttggaaaa atcccactgc     1500
attgccgaag tggaaaatga tgagatgcct gctgacttgc cttcattagc tgctgatttt     1560
gttgaaagta aggatgtttg caaaaactat gctgaggcaa aggatgtctt cctgggcatg     1620
```

```
tttttgtatg aatatgcaag aaggcatcct gattactctg tcgtgctgct gctgagactt   1680
gccaagacat atgaaaccac tctagagaag tgctgtgccg ctgcagatcc tcatgaatgc   1740
tatgccaaag tgttcgatga atttaaacct cttgtggaag agcctcagaa tttaatcaaa   1800
caaaattgtg agcttttga gcagcttgga gagtacaaat tccagaatgc gctattagtt   1860
cgttacacca agaaagtacc ccaactgtca actccaactc ttatcgaggt ctcaagaaac   1920
ctaggaaaag tgggcagcaa atgttgtaaa catcctgaag caaaaagaat gccctgtgca   1980
gaagactatc tatccgtggt cctgaaccag ttatgtgtgt tgcatgagaa aacgccagta   2040
agtgacagag tcaccaaatg ctgcacagaa tccttggtga acaggcgacc atgcttttca   2100
gctctggaag tcgatgaaac atacgttccc aaagagttta cagctaacac attcaccttc   2160
catgcagata tatgcacact ttctgagaag gagagacaaa tcaagaaaca aactgtgctt   2220
gttgagctcg tgaaacacaa gcccaaggca acaaaagagc aactgaaagc tgccatggat   2280
gatttcgcag cttttgtaga gaagtgctgc aaggctgacg ataaggagac ctgctttagc   2340
gaggagggta aaaaacttgt tgcggccagt caggccgcct taggcttatg a             2391
```

<210> SEQ ID NO 51
<211> LENGTH: 773
<212> TYPE: PRT
<213> ORGANISM: Homo sapiens

<400> SEQUENCE: 51

```
Cys Thr Cys Ser Pro Ser His Pro Gln Asp Ala Phe Cys Asn Ser Asp
1               5                   10                  15

Ile Val Ile Arg Ala Lys Val Val Gly Lys Lys Leu Val Lys Glu Gly
                20                  25                  30

Pro Phe Gly Thr Leu Val Tyr Thr Ile Lys Gln Met Lys Met Tyr Arg
            35                  40                  45

Gly Phe Thr Lys Met Pro Asn Val Thr Tyr Ile His Thr Glu Ala Ser
        50                  55                  60

Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro Asp Ala His Lys
            180                 185                 190

Ser Glu Val Ala His Arg Phe Lys Asp Leu Gly Glu Glu Asn Phe Lys
        195                 200                 205

Ala Leu Val Leu Ile Ala Phe Ala Gln Tyr Leu Gln Gln Cys Pro Phe
    210                 215                 220

Glu Asp His Val Lys Leu Val Asn Glu Val Thr Glu Phe Ala Lys Thr
225                 230                 235                 240
```

-continued

```
Cys Val Ala Asp Glu Ser Ala Glu Asn Cys Asp Lys Ser Leu His Thr
                245                 250                 255
Leu Phe Gly Asp Lys Leu Cys Thr Val Ala Thr Leu Arg Glu Thr Tyr
            260                 265                 270
Gly Glu Met Ala Asp Cys Cys Ala Lys Gln Glu Pro Glu Arg Asn Glu
        275                 280                 285
Cys Phe Leu Gln His Lys Asp Asp Asn Pro Asn Leu Pro Arg Leu Val
    290                 295                 300
Arg Pro Glu Val Asp Val Met Cys Thr Ala Phe His Asp Asn Glu Glu
305                 310                 315                 320
Thr Phe Leu Lys Lys Tyr Leu Tyr Glu Ile Ala Arg Arg His Pro Tyr
                325                 330                 335
Phe Tyr Ala Pro Glu Leu Leu Phe Phe Ala Lys Arg Tyr Lys Ala Ala
            340                 345                 350
Phe Thr Glu Cys Cys Gln Ala Ala Asp Lys Ala Ala Cys Leu Leu Pro
        355                 360                 365
Lys Leu Asp Glu Leu Arg Asp Glu Gly Lys Ala Ser Ser Ala Lys Gln
    370                 375                 380
Arg Leu Lys Cys Ala Ser Leu Gln Lys Phe Gly Glu Arg Ala Phe Lys
385                 390                 395                 400
Ala Trp Ala Val Ala Arg Leu Ser Gln Arg Phe Pro Lys Ala Glu Phe
                405                 410                 415
Ala Glu Val Ser Lys Leu Val Thr Asp Leu Thr Lys Val His Thr Glu
            420                 425                 430
Cys Cys His Gly Asp Leu Leu Glu Cys Ala Asp Asp Arg Ala Asp Leu
        435                 440                 445
Ala Lys Tyr Ile Cys Glu Asn Gln Asp Ser Ile Ser Ser Lys Leu Lys
    450                 455                 460
Glu Cys Cys Glu Lys Pro Leu Leu Glu Lys Ser His Cys Ile Ala Glu
465                 470                 475                 480
Val Glu Asn Asp Glu Met Pro Ala Asp Leu Pro Ser Leu Ala Ala Asp
                485                 490                 495
Phe Val Glu Ser Lys Asp Val Cys Lys Asn Tyr Ala Glu Ala Lys Asp
            500                 505                 510
Val Phe Leu Gly Met Phe Leu Tyr Glu Tyr Ala Arg Arg His Pro Asp
        515                 520                 525
Tyr Ser Val Val Leu Leu Leu Arg Leu Ala Lys Thr Tyr Glu Thr Thr
    530                 535                 540
Leu Glu Lys Cys Cys Ala Ala Ala Asp Pro His Glu Cys Tyr Ala Lys
545                 550                 555                 560
Val Phe Asp Glu Phe Lys Pro Leu Val Glu Glu Pro Gln Asn Leu Ile
                565                 570                 575
Lys Gln Asn Cys Glu Leu Phe Glu Gln Leu Gly Glu Tyr Lys Phe Gln
            580                 585                 590
Asn Ala Leu Leu Val Arg Tyr Thr Lys Lys Val Pro Gln Leu Ser Thr
        595                 600                 605
Pro Thr Leu Ile Glu Val Ser Arg Asn Leu Gly Lys Val Gly Ser Lys
    610                 615                 620
Cys Cys Lys His Pro Glu Ala Lys Arg Met Pro Cys Ala Glu Asp Tyr
625                 630                 635                 640
Leu Ser Val Val Leu Asn Gln Leu Cys Val Leu His Glu Lys Thr Pro
                645                 650                 655
```

-continued

```
Val Ser Asp Arg Val Thr Lys Cys Cys Thr Glu Ser Leu Val Asn Arg
            660                 665                 670

Arg Pro Cys Phe Ser Ala Leu Glu Val Asp Glu Thr Tyr Val Pro Lys
        675                 680                 685

Glu Phe Thr Ala Asn Thr Phe Thr Phe His Ala Asp Ile Cys Thr Leu
    690                 695                 700

Ser Glu Lys Glu Arg Gln Ile Lys Lys Gln Thr Val Leu Val Glu Leu
705                 710                 715                 720

Val Lys His Lys Pro Lys Ala Thr Lys Glu Gln Leu Lys Ala Ala Met
            725                 730                 735

Asp Asp Phe Ala Ala Phe Val Glu Lys Cys Cys Lys Ala Asp Asp Lys
        740                 745                 750

Glu Thr Cys Phe Ser Glu Glu Gly Lys Lys Leu Val Ala Ala Ser Gln
    755                 760                 765

Ala Ala Leu Gly Leu
    770

<210> SEQ ID NO 52
<211> LENGTH: 419
<212> TYPE: PRT
<213> ORGANISM: Homo sapiens

<400> SEQUENCE: 52

Cys Thr Cys Ser Pro Ser His Pro Gln Asp Ala Phe Cys Asn Ser Asp
1               5                   10                  15

Ile Val Ile Arg Ala Ser Val Val Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Lys Leu Glu Val Asn Lys Tyr Gln Tyr Leu
65                  70                  75                  80

Leu Thr Gly Arg Val Tyr Asp Gly Lys Met Tyr Thr Gly Leu Cys Asn
            85                  90                  95

Phe Val Glu Arg Trp Asp Gln Leu Thr Leu Ser Gln Arg Lys Gly Leu
        100                 105                 110

Asn Tyr Arg Tyr His Leu Gly Cys Asn Cys Lys Ile Lys Ser Cys Tyr
    115                 120                 125

Tyr Leu Pro Cys Phe Val Thr Ser Lys Asn Glu Cys Leu Trp Thr Asp
130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
            165                 170                 175

Pro Pro Asp Lys Ser Ile Ile Asn Ala Thr Asp Pro Gly Gly Gly Gly
        180                 185                 190

Asp Lys Thr His Thr Cys Pro Pro Cys Pro Ala Pro Glu Leu Leu Gly
    195                 200                 205

Gly Pro Ser Val Phe Leu Phe Pro Pro Lys Pro Lys Asp Thr Leu Met
210                 215                 220

Ile Ser Arg Thr Pro Glu Val Thr Cys Val Val Val Asp Val Ser His
225                 230                 235                 240

Glu Asp Pro Glu Val Lys Phe Asn Trp Tyr Val Asp Gly Val Glu Val
            245                 250                 255
```

His Asn Ala Lys Thr Lys Pro Arg Glu Glu Gln Tyr Asn Ser Thr Tyr
            260                 265                 270

Arg Val Val Ser Val Leu Thr Val Leu His Gln Asp Trp Leu Asn Gly
                275                 280                 285

Lys Glu Tyr Lys Cys Lys Val Ser Asn Lys Ala Leu Pro Ala Pro Ile
    290                 295                 300

Glu Lys Thr Ile Ser Lys Ala Lys Gly Gln Pro Arg Glu Pro Gln Val
305                 310                 315                 320

Tyr Thr Leu Pro Pro Ser Arg Lys Glu Met Thr Lys Asn Gln Val Ser
                325                 330                 335

Leu Thr Cys Leu Val Lys Gly Phe Tyr Pro Ser Asp Ile Ala Val Glu
            340                 345                 350

Trp Glu Ser Asn Gly Gln Pro Glu Asn Asn Tyr Lys Thr Thr Pro Pro
        355                 360                 365

Val Leu Lys Ser Asp Gly Ser Phe Phe Leu Tyr Ser Lys Leu Thr Val
    370                 375                 380

Asp Lys Ser Arg Trp Gln Gln Gly Asn Val Phe Ser Cys Ser Val Met
385                 390                 395                 400

His Glu Ala Leu His Asn His Tyr Thr Gln Lys Ser Leu Ser Leu Ser
                405                 410                 415

Pro Gly Lys

<210> SEQ ID NO 53
<211> LENGTH: 227
<212> TYPE: PRT
<213> ORGANISM: Homo sapiens

<400> SEQUENCE: 53

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Asp Thr Thr Pro Pro
                165                 170                 175

Val Leu Asp Ser Asp Gly Ser Phe Phe Leu Tyr Ser Asp Leu Thr Val
            180                 185                 190

Asp Lys Ser Arg Trp Gln Gln Gly Asn Val Phe Ser Cys Ser Val Met
        195                 200                 205

-continued

```
His Glu Ala Leu His Asn His Tyr Thr Gln Lys Ser Leu Ser Leu Ser
    210                 215                 220

Pro Gly Lys
225

<210> SEQ ID NO 54
<211> LENGTH: 640
<212> TYPE: PRT
<213> ORGANISM: Homo sapiens

<400> SEQUENCE: 54

Cys Thr Cys Ser Pro Ser His Pro Gln Asp Ala Phe Cys Asn Ser Asp
1               5                   10                  15

Ile Val Ile Arg Ala Lys Val Val Gly Lys Asn Leu Thr Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro Gln Val Gln Leu
            180                 185                 190

Gln Glu Ser Gly Pro Gly Leu Val Lys Pro Ser Gln Thr Leu Ser Leu
        195                 200                 205

Thr Cys Thr Val Ser Gly Gly Ser Ile Ser Ser Gly Asp Tyr Phe Trp
    210                 215                 220

Ser Trp Ile Arg Gln Leu Pro Gly Lys Gly Leu Glu Trp Ile Gly His
225                 230                 235                 240

Ile His Asn Ser Gly Thr Thr Tyr Tyr Asn Pro Ser Leu Lys Ser Arg
                245                 250                 255

Val Thr Ile Ser Val Asp Thr Ser Lys Lys Gln Phe Ser Leu Arg Leu
            260                 265                 270

Ser Ser Val Thr Ala Ala Asp Thr Ala Val Tyr Tyr Cys Ala Arg Asp
        275                 280                 285

Arg Gly Gly Asp Tyr Ala Tyr Gly Met Asp Val Trp Gly Gln Gly Thr
    290                 295                 300

Thr Val Thr Val Ser Ser Ala Ser Thr Lys Gly Pro Ser Val Phe Pro
305                 310                 315                 320

Leu Ala Pro Ser Ser Lys Ser Thr Ser Gly Gly Thr Ala Ala Leu Gly
                325                 330                 335

Cys Leu Val Lys Asp Tyr Phe Pro Glu Pro Val Thr Val Ser Trp Asn
```

```
            340                 345                 350
Ser Gly Ala Leu Thr Ser Gly Val His Thr Phe Pro Ala Val Leu Gln
            355                 360                 365

Ser Ser Gly Leu Tyr Ser Leu Ser Ser Val Val Thr Val Pro Ser Ser
        370                 375                 380

Ser Leu Gly Thr Gln Thr Tyr Ile Cys Asn Val Asn His Lys Pro Ser
385                 390                 395                 400

Asn Thr Lys Val Asp Lys Arg Val Glu Pro Lys Ser Cys Asp Lys Thr
                405                 410                 415

His Thr Cys Pro Pro Cys Pro Ala Pro Glu Leu Leu Gly Gly Pro Ser
            420                 425                 430

Val Phe Leu Phe Pro Pro Lys Pro Lys Asp Thr Leu Met Ile Ser Arg
        435                 440                 445

Thr Pro Glu Val Thr Cys Val Val Val Asp Val Ser His Glu Asp Pro
    450                 455                 460

Glu Val Lys Phe Asn Trp Tyr Val Asp Gly Val Glu Val His Asn Ala
465                 470                 475                 480

Lys Thr Lys Pro Arg Glu Glu Gln Tyr Asn Ser Thr Tyr Arg Val Val
                485                 490                 495

Ser Val Leu Thr Val Leu His Gln Asp Trp Leu Asn Gly Lys Glu Tyr
            500                 505                 510

Lys Cys Lys Val Ser Asn Lys Ala Leu Pro Ala Pro Ile Glu Lys Thr
        515                 520                 525

Ile Ser Lys Ala Lys Gly Gln Pro Arg Glu Pro Gln Val Tyr Thr Leu
    530                 535                 540

Pro Pro Ser Arg Glu Glu Met Thr Lys Asn Gln Val Ser Leu Thr Cys
545                 550                 555                 560

Leu Val Lys Gly Phe Tyr Pro Ser Asp Ile Ala Val Glu Trp Glu Ser
                565                 570                 575

Asn Gly Gln Pro Glu Asn Asn Tyr Lys Thr Thr Pro Pro Val Leu Asp
            580                 585                 590

Ser Asp Gly Ser Phe Phe Leu Tyr Ser Lys Leu Thr Val Asp Lys Ser
        595                 600                 605

Arg Trp Gln Gln Gly Asn Val Phe Ser Cys Ser Val Met His Glu Ala
    610                 615                 620

Leu His Asn His Tyr Thr Gln Lys Ser Leu Ser Leu Ser Pro Gly Lys
625                 630                 635                 640

<210> SEQ ID NO 55
<211> LENGTH: 403
<212> TYPE: PRT
<213> ORGANISM: Homo sapiens

<400> SEQUENCE: 55

Cys Thr Cys Ser Pro Ser His Pro Gln Asp Ala Phe Cys Asn Ser Asp
1               5                   10                  15

Ile Val Ile Arg Ala Lys Val Val Gly Lys Asn Leu Thr Lys Glu Gly
                20                  25                  30

Pro Phe Gly Thr Leu Val Tyr Thr Ile Lys Gln Met Lys Met Tyr Arg
            35                  40                  45

Gly Phe Thr Lys Met Pro His Val Gln Tyr Ile His Thr Glu Ala Ser
        50                  55                  60

Glu Ser Leu Cys Gly Leu Asn Leu Thr Val Asn Lys Tyr Gln Tyr Leu
65                  70                  75                  80
```

```
Leu Thr Gly Arg Val Tyr Asp Gly Lys Met Tyr Thr Gly Leu Cys Asn
                    85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
            115                 120                 125

Tyr Leu Pro Cys Phe Val Thr Ser Lys Asn Glu Cys Leu Trp Thr Asp
130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                    165                 170                 175

Pro Pro Asp Lys Ser Ile Ile Asn Ala Thr Asp Pro Glu Ile Val Leu
            180                 185                 190

Thr Gln Ser Pro Gly Thr Leu Ser Leu Ser Pro Gly Glu Arg Ala Thr
            195                 200                 205

Leu Ser Cys Arg Ala Ser Gln Gly Ile Ser Arg Ser Glu Leu Ala Trp
            210                 215                 220

Tyr Gln Gln Lys Pro Gly Gln Ala Pro Ser Leu Leu Ile Tyr Gly Ala
225                 230                 235                 240

Ser Ser Arg Ala Thr Gly Ile Pro Asp Arg Phe Ser Gly Ser Gly Ser
                    245                 250                 255

Gly Thr Asp Phe Thr Leu Thr Ile Ser Arg Leu Glu Pro Glu Asp Phe
            260                 265                 270

Ala Val Tyr Tyr Cys Gln Gln Phe Gly Ser Ser Pro Trp Thr Phe Gly
            275                 280                 285

Gln Gly Thr Lys Val Glu Ile Lys Arg Thr Val Ala Ala Pro Ser Val
290                 295                 300

Phe Ile Phe Pro Pro Ser Asp Glu Gln Leu Lys Ser Gly Thr Ala Ser
305                 310                 315                 320

Val Val Cys Leu Leu Asn Asn Phe Tyr Pro Arg Glu Ala Lys Val Gln
                    325                 330                 335

Trp Lys Val Asp Asn Ala Leu Gln Ser Gly Asn Ser Gln Glu Ser Val
            340                 345                 350

Thr Glu Gln Asp Ser Lys Asp Ser Thr Tyr Ser Leu Ser Ser Thr Leu
            355                 360                 365

Thr Leu Ser Lys Ala Asp Tyr Glu Lys His Lys Val Tyr Ala Cys Glu
            370                 375                 380

Val Thr His Gln Gly Leu Ser Ser Pro Val Thr Lys Ser Phe Asn Arg
385                 390                 395                 400

Gly Glu Cys

<210> SEQ ID NO 56
<211> LENGTH: 405
<212> TYPE: PRT
<213> ORGANISM: Homo sapiens

<400> SEQUENCE: 56

Cys Thr Cys Ser Pro Ser His Pro Gln Asp Ala Phe Cys Asn Ser Asp
1               5                   10                  15

Ile Val Ile Arg Ala Lys Val Val Gly Lys Lys Leu Val Lys Glu Gly
            20                  25                  30

Pro Phe Gly Thr Leu Val Tyr Thr Ile Lys Gln Met Lys Met Tyr Arg
            35                  40                  45
```

```
Gly Phe Thr Lys Met Pro Asn Val Thr Tyr Ile His Thr Glu Ala Ser
     50                  55                  60

Glu Ser Leu Cys Gly Leu Asn Leu Thr Val Asn Lys Tyr Gln Tyr Leu
 65                  70                  75                  80

Leu Thr Gly Arg Val Tyr Asn Gly Thr Met Tyr Thr Gly Leu Cys Asn
                 85                  90                  95

Phe Val Glu Arg Trp Asp Gln Leu Thr Leu Ser Gln Arg Lys Gly Leu
                100                 105                 110

Asn Tyr Thr Tyr His Leu Gly Cys Asn Cys Lys Ile Lys Ser Cys Tyr
            115                 120                 125

Tyr Leu Pro Cys Phe Val Thr Ser Lys Asn Glu Cys Leu Trp Thr Asp
        130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro Ala Pro Glu Leu
            180                 185                 190

Leu Gly Gly Pro Ser Val Phe Leu Phe Pro Pro Lys Pro Lys Asp Thr
        195                 200                 205

Leu Met Ile Ser Arg Thr Pro Glu Val Thr Cys Val Val Val Asp Val
210                 215                 220

Ser His Glu Asp Pro Glu Val Lys Phe Asn Trp Tyr Val Asp Gly Val
225                 230                 235                 240

Glu Val His Asn Ala Lys Thr Lys Pro Arg Glu Glu Gln Tyr Asn Ser
                245                 250                 255

Thr Tyr Arg Val Val Ser Val Leu Thr Val Leu His Gln Asp Trp Leu
            260                 265                 270

Asn Gly Lys Glu Tyr Lys Cys Lys Val Ser Asn Lys Ala Leu Pro Ala
        275                 280                 285

Pro Ile Glu Lys Thr Ile Ser Lys Ala Lys Gly Gln Pro Arg Glu Pro
    290                 295                 300

Gln Val Thr Thr Leu Pro Pro Ser Arg Glu Glu Met Asn Lys Thr Gln
305                 310                 315                 320

Val Ser Leu Thr Cys Leu Val Lys Gly Phe Tyr Pro Ser Asp Ile Ala
                325                 330                 335

Val Glu Trp Glu Ser Asn Gly Gln Pro Glu Asn Asn Tyr Asp Thr Thr
                340                 345                 350

Pro Pro Val Leu Asp Ser Asp Gly Ser Phe Phe Leu Tyr Ser Asp Leu
            355                 360                 365

Thr Val Asp Lys Ser Arg Trp Gln Gln Gly Asn Val Phe Ser Cys Ser
        370                 375                 380

Val Met His Glu Ala Leu His Asn His Tyr Thr Gln Lys Ser Leu Ser
385                 390                 395                 400

Leu Ser Pro Gly Lys
                405

<210> SEQ ID NO 57
<211> LENGTH: 779
<212> TYPE: PRT
<213> ORGANISM: Homo sapiens

<400> SEQUENCE: 57

Cys Thr Cys Ser Pro Ser His Pro Gln Asp Ala Phe Cys Asn Ser Asp
 1               5                  10                  15
```

```
Ile Val Ile Arg Ala Lys Val Gly Lys Leu Val Lys Glu Gly
            20              25              30

Pro Phe Gly Thr Leu Val Tyr Thr Ile Lys Gln Met Lys Met Tyr Arg
            35              40              45

Gly Phe Thr Lys Met Pro His Val Gln Tyr Ile His Thr Glu Ala Ser
50              55              60

Glu Ser Leu Cys Gly Leu Lys Leu Glu Val Asn Lys Tyr Gln Tyr Leu
65              70              75              80

Leu Thr Gly Arg Val Tyr Asp Gly Lys Met Tyr Thr Gly Leu Cys Asn
                85              90              95

Phe Val Glu Arg Trp Asp Gln Leu Thr Leu Ser Gln Lys Gly Leu
                100             105             110

Asn Tyr Arg Tyr His Leu Gly Cys Asn Cys Lys Ile Lys Ser Cys Tyr
            115             120             125

Tyr Leu Pro Cys Phe Val Thr Ser Lys Asn Glu Cys Leu Trp Thr Asp
130             135             140

Met Leu Ser Asn Phe Gly Tyr Pro Gly Tyr Gln Ser Lys His Tyr Ala
145             150             155             160

Cys Ile Arg Gln Lys Gly Gly Tyr Cys Ser Trp Tyr Arg Gly Trp Ala
                165             170             175

Pro Pro Asp Lys Ser Ile Ile Asn Ala Thr Asp Pro Asp Ala His Lys
            180             185             190

Ser Glu Val Ala His Arg Phe Lys Asp Leu Gly Glu Glu Asn Phe Lys
            195             200             205

Ala Leu Val Leu Ile Ala Phe Ala Gln Tyr Leu Gln Gln Cys Pro Phe
            210             215             220

Glu Asp His Val Lys Leu Val Asn Glu Val Thr Glu Phe Ala Lys Thr
225             230             235             240

Cys Val Ala Asp Glu Ser Ala Glu Asn Cys Asp Lys Ser Leu His Thr
                245             250             255

Leu Phe Gly Asp Lys Leu Cys Thr Val Ala Thr Leu Arg Glu Thr Tyr
            260             265             270

Gly Glu Met Ala Asp Cys Cys Ala Lys Gln Glu Pro Glu Arg Asn Glu
            275             280             285

Cys Phe Leu Gln His Lys Asp Asp Asn Pro Asn Leu Pro Arg Leu Val
            290             295             300

Arg Pro Glu Val Asp Val Met Cys Thr Ala Phe His Asp Asn Glu Glu
305             310             315             320

Thr Phe Leu Lys Lys Tyr Leu Tyr Glu Ile Ala Arg Arg His Pro Tyr
                325             330             335

Phe Tyr Ala Pro Glu Leu Leu Phe Phe Ala Lys Arg Tyr Lys Ala Ala
            340             345             350

Phe Thr Glu Cys Cys Gln Ala Ala Asp Lys Ala Ala Cys Leu Leu Pro
            355             360             365

Lys Leu Asp Glu Leu Arg Asp Glu Gly Lys Ala Ser Ser Ala Lys Gln
            370             375             380

Arg Leu Lys Cys Ala Ser Leu Gln Lys Phe Gly Glu Arg Ala Phe Lys
385             390             395             400

Ala Trp Ala Val Ala Arg Leu Ser Gln Arg Phe Pro Lys Ala Glu Phe
                405             410             415

Ala Glu Val Ser Lys Leu Val Thr Asp Leu Thr Lys Val His Thr Glu
            420             425             430
```

Cys Cys His Gly Asp Leu Leu Glu Cys Ala Asp Asp Arg Ala Asp Leu
            435                 440                 445

Ala Lys Tyr Ile Cys Glu Asn Gln Asp Ser Ile Ser Ser Lys Leu Lys
    450                 455                 460

Glu Cys Cys Glu Lys Pro Leu Leu Glu Lys Ser His Cys Ile Ala Glu
465                 470                 475                 480

Val Glu Asn Asp Glu Met Pro Ala Asp Leu Pro Ser Leu Ala Ala Asp
                485                 490                 495

Phe Val Glu Ser Lys Asp Val Cys Lys Asn Tyr Ala Glu Ala Lys Asp
                500                 505                 510

Val Phe Leu Gly Met Phe Leu Tyr Glu Tyr Ala Arg Arg His Pro Asp
            515                 520                 525

Tyr Ser Val Val Leu Leu Leu Arg Leu Ala Lys Thr Tyr Glu Thr Thr
    530                 535                 540

Leu Glu Lys Cys Cys Ala Ala Ala Asp Pro His Glu Cys Tyr Ala Lys
545                 550                 555                 560

Val Phe Asp Glu Phe Lys Pro Leu Val Glu Glu Pro Gln Asn Leu Ile
                565                 570                 575

Lys Gln Asn Cys Glu Leu Phe Glu Gln Leu Gly Glu Tyr Lys Phe Gln
                580                 585                 590

Asn Ala Leu Leu Val Arg Tyr Thr Lys Lys Val Pro Gln Val Ser Thr
            595                 600                 605

Pro Thr Leu Val Glu Val Ser Arg Asn Leu Gly Lys Val Gly Ser Lys
    610                 615                 620

Cys Cys Lys His Pro Glu Ala Lys Arg Met Pro Cys Ala Glu Asp Tyr
625                 630                 635                 640

Leu Ser Val Val Leu Asn Gln Leu Cys Val Leu His Glu Lys Thr Pro
                645                 650                 655

Val Ser Asp Arg Val Thr Lys Cys Cys Thr Glu Ser Leu Val Asn Arg
                660                 665                 670

Arg Pro Cys Phe Ser Ala Leu Glu Val Asp Glu Thr Tyr Val Pro Lys
            675                 680                 685

Glu Phe Asn Ala Glu Thr Phe Thr Phe His Ala Asp Ile Cys Thr Leu
    690                 695                 700

Ser Glu Lys Glu Arg Gln Ile Lys Lys Gln Thr Ala Leu Val Glu Leu
705                 710                 715                 720

Val Lys His Lys Pro Lys Ala Thr Lys Glu Gln Leu Lys Ala Val Met
                725                 730                 735

Asp Asp Phe Ala Ala Phe Val Glu Lys Cys Cys Lys Ala Asp Asp Lys
                740                 745                 750

Glu Thr Cys Phe Ala Glu Glu Gly Lys Lys Leu Val Ala Ala Ser Gln
            755                 760                 765

Ala Ala Leu Gly Leu His His His His His His
    770                 775

<210> SEQ ID NO 58
<211> LENGTH: 777
<212> TYPE: PRT
<213> ORGANISM: Homo sapiens

<400> SEQUENCE: 58

Cys Thr Cys Ser Pro Ser His Pro Gln Asp Ala Phe Cys Asn Ser Asp
1               5                   10                  15

Ile Val Ile Arg Ala Ser Val Val Gly Lys Lys Leu Val Lys Glu Gly
            20                  25                  30

```
Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
 50                  55                  60

Glu Ser Leu Cys Gly Leu Lys Leu Glu Val Asn Lys Tyr Gln Tyr Leu
 65                  70                  75                  80

Leu Thr Gly Arg Val Tyr Asp Gly Lys Met Tyr Thr Gly Leu Cys Asn
                 85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
            115                 120                 125

Tyr Leu Pro Cys Phe Val Thr Ser Lys Asn Glu Cys Leu Trp Thr Asp
        130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro Gly Gly Gly Gly
            180                 185                 190

Asp Ala His Lys Ser Glu Val Ala His Arg Phe Lys Asp Leu Gly Glu
            195                 200                 205

Glu Asn Phe Lys Ala Leu Val Leu Ile Ala Phe Ala Gln Tyr Leu Gln
            210                 215                 220

Gln Cys Pro Phe Glu Asp His Val Lys Leu Val Asn Glu Val Thr Glu
225                 230                 235                 240

Phe Ala Lys Thr Cys Val Ala Asp Glu Ser Ala Glu Asn Cys Asp Lys
                245                 250                 255

Ser Leu His Thr Leu Phe Gly Asp Lys Leu Cys Thr Val Ala Thr Leu
            260                 265                 270

Arg Glu Thr Tyr Gly Glu Met Ala Asp Cys Cys Ala Lys Gln Glu Pro
            275                 280                 285

Glu Arg Asn Glu Cys Phe Leu Gln His Lys Asp Asp Asn Pro Asn Leu
            290                 295                 300

Pro Arg Leu Val Arg Pro Glu Val Asp Val Met Cys Thr Ala Phe His
305                 310                 315                 320

Asp Asn Glu Glu Thr Phe Leu Lys Lys Tyr Leu Tyr Glu Ile Ala Arg
                325                 330                 335

Arg His Pro Tyr Phe Tyr Ala Pro Glu Leu Leu Phe Phe Ala Lys Arg
            340                 345                 350

Tyr Lys Ala Ala Phe Thr Glu Cys Cys Gln Ala Ala Asp Lys Ala Ala
            355                 360                 365

Cys Leu Leu Pro Lys Leu Asp Glu Leu Arg Asp Glu Gly Lys Ala Ser
        370                 375                 380

Ser Ala Lys Gln Arg Leu Lys Cys Ala Ser Leu Gln Lys Phe Gly Glu
385                 390                 395                 400

Arg Ala Phe Lys Ala Trp Ala Val Ala Arg Leu Ser Gln Arg Phe Pro
                405                 410                 415

Lys Ala Glu Phe Ala Glu Val Ser Lys Leu Val Thr Asp Leu Thr Lys
            420                 425                 430

Val His Thr Glu Cys Cys His Gly Asp Leu Leu Glu Cys Ala Asp Asp
            435                 440                 445
```

```
Arg Ala Asp Leu Ala Lys Tyr Ile Cys Glu Asn Gln Asp Ser Ile Ser
            450                 455                 460

Ser Lys Leu Lys Glu Cys Cys Glu Lys Pro Leu Leu Glu Lys Ser His
465                 470                 475                 480

Cys Ile Ala Glu Val Glu Asn Asp Glu Met Pro Ala Asp Leu Pro Ser
                    485                 490                 495

Leu Ala Ala Asp Phe Val Glu Ser Lys Asp Val Cys Lys Asn Tyr Ala
                500                 505                 510

Glu Ala Lys Asp Val Phe Leu Gly Met Phe Leu Tyr Glu Tyr Ala Arg
            515                 520                 525

Arg His Pro Asp Tyr Ser Val Val Leu Leu Leu Arg Leu Ala Lys Thr
530                 535                 540

Tyr Glu Thr Thr Leu Glu Lys Cys Cys Ala Ala Ala Asp Pro His Glu
545                 550                 555                 560

Cys Tyr Ala Lys Val Phe Asp Glu Phe Lys Pro Leu Val Glu Glu Pro
                565                 570                 575

Gln Asn Leu Ile Lys Gln Asn Cys Glu Leu Phe Glu Gln Leu Gly Glu
                580                 585                 590

Tyr Lys Phe Gln Asn Ala Leu Leu Val Arg Tyr Thr Lys Lys Val Pro
            595                 600                 605

Gln Val Ser Thr Pro Thr Leu Val Glu Val Ser Arg Asn Leu Gly Lys
610                 615                 620

Val Gly Ser Lys Cys Cys Lys His Pro Glu Ala Lys Arg Met Pro Cys
625                 630                 635                 640

Ala Glu Asp Tyr Leu Ser Val Val Leu Asn Gln Leu Cys Val Leu His
                645                 650                 655

Glu Lys Thr Pro Val Ser Asp Arg Val Thr Lys Cys Cys Thr Glu Ser
                660                 665                 670

Leu Val Asn Arg Arg Pro Cys Phe Ser Ala Leu Glu Val Asp Glu Thr
            675                 680                 685

Tyr Val Pro Lys Glu Phe Asn Ala Glu Thr Phe Thr Phe His Ala Asp
690                 695                 700

Ile Cys Thr Leu Ser Glu Lys Glu Arg Gln Ile Lys Lys Gln Thr Ala
705                 710                 715                 720

Leu Val Glu Leu Val Lys His Lys Pro Lys Ala Thr Lys Glu Gln Leu
                725                 730                 735

Lys Ala Val Met Asp Asp Phe Ala Ala Phe Val Glu Lys Cys Cys Lys
                740                 745                 750

Ala Asp Asp Lys Glu Thr Cys Phe Ala Glu Glu Gly Lys Lys Leu Val
            755                 760                 765

Ala Ala Ser Gln Ala Ala Leu Gly Leu
770                 775

<210> SEQ ID NO 59
<211> LENGTH: 718
<212> TYPE: PRT
<213> ORGANISM: Homo sapiens

<400> SEQUENCE: 59

Cys Thr Cys Ser Pro Ser His Pro Gln Asp Ala Phe Cys Asn Ser Asp
1               5                   10                  15

Ile Val Ile Arg Ala Lys Val Val Gly Lys Lys Leu Val Lys Glu Gly
            20                  25                  30

Pro Phe Gly Thr Leu Val Tyr Thr Ile Lys Gln Met Lys Met Tyr Arg
        35                  40                  45
```

```
Gly Phe Thr Lys Met Pro His Val Gln Tyr Ile His Thr Glu Ala Ser
 50                  55                  60
Glu Ser Leu Cys Gly Leu Lys Leu Glu Val Asn Lys Tyr Gln Tyr Leu
 65                  70                  75                  80
Leu Thr Gly Arg Val Tyr Asp Gly Lys Met Tyr Thr Gly Leu Cys Asn
                 85                  90                  95
Phe Val Glu Arg Trp Asp Gln Leu Thr Leu Ser Gln Arg Lys Gly Leu
            100                 105                 110
Asn Tyr Arg Tyr His Leu Gly Cys Asn Gly Gly Gly Asp Ala His
            115                 120                 125
Lys Ser Glu Val Ala His Arg Phe Lys Asp Leu Gly Glu Glu Asn Phe
130                 135                 140
Lys Ala Leu Val Leu Ile Ala Phe Ala Gln Tyr Leu Gln Gln Cys Pro
145                 150                 155                 160
Phe Glu Asp His Val Lys Leu Val Asn Glu Val Thr Glu Phe Ala Lys
                165                 170                 175
Thr Cys Val Ala Asp Glu Ser Ala Glu Asn Cys Asp Lys Ser Leu His
            180                 185                 190
Thr Leu Phe Gly Asp Lys Leu Cys Thr Val Ala Thr Leu Arg Glu Thr
            195                 200                 205
Tyr Gly Glu Met Ala Asp Cys Cys Ala Lys Gln Glu Pro Glu Arg Asn
210                 215                 220
Glu Cys Phe Leu Gln His Lys Asp Asp Asn Pro Asn Leu Pro Arg Leu
225                 230                 235                 240
Val Arg Pro Glu Val Asp Val Met Cys Thr Ala Phe His Asp Asn Glu
                245                 250                 255
Glu Thr Phe Leu Lys Lys Tyr Leu Tyr Glu Ile Ala Arg Arg His Pro
            260                 265                 270
Tyr Phe Tyr Ala Pro Glu Leu Leu Phe Phe Ala Lys Arg Tyr Lys Ala
            275                 280                 285
Ala Phe Thr Glu Cys Cys Gln Ala Ala Asp Lys Ala Ala Cys Leu Leu
290                 295                 300
Pro Lys Leu Asp Glu Leu Arg Asp Glu Gly Lys Ala Ser Ser Ala Lys
305                 310                 315                 320
Gln Arg Leu Lys Cys Ala Ser Leu Gln Lys Phe Gly Glu Arg Ala Phe
                325                 330                 335
Lys Ala Trp Ala Val Ala Arg Leu Ser Gln Arg Phe Pro Lys Ala Glu
            340                 345                 350
Phe Ala Glu Val Ser Lys Leu Val Thr Asp Leu Thr Lys Val His Thr
            355                 360                 365
Glu Cys Cys His Gly Asp Leu Leu Glu Cys Ala Asp Asp Arg Ala Asp
370                 375                 380
Leu Ala Lys Tyr Ile Cys Glu Asn Gln Asp Ser Ile Ser Ser Lys Leu
385                 390                 395                 400
Lys Glu Cys Cys Glu Lys Pro Leu Leu Glu Lys Ser His Cys Ile Ala
                405                 410                 415
Glu Val Glu Asn Asp Glu Met Pro Ala Asp Leu Pro Ser Leu Ala Ala
            420                 425                 430
Asp Phe Val Glu Ser Lys Asp Val Cys Lys Asn Tyr Ala Glu Ala Lys
            435                 440                 445
Asp Val Phe Leu Gly Met Phe Leu Tyr Glu Tyr Ala Arg Arg His Pro
450                 455                 460
```

Asp Tyr Ser Val Val Leu Leu Arg Leu Ala Lys Thr Tyr Glu Thr
465                 470                 475                 480

Thr Leu Glu Lys Cys Cys Ala Ala Ala Asp Pro His Glu Cys Tyr Ala
            485                 490                 495

Lys Val Phe Asp Glu Phe Lys Pro Leu Val Glu Glu Pro Gln Asn Leu
        500                 505                 510

Ile Lys Gln Asn Cys Glu Leu Phe Glu Gln Leu Gly Glu Tyr Lys Phe
    515                 520                 525

Gln Asn Ala Leu Leu Val Arg Tyr Thr Lys Lys Val Pro Gln Val Ser
530                 535                 540

Thr Pro Thr Leu Val Glu Val Ser Arg Asn Leu Gly Lys Val Gly Ser
545                 550                 555                 560

Lys Cys Cys Lys His Pro Glu Ala Lys Arg Met Pro Cys Ala Glu Asp
            565                 570                 575

Tyr Leu Ser Val Val Leu Asn Gln Leu Cys Val Leu His Glu Lys Thr
        580                 585                 590

Pro Val Ser Asp Arg Val Thr Lys Cys Cys Thr Glu Ser Leu Val Asn
    595                 600                 605

Arg Arg Pro Cys Phe Ser Ala Leu Glu Val Asp Glu Thr Tyr Val Pro
610                 615                 620

Lys Glu Phe Asn Ala Glu Thr Phe Thr Phe His Ala Asp Ile Cys Thr
625                 630                 635                 640

Leu Ser Glu Lys Glu Arg Gln Ile Lys Lys Gln Thr Ala Leu Val Glu
            645                 650                 655

Leu Val Lys His Lys Pro Lys Ala Thr Lys Glu Gln Leu Lys Ala Val
        660                 665                 670

Met Asp Asp Phe Ala Ala Phe Val Glu Lys Cys Cys Lys Ala Asp Asp
    675                 680                 685

Lys Glu Thr Cys Phe Ala Glu Glu Gly Lys Lys Leu Val Ala Ala Ser
690                 695                 700

Gln Ala Ala Leu Gly Leu Val Asp His His His His His
705                 710                 715

<210> SEQ ID NO 60
<211> LENGTH: 718
<212> TYPE: PRT
<213> ORGANISM: Homo sapiens

<400> SEQUENCE: 60

Cys Thr Cys Ser Pro Ser His Pro Gln Asp Ala Phe Cys Asn Ser Asp
1               5                   10                  15

Ile Val Ile Arg Ala Ser Val Val Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Lys Leu Glu Val Asn Lys Tyr Gln Tyr Leu
65                  70                  75                  80

Leu Thr Gly Arg Val Tyr Asp Gly Lys Met Tyr Thr Gly Leu Cys Asn
            85                  90                  95

Phe Val Glu Arg Trp Asp Gln Leu Thr Leu Ser Gln Arg Lys Gly Leu
        100                 105                 110

Asn Tyr Arg Tyr His Leu Gly Cys Asn Gly Gly Gly Asp Ala His
    115                 120                 125

```
Lys Ser Glu Val Ala His Arg Phe Lys Asp Leu Gly Glu Glu Asn Phe
130                 135                 140

Lys Ala Leu Val Leu Ile Ala Phe Ala Gln Tyr Leu Gln Gln Cys Pro
145                 150                 155                 160

Phe Glu Asp His Val Lys Leu Val Asn Glu Val Thr Glu Phe Ala Lys
                165                 170                 175

Thr Cys Val Ala Asp Glu Ser Ala Glu Asn Cys Asp Lys Ser Leu His
                180                 185                 190

Thr Leu Phe Gly Asp Lys Leu Cys Thr Val Ala Thr Leu Arg Glu Thr
            195                 200                 205

Tyr Gly Glu Met Ala Asp Cys Cys Ala Lys Gln Glu Pro Glu Arg Asn
210                 215                 220

Glu Cys Phe Leu Gln His Lys Asp Asp Asn Pro Asn Leu Pro Arg Leu
225                 230                 235                 240

Val Arg Pro Glu Val Asp Val Met Cys Thr Ala Phe His Asp Asn Glu
                245                 250                 255

Glu Thr Phe Leu Lys Lys Tyr Leu Tyr Glu Ile Ala Arg Arg His Pro
                260                 265                 270

Tyr Phe Tyr Ala Pro Glu Leu Leu Phe Phe Ala Lys Arg Tyr Lys Ala
            275                 280                 285

Ala Phe Thr Glu Cys Cys Gln Ala Ala Asp Lys Ala Ala Cys Leu Leu
290                 295                 300

Pro Lys Leu Asp Glu Leu Arg Asp Glu Gly Lys Ala Ser Ser Ala Lys
305                 310                 315                 320

Gln Arg Leu Lys Cys Ala Ser Leu Gln Lys Phe Gly Glu Arg Ala Phe
                325                 330                 335

Lys Ala Trp Ala Val Ala Arg Leu Ser Gln Arg Phe Pro Lys Ala Glu
                340                 345                 350

Phe Ala Glu Val Ser Lys Leu Val Thr Asp Leu Thr Lys Val His Thr
            355                 360                 365

Glu Cys Cys His Gly Asp Leu Leu Glu Cys Ala Asp Asp Arg Ala Asp
370                 375                 380

Leu Ala Lys Tyr Ile Cys Glu Asn Gln Asp Ser Ile Ser Ser Lys Leu
385                 390                 395                 400

Lys Glu Cys Cys Glu Lys Pro Leu Leu Glu Lys Ser His Cys Ile Ala
                405                 410                 415

Glu Val Glu Asn Asp Glu Met Pro Ala Asp Leu Pro Ser Leu Ala Ala
                420                 425                 430

Asp Phe Val Glu Ser Lys Asp Val Cys Lys Asn Tyr Ala Glu Ala Lys
            435                 440                 445

Asp Val Phe Leu Gly Met Phe Leu Tyr Glu Tyr Ala Arg Arg His Pro
450                 455                 460

Asp Tyr Ser Val Val Leu Leu Leu Arg Leu Ala Lys Thr Tyr Glu Thr
465                 470                 475                 480

Thr Leu Glu Lys Cys Cys Ala Ala Ala Asp Pro His Glu Cys Tyr Ala
                485                 490                 495

Lys Val Phe Asp Glu Phe Lys Pro Leu Val Glu Glu Pro Gln Asn Leu
                500                 505                 510

Ile Lys Gln Asn Cys Glu Leu Phe Glu Gln Leu Gly Glu Tyr Lys Phe
            515                 520                 525

Gln Asn Ala Leu Leu Val Arg Tyr Thr Lys Lys Val Pro Gln Val Ser
530                 535                 540
```

-continued

Thr Pro Thr Leu Val Glu Val Ser Arg Asn Leu Gly Lys Val Gly Ser
545                 550                 555                 560

Lys Cys Cys Lys His Pro Glu Ala Lys Arg Met Pro Cys Ala Glu Asp
                565                 570                 575

Tyr Leu Ser Val Val Leu Asn Gln Leu Cys Val Leu His Glu Lys Thr
            580                 585                 590

Pro Val Ser Asp Arg Val Thr Lys Cys Cys Thr Glu Ser Leu Val Asn
        595                 600                 605

Arg Arg Pro Cys Phe Ser Ala Leu Glu Val Asp Glu Thr Tyr Val Pro
610                 615                 620

Lys Glu Phe Asn Ala Glu Thr Phe Thr Phe His Ala Asp Ile Cys Thr
625                 630                 635                 640

Leu Ser Glu Lys Glu Arg Gln Ile Lys Lys Gln Thr Ala Leu Val Glu
                645                 650                 655

Leu Val Lys His Lys Pro Lys Ala Thr Lys Glu Gln Leu Lys Ala Val
            660                 665                 670

Met Asp Asp Phe Ala Ala Phe Val Glu Lys Cys Cys Lys Ala Asp Asp
        675                 680                 685

Lys Glu Thr Cys Phe Ala Glu Glu Gly Lys Lys Leu Val Ala Ala Ser
690                 695                 700

Gln Ala Ala Leu Gly Leu Val Asp His His His His His His
705                 710                 715

<210> SEQ ID NO 61
<211> LENGTH: 2391
<212> TYPE: DNA
<213> ORGANISM: Homo sapiens

<400> SEQUENCE: 61

```
atgacccctt ggctcgggct catcgtgctc ctgggcagct ggagcctggg ggactggggc      60
gccgaggcgt gcacatgctc gcccagccac cccaggacg ccttctgcaa ctccgacatc     120
gtgatccggg ccaaggtggt ggggaagaag ctggtaaagg aggggcccttcggcacgctg     180 gtctacacca tcaagcagat gaagatgtac cgaggcttca ccaagatgcc aatgtgacg     240 tacatccaca cggaagcttc cgagagtctc tgtggcctta tctgacggt caacaagtac     300 cagtacctgc tgacaggtcg cgtctataat ggcacgatgt acacggggct gtgcaacttc     360
gtggagaggt gggaccagct caccctctcc cagcgcaagg ggctgaacta tcgtatcac     420 ctgggttgta actgcaagat caagtcctgc tactacctgc cttgctttgt gacttccaag     480
aacgagtgtc tctggaccga catgctctcc aatttcggtt accctggcta ccagtccaaa     540
cactacgcct gcatccggca gaagggcggc tactgcagct ggtaccgagg atgggccccc     600
ccggataaaa gcatcatcaa tgccacagac ccgatgcac acaagagtga ggttgctcat     660
cgatttaaag atttgggaga gaaaatttc aaagccttgg tgttgattgc ctttgctcag     720
tatcttcagc agtgtccatt tgaagatcat gtaaaattag tgaatgaagt aactgaattt     780
gcaaaaacat gtgttgctga tgagtcagct gaaaattgtg acaaatcact tcataccctt     840
tttggagaca aattatgcac agttgcaact cttcgtgaaa cctatggtga aatggctgac     900
tgctgtgcaa acaagaacc tgagagaaat gaatgcttct gcaacacaa agatgacaac     960 ccaaacctcc cccgattggt gagaccagag gttgatgtga tgtgcactgc ttttcatgac    1020
aatgaagaga catttttgaa aaatacttta tatgaaattg ccagaagaca tccttacttt    1080
tatgccccgg aactcctttt ctttgctaaa aggtataaag ctgcttttac agaatgttgc    1140
```

-continued

| | |
|---|---|
| caagctgctg ataaagctgc ctgcctgttg ccaaagctcg atgaacttcg ggatgaaggg | 1200 |
| aaggcttcgt ctgccaaaca gagactcaag tgtgccagtc tccaaaaatt tggagaaaga | 1260 |
| gctttcaaag catgggcagt agctcgcctg agccagagat ttcccaaagc tgagtttgca | 1320 |
| gaagtttcca agttagtgac agatcttacc aaagtccaca cggaatgctg ccatggagat | 1380 |
| ctgcttgaat gtgctgatga cagggcggac cttgccaagt atatctgtga aaatcaagat | 1440 |
| tcgatctcca gtaaactgaa ggaatgctgt gaaaaacctc tgttggaaaa atcccactgc | 1500 |
| attgccgaag tggaaaatga tgagatgcct gctgacttgc cttcattagc tgctgatttt | 1560 |
| gttgaaagta aggatgtttg caaaaactat gctgaggcaa aggatgtctt cctgggcatg | 1620 |
| tttttgtatg aatatgcaag aaggcatcct gattactctg tcgtgctgct gctgagactt | 1680 |
| gccaagacat atgaaaccac tctagagaag tgctgtgccg ctgcagatcc tcatgaatgc | 1740 |
| tatgccaaag tgttcgatga atttaaacct cttgtggaag agcctcagaa tttaatcaaa | 1800 |
| caaaattgtg agcttttttga gcagcttgga gagtacaaat tccagaatgc gctattagtt | 1860 |
| cgttacacca agaaagtacc ccaactgtca actccaactc ttatcgaggt ctcaagaaac | 1920 |
| ctaggaaaag tgggcagcaa atgttgtaaa catcctgaag caaaaagaat gccctgtgca | 1980 |
| gaagactatc tatccgtggt cctgaaccag ttatgtgtgt tgcatgagaa aacgccagta | 2040 |
| agtgacagag tcaccaaaatg ctgcacagaa tccttggtga acaggcgacc atgcttttca | 2100 |
| gctctggaag tcgatgaaac atacgttccc aaagagttta cagctaacac attcaccttc | 2160 |
| catgcagata tatgcacact ttctgagaag gagagacaaa tcaagaaaca aactgtgctt | 2220 |
| gttgagctcg tgaaacacaa gcccaaggca acaaaagagc aactgaaagc tgccatggat | 2280 |
| gatttcgcag cttttgtaga gaagtgctgc aaggctgacg ataaggagac ctgctttagc | 2340 |
| gaggagggta aaaaacttgt tgcggccagt caggccgcct taggcttatg a | 2391 |

<210> SEQ ID NO 62
<211> LENGTH: 1326
<212> TYPE: DNA
<213> ORGANISM: Homo sapiens

<400> SEQUENCE: 62

| | |
|---|---|
| atgacccctt ggctcgggct catcgtgctc ctgggcagct ggagcctggg ggactggggc | 60 |
| gccgaggcgt gcacatgctc gcccagccac cccagggacg ccttctgcaa ctccgacatc | 120 |
| gtgatccggg ccagtgtggt ggggaagaag ctggtaaagg aggggcccaa tggcacgctg | 180 |
| gtctacacca tcaagcagat gaagatgtac cgaggcttca ccaagatgcc ccatgtgcag | 240 |
| tacatcccata cggaagcttc cgagagtctc tgtggcctta agctggaggt caacaagtac | 300 |
| cagtacctgc tgacaggtcg cgtctatgat ggcaagatgt acacggggct gtgcaacttc | 360 |
| gtggagaggt gggaccagct caccctctcc cagcgcaagg ggctgaacta tcggtatcac | 420 |
| ctgggttgta actgcaagat caagtcctgc tactacctgc cttgctttgt gacttccaag | 480 |
| aacgagtgtc tctggaccga catgctctcc aatttcggtt accctggcta ccagtccaaa | 540 |
| cactacgcct gcatccggca gaagggcggc tactgcagct ggtaccgagg atgggccccc | 600 |
| ccggataaaa gcatcatcaa tgccacagac cccgtggagg tgagacaa actcacaca | 660 |
| tgtccccgt gcccagcacc tgaactcctg ggggaccgt cagtcttcct cttcccccca | 720 |
| aaacccaagg acacccctcat gatctcccgg acccctgagg tcacatgcgt ggtggtggac | 780 |
| gtgagccacg aagaccctga ggtcaagttc aactggtacg tggacggcgt ggaggtgcat | 840 |
| aatgccaaga caaagccgcg agaggagcag tacaacagca cgtaccgtgt ggtcagcgtc | 900 |

```
ctcaccgtcc tgcaccagga ctggctgaat ggcaaggagt acaagtgcaa ggtctccaac    960
aaagccctcc cagcccccat cgagaaaacc atctccaaag ccaaagggca gccccgagaa   1020
ccacaggtgt acaccctgcc cccatcccgg aaggagatga ccaagaacca ggtcagcctg   1080
acctgcctgg tcaaaggctt ctatcccagc gacatcgccg tggagtggga gagcaatggg   1140
cagccggaga caactacaa gaccacgcct cccgtgctga gtccgacgg ctccttcttc   1200 ctctatagca agctcaccgt ggacaagagc aggtggcagc aggggaacgt cttctcatgc   1260
tccgtgatgc atgaggctct gcacaaccac tacacgcaga agagcctctc cctgtctccg   1320
ggtaaa                                                             1326

<210> SEQ ID NO 63
<211> LENGTH: 741
<212> TYPE: DNA
<213> ORGANISM: Homo sapiens

<400> SEQUENCE: 63
atggggtcaa ccgccatcct cgccctcctc ctggctgttc tccaaggagt ctgcgctgac     60
aaaactcaca catgtccacc gtgcccagca cctgaactcc tggggggacc gtcagtcttc    120
ctcttccccc caaaacccaa ggacaccctc atgatctccc ggacccctga ggtcacatgc    180
gtggtggtgg acgtgagcca cgaagaccct gaggtcaagt tcaactggta cgtggacggc    240
gtggaggtgc ataatgccaa gacaaagccg cgggaggagc agtacaacag cacgtaccgt    300
gtggtcagcg tcctcaccgt cctgcaccag gactggctga atggcaagga gtacaagtgc    360
aaggtctcca acaaagccct cccagccccc atcgagaaaa ccatctccaa agccaaaggg    420
cagccccgag aaccacaggt gtacaccctg cccccatccc gggaggagat gaccaagaac    480
caggtcagcc tgacctgcct ggtcaaaggc ttctatccca gcgacatcgc cgtggagtgg    540
gagagcaatg ggcagccgga gaacaactac gacaccacgc ctcccgtgct ggactccgac    600
ggctccttct tcctctatag cgacctcacc gtggacaaga gcaggtggca gcaggggaac    660
gtcttctcat gctccgtgat gcatgaggct ctgcacaacc actacacgca gaagagcctc    720
tccctgtctc cgggtaaatg a                                              741

<210> SEQ ID NO 64
<211> LENGTH: 1989
<212> TYPE: DNA
<213> ORGANISM: Homo sapiens

<400> SEQUENCE: 64
atgacccctt ggctcgggct catcgtgctc ctgggcagct ggagcctggg ggactggggc     60
gccgaggcgt gcacatgctc gcccagccac ccccaggacg ccttctgcaa ctccgacatc    120
gtgatccggg ccaaggtggt ggggaagaat ctgacaaagg aggggcccct cggcacgctg    180
gtctacacca tcaagcagat gaagatgtac cgaggcttca ccaagatgcc ccatgtgcag    240
tacatccaca cggaagcttc cgagagtctc tgtggcctta atctgacggt caacaagtac    300
cagtacctgc tgacaggtcg cgtctatgat ggcaagatgt acacgggggct gtgcaacttc    360 gtggagaggt gggaccagct caccctctcc cagcgcaagg ggctgaacta tcgtatcac    420 ctgggttgta actgcaagat caagtcctgc tactacctgc cttgctttgt gacttccaag    480
aacgagtgtc tctggaccga catgctctcc aatttcactt accctggcta ccagtccaaa    540
cactacgcct gcatccggca aagggcggc tactgcagct ggtaccgagg atgggccct    600
```

```
ccggataaaa gcatcatcaa tgccacagac ccccaggtgc agctgcagga gtcgggccca      660
ggactggtga agccttcaca gaccctgtcc ctcacctgca ctgtctctgg tggctccatc      720
agcagtggtg attacttctg gagctggatc cgccagctcc cagggaaggg cctggagtgg      780
attgggcaca tccataacag tgggaccacc tactacaatc cgtccctcaa gagtcgagtt      840
accatatcag tagacacgtc taagaagcag ttctccctga ggctgagttc tgtgactgcc      900
gcggacacgg ccgtatatta ctgtgcgaga gatcgagggg gtgactacgc ttatggtatg      960
gacgtctggg gccaagggac cacggtcacc gtctcctcag cctccaccaa gggcccatcc     1020 gtcttcccc tggcaccctc ctccaagagc acctctgggg gcacagcggc cctgggctgc      1080
ctggtcaagg actacttccc cgaaccggtg acggtgtcgt ggaactcagg cgccctgacc     1140
agcggcgtgc acaccttccc ggctgtccta cagtcctcag gactctactc cctcagcagc     1200
gtggtgaccg tgccctccag cagcttgggc acccagacct acatctgcaa cgtgaatcac     1260
aagcccagca acaccaaggt ggacaagaga gttgagccca aatcttgtga caaaactcac     1320
acatgcccac cgtgcccagc acctgaactc ctggggggac cgtcagtctt cctcttcccc     1380
ccaaaaccca aggacaccct catgatctcc cggacccctg aggtcacatg cgtggtggtg     1440
gacgtgagcc acgaagaccc tgaggtcaag ttcaactggt acgtggacgg cgtggaggtg     1500
cataatgcca agacaaagcc gcgggaggag cagtacaaca gcacgtaccg tgtggtcagc     1560
gtcctcaccg tcctgcacca ggactggctg aatggcaagg agtacaagtg caaggtctcc     1620
aacaaagccc tcccagcccc catcgagaaa accatctcca aagccaaagg gcagccccga     1680
gaaccacagg tgtacaccct gcccccatcc cgggaggaga tgaccaagaa ccaggtcagc     1740
ctgacctgcc tggtcaaagg cttctatccc agcgacatcg ccgtggagtg ggagagcaat     1800
gggcagccgg agaacaacta caagaccacg cctcccgtgc tggactccga cggctccttc     1860
ttcctctata gcaagctcac cgtggacaag agcaggtggc agcaggggaa cgtcttctca     1920
tgctccgtga tgcatgaggc tctgcacaac cactacacgc agaagagcct ctccctgtct     1980
ccgggtaaa                                                            1989
```

<210> SEQ ID NO 65
<211> LENGTH: 1278
<212> TYPE: DNA
<213> ORGANISM: Homo sapiens

<400> SEQUENCE: 65

```
atgacccctt ggctcgggct catcgtgctc ctgggcagct ggagcctggg ggactggggc       60
gccgaggcgt gcacatgctc gcccagccac ccccaggacg ccttctgcaa ctccgacatc      120
gtgatccggg ccaaggtggt ggggaagaat ctgacaaagg aggggccctt cggcacgctg      180
gtctacacca tcaagcagat gaagatgtac cgaggcttca ccaagatgcc ccatgtgcag      240
tacatccaca cggaagcttc cgagagtctc tgtggcctta atctgacggt caacaagtac      300
cagtacctgc tgacaggtcg cgtctatgat ggcaagatgt acacgggct gtgcaacttc      360 gtggagaggt gggaccagct caccctctcc cagcgcaagg ggctgaacta tcgtatcac      420 ctgggttgta actgcaagat caagtcctgc tactacctgc cttgctttgt gacttccaag      480
aacgagtgtc tctggaccga catgctctcc aatttcactt accctggcta ccagtccaaa      540
cactacgcct gcatccggca gaagggcggc tactgcagct ggtaccgagg atgggcccct      600
ccggataaaa gcatcatcaa tgccacagac cccgaaattg tgttgacgca gtctccaggc      660
accctgtctt tgtctccagg ggaaagagcc accctctcct gcagggccag tcagggtatt      720
```

```
agtagaagcg aattagcctg gtaccagcag aaacctggcc aggctcccag cctcctcatc      780
tatggtgcat ccagcagggc cactggcatc ccagacaggt tcagtggcag tgggtctggg      840
acagacttca ctctcaccat cagcagactg gagcctgaag attttgcagt gtattactgt      900
caacaatttg gtagttcacc gtggacgttc ggccaaggga ccaaggtgga aatcaaacga      960
actgtggctg caccatctgt cttcatcttc ccgccatctg atgagcagtt gaaatctgga     1020
actgctagcg ttgtgtgcct gctgaataac ttctatccca gagaggccaa agtacagtgg     1080
aaggtggata acgccctcca atcgggtaac tcccaggaga gtgtcacaga gcaggacagc     1140
aaggacagca cctacagcct cagcagcacc ctgacgctga gcaaagcaga ctacgagaaa     1200
cacaaagtct acgcctgcga agtcacccat cagggcctga gctcgcccgt cacaaagagc     1260
ttcaacaggg gagagtgt                                                   1278

<210> SEQ ID NO 66
<211> LENGTH: 1284
<212> TYPE: DNA
<213> ORGANISM: Homo sapiens

<400> SEQUENCE: 66
atgacccctt ggctcgggct catcgtgctc ctgggcagct ggagcctggg ggactggggc       60
gccgaggcgt gcacatgctc gcccagccac ccccaggacg ccttctgcaa ctccgacatc      120
gtgatccggg ccaaggtggt ggggaagaag ctggtaaagg aggggcccct cggcacgctg      180
gtctacacca tcaagcagat gaagatgtac cgaggcttca ccaagatgcc caatgtgacg      240
tacatccaca cggaagcttc cgagagtctc tgtggcctta atctgacggt caacaagtac      300
cagtacctgc tgacaggtcg cgtctataat ggcacgatgt acacggggct gtgcaacttc      360
gtggagaggt gggaccagct caccctctcc cagcgcaagg ggctgaacta tcgtatcac      420 ctgggttgta actgcaagat caagtcctgc tactacctgc cttgctttgt gacttccaag      480
aacgagtgtc tctggaccga catgctctcc aatttcggtt accctggcta ccagtccaaa      540
cactacgcct gcatccggca gaagggcggc tactgcagct ggtaccgagg atgggccccc      600
ccggataaaa gcatcatcaa tgccacagac cccgcacctg aactcctggg gggaccgtca      660
gtcttcctct ccccccaaa acccaaggac accctcatga tctcccggac ccctgaggtc      720
acatgcgtgg tggtggacgt gagccacgaa gaccctgagg tcaagttcaa ctggtacgtg      780
gacggcgtgg aggtgcataa tgccaagaca aagccgcggg aggagcagta caacagcacg      840
taccgtgtgg tcagcgtcct caccgtcctg caccaggact ggctgaatgg caaggagtac      900
aagtgcaagg tctccaacaa agccctccca gcccccatcg agaaaaccat ctccaaagcc      960
aaagggcagc cccgagaacc acaggtgacc accctgcccc catcccggga ggagatgaac     1020
aagacccagg tcagcctgac ctgcctggtc aaaggcttct atcccagcga catcgccgtg     1080
gagtgggaga gcaatgggca gccggagaac aactacgaca ccacgcctcc cgtgctggac     1140
tccgacggct ccttcttcct ctatagcgac ctcaccgtgg acaagagcag gtggcagcag     1200
gggaacgtct tctcatgctc cgtgatgcat gaggctctgc acaaccacta cacgcagaag     1260
agcctctccc tgtctccggg taag                                           1284

<210> SEQ ID NO 67
<211> LENGTH: 2409
<212> TYPE: DNA
<213> ORGANISM: Homo sapiens
```

```
<400> SEQUENCE: 67
atgacccctt ggctcgggct catcgtgctc ctgggcagct ggagcctggg ggactggggc      60
gccgaggcgt gcacatgctc gcccagccac ccccaggacg ccttctgcaa ctccgacatc     120
gtgatccggg ccaaggtggt ggggaagaag ctggtaaagg aggggcccct cggcacgctg     180
gtctacacca tcaagcagat gaagatgtac cgaggcttca ccaagatgcc ccatgtgcag     240
tacatccata cggaagcttc cgagagtctc tgtggcctta agctggaggt caacaagtac     300
cagtacctgc tgacaggtcg cgtctatgat ggcaagatgt acacggggct gtgcaacttc     360
gtggagaggt gggaccagct caccctctcc cagcgcaagg ggctgaacta tcggtatcac     420
ctgggttgta actgcaagat caagtcctgc tactacctgc cttgctttgt gacttccaag     480
aacgagtgtc tctggaccga catgctctcc aatttcggtt accctggcta ccagtccaaa     540
cactacgcct gcatccggca aagggcggc tactgcagct ggtaccgagg atgggccccc     600
ccggataaaa gcatcatcaa tgccacagac cccgatgcac acaagagtga ggttgctcat     660
cggtttaaag atttgggaga agaaaatttc aaagccttgg tgttgattgc ctttgctcag     720
tatcttcagc agtgtccatt tgaagatcat gtaaaattag tgaatgaagt aactgaattt     780
gcaaaaacat gtgttgctga tgagtcagct gaaaattgtg acaaatcact tcataccctt     840
tttggagaca aattatgcac agttgcaact cttcgtgaaa cctatggtga atggctgac     900 tgctgtgcaa acaagaacc tgagagaaat gaatgcttct gcaacacaa agatgacaac     960 ccaaacctcc cccgattggt gagaccagag gttgatgtga tgtgcactgc ttttcatgac    1020
aatgaagaga cattttgaa aaaatactta tatgaaattg ccagaagaca tccttacttt    1080
tatgccccgg aactccttt ctttgctaaa aggtataaag ctgcttttac agaatgttgc    1140
caagctgctg ataaagctgc ctgcctgttg ccaaagctcg atgaacttcg ggatgaaggg    1200
aaggcttcgt ctgccaaaca gagactcaag tgtgccagtc tccaaaaatt tggagaaaga    1260
gctttcaaag catgggcagt agctcgcctg agccagagat ttcccaaagc tgagtttgca    1320 gaagttttcca gttagtgac agatcttacc aaagtccaca cggaatgctg ccatggagat    1380
ctgcttgaat gtgctgatga cagggcggac cttgccaagt atatctgtga aaatcaagat    1440
tcgatctcca gtaaactgaa ggaatgctgt gaaaaacctc tgttggaaaa atcccactgc    1500
attgccgaag tggaaaatga tgagatgcct gctgacttgc cttcattagc tgctgatttt    1560
gttgaaagta aggatgtttg caaaaactat gctgaggcaa aggatgtctt cctgggcatg    1620
tttttgtatg aatatgcaag aaggcatcct gattactctg tcgtgctgct gctgagactt    1680
gccaagacat atgaaaccac tctagagaag tgctgtgccg ctgcagatcc tcatgaatgc    1740
tatgccaaag tgttcgatga atttaaacct cttgtggaag agcctcagaa tttaatcaaa    1800
caaaattgtg agcttttga gcagcttgga gagtacaaat tccagaatgc gctattagtt    1860
cgttacacca gaaagtacc ccaagtgtca actccaactc ttgtagaggt ctcaagaaac    1920
ctaggaaaag tgggcagcaa atgttgtaaa catcctgaag caaaagaat gccctgtgca    1980 gaagactatc tatccgtggt cctgaaccag ttatgtgtgt tgcatgagaa aacgccagta    2040
agtgacagag tcaccaaatg ctgcacagaa tccttggtga acaggcgacc atgcttttca    2100
gctctggaag tcgatgaaac atacgttccc aaagagttta atgctgaaac attcaccttc    2160
catgcagata tatgcacact ttctgagaag gagagacaaa tcaagaaaca aactgcactt    2220
gttgagctcg tgaaacacaa gcccaaggca acaaaagagc aactgaaagc tgttatggat    2280
gatttcgcag cttttgtaga gaagtgctgc aaggctgacg ataaggagac ctgcttgcc    2340
```

| | |
|---|---|
| gaggagggta aaaaacttgt tgctgcaagt caagctgcct taggcttaca tcatcatcat | 2400 |
| catcattga | 2409 |

<210> SEQ ID NO 68
<211> LENGTH: 2400
<212> TYPE: DNA
<213> ORGANISM: Homo sapiens

<400> SEQUENCE: 68

| | |
|---|---|
| atgacccctt ggctcgggct catcgtgctc ctgggcagct ggagcctggg ggactggggc | 60 |
| gccgaggcgt gcacatgctc gcccagccac ccccaggacg ccttctgcaa ctccgacatc | 120 |
| gtgatccggg ccagtgtggt ggggaagaag ctggtaaagg aggggcccaa tggcacgctg | 180 |
| gtctacacca tcaagcagat gaagatgtac cgaggcttca ccaagatgcc ccatgtgcag | 240 |
| tacatcccta cggaagcttc cgagagtctc tgtggcctta agctggaggt caacaagtac | 300 |
| cagtacctgc tgacaggtcg cgtctatgat ggcaagatgt acacggggct gtgcaacttc | 360 |
| gtggagaggt gggaccagct caccctctcc cagcgcaagg ggctgaacta tcggtatcac | 420 |
| ctgggttgta actgcaagat caagtcctgc tactacctgc cttgctttgt gacttccaag | 480 |
| aacgagtgtc tctggaccga catgctctcc aatttcggtt accctggcta ccagtccaaa | 540 |
| cactacgcct gcatccggca aagggcggc tactgcagct ggtaccgagg atgggccccc | 600 |
| ccggataaaa gcatcatcaa tgccacagac cccggtggag gtggagatgc acacaagagt | 660 |
| gaggttgctc atcggtttaa agatttggga gaagaaaatt tcaaagcctt ggtgttgatt | 720 |
| gcctttgctc agtatcttca gcagtgtcca tttgaagatc atgtaaaatt agtgaatgaa | 780 |
| gtaactgaat ttgcaaaaac atgtgttgct gatgagtcag ctgaaaattg tgacaaatca | 840 |
| cttcataccc tttttggaga caaattatgc acagttgcaa ctcttcgtga aacctatggt | 900 |
| gaaatggctg actgctgtgc aaaacaagaa cctgagagaa atgaatgctt cttgcaacac | 960 |
| aaagatgaca acccaaacct ccccgattg gtgagaccag aggttgatgt gatgtgcact | 1020 |
| gcttttcatg acaatgaaga gacattttg aaaaaatact tatatgaaat tgccagaaga | 1080 |
| catccttact tttatgcccc ggaactcctt ttctttgcta aaaggtataa agctgctttt | 1140 |
| acagaatgtt gccaagctgc tgataaagct gcctgcctgt tgccaaagct cgatgaactt | 1200 |
| cgggatgaag ggaaggcttc gtctgccaaa cagagactca agtgtgccag tctccaaaaa | 1260 |
| tttggagaaa gagctttcaa agcatgggca gtagctcgcc tgagccagag atttcccaaa | 1320 |
| gctgagtttg cagaagtttc caagttagtg acagatctta ccaaagtcca cacggaatgc | 1380 |
| tgccatggag atctgcttga atgtgctgat gacagggcgg accttgccaa gtatatctgt | 1440 |
| gaaaatcaag attcgatctc cagtaaactg aaggaatgct gtgaaaaacc tctgttggaa | 1500 |
| aaatcccact gcattgccga agtggaaaat gatgagatgc ctgctgactt gccttcatta | 1560 |
| gctgctgatt ttgttgaaag taaggatgtt tgcaaaaact atgctgaggc aaaggatgtc | 1620 |
| ttcctgggca tgtttttgta tgaatatgca agaaggcatc ctgattactc tgtcgtgctg | 1680 |
| ctgctgagac ttgccaagac atatgaaacc actctagaga agtgctgtgc cgctgcagat | 1740 |
| cctcatgaat gctatgccaa agtgttcgat gaatttaaac tcttgtgga agagcctcag | 1800 |
| aatttaatca acaaaattg tgagcttttt gagcagcttg gagagtacaa attccagaat | 1860 |
| gcgctattag ttcgttacac caagaaagta ccccaagtgt caactccaac tcttgtagag | 1920 |
| gtctcaagaa acctaggaaa agtgggcagc aaatgttgta aacatcctga agcaaaaaga | 1980 |

| | |
|---|---|
| atgccctgtg cagaagacta tctatccgtg gtcctgaacc agttatgtgt gttgcatgag | 2040 |
| aaaacgccag taagtgacag agtcaccaaa tgctgcacag aatccttggt gaacaggcga | 2100 |
| ccatgctttt cagctctgga agtcgatgaa acatacgttc ccaaagagtt taatgctgaa | 2160 |
| acattcacct tccatgcaga tatatgcaca ctttctgaga aggagagaca aatcaagaaa | 2220 |
| caaactgcac ttgttgagct cgtgaaacac aagcccaagg caacaaaaga gcaactgaaa | 2280 |
| gctgttatgg atgatttcgc agcttttgta gagaagtgct gcaaggctga cgataaggag | 2340 |
| acctgctttg ccgaggaggg taaaaaactt gttgctgcaa gtcaagctgc cttaggctta | 2400 |

<210> SEQ ID NO 69
<211> LENGTH: 2223
<212> TYPE: DNA
<213> ORGANISM: Homo sapiens

<400> SEQUENCE: 69

| | |
|---|---|
| atgacccctt ggctcgggct catcgtgctc ctgggcagct ggagcctggg ggactggggc | 60 |
| gccgaggcgt gcacatgctc gcccagccac ccccaggacg ccttctgcaa ctccgacatc | 120 |
| gtgatccggg ccaaggtggt ggggaagaag ctggtaaagg aggggcccct cggcacgctg | 180 |
| gtctacacca tcaagcagat gaagatgtac cgaggcttca ccaagatgcc ccatgtgcag | 240 |
| tacatccaca cggaagcttc cgagagtctc tgtggcctta agctggaggt caacaagtac | 300 |
| cagtacctgc tgacaggtcg cgtctatgat ggcaagatgt acacggggct gtgcaacttc | 360 |
| gtggagaggt gggaccagct caccctctcc cagcgcaagg ggctgaacta tcggtatcac | 420 |
| ctgggttgta acgtggagg tggagatgca cacaagagtg aggttgctca tcgatttaaa | 480 |
| gatttgggag aagaaaattt caaagccttg tgttgattg cctttgctca gtatcttcag | 540 |
| cagtgtccat ttgaagatca tgtaaaatta gtgaatgaag taactgaatt tgcaaaaaca | 600 |
| tgtgttgctg atgagtcagc tgaaaattgt gacaaatcac ttcataccct ttttggagac | 660 |
| aaattatgca gttgcaac tcttcgtgaa acctatggtg aaatggctga ctgctgtgca | 720 |
| aaacaagaac ctgagagaaa tgaatgcttc ttgcaacaca agatgacaaa cccaaacctc | 780 |
| ccccgattgg tgagaccaga ggttgatgtg atgtgcactg cttttcatga caatgaagag | 840 |
| acattttga aaaaatactt atatgaaatt gccagaagac atccttactt ttatgccccg | 900 |
| gaactccttt tctttgctaa aaggtataaa gctgctttta cagaatgttg ccaagctgct | 960 |
| gataaagctg cctgcctgtt gccaaagctc gatgaacttc gggatgaagg gaaggcttcg | 1020 |
| tctgccaaac agagactcaa gtgtgccagt ctccaaaaat ttggagaaag gcttttcaaa | 1080 |
| gcatgggcag tagctcgcct gagccagaga tttcccaaag ctgagtttgc agaagtttcc | 1140 |
| aagttagtga cagatcttac caaagtccac acggaatgct gccatggaga tctgcttgaa | 1200 |
| tgtgctgatg acagggcgga ccttgccaag tatatctgtg aaaatcaaga tcgatctcc | 1260 |
| agtaaactga aggaatgctg tgaaaaacct ctgttggaaa atcccactg cattgccgaa | 1320 |
| gtggaaaatg atgagatgcc tgctgacttg ccttcattag ctgctgattt tgttgaaagt | 1380 |
| aaggatgttt gcaaaaacta tgctgaggca aaggatgtct tcctgggcat gttttttgtat | 1440 |
| gaatatgcaa gaaggcatcc tgattactct gtcgtgctgc tgctgagact tgccaagaca | 1500 |
| tatgaaacca ctctagagaa gtgctgtgcc gctgcagatc ctcatgaatg ctatgccaaa | 1560 |
| gtgttcgatg aatttaaacc tcttgtggaa gagcctcaga atttaatcaa acaaaattgt | 1620 |
| gagctttttg agcagcttgg agagtacaaa ttccagaatg cgctattagt tcgttacacc | 1680 |
| aagaaagtac cccaagtgtc aactccaact cttgtagagg tctcaagaaa cctaggaaaa | 1740 |

| | |
|---|---|
| gtgggcagca aatgttgtaa acatcctgaa gcaaaaagaa tgccctgtgc agaagactat | 1800 |
| ctatccgtgg tcctgaacca gttatgtgtg ttgcatgaga aaacgccagt aagtgacaga | 1860 |
| gtcaccaaat gctgcacaga atccttggtg aacaggcgac catgcttttc agctctggaa | 1920 |
| gtcgatgaaa catacgttcc caaagagttt aatgctgaaa cattcacctt ccatgcagat | 1980 |
| atatgcacac tttctgagaa ggagagacaa atcaagaaac aaactgcact tgttgagctc | 2040 |
| gtgaaacaca gcccaaggc aacaaaagag caactgaaag ctgttatgga tgatttcgca | 2100 |
| gcttttgtag agaagtgctg caaggctgac gataaggaga cctgctttgc cgaggagggt | 2160 |
| aaaaaacttg ttgcggccag tcaggccgcc ttaggcttag tcgaccatca tcatcatcat | 2220 |
| cat | 2223 |

<210> SEQ ID NO 70
<211> LENGTH: 2223
<212> TYPE: DNA
<213> ORGANISM: Homo sapiens

<400> SEQUENCE: 70

| | |
|---|---|
| atgacccctt ggctcgggct catcgtgctc ctgggcagct ggagcctggg ggactggggc | 60 |
| gccgaggcgt gcacatgctc gcccagccac ccccaggacg ccttctgcaa ctccgacatc | 120 |
| gtgatccggg ccagtgtggt ggggaagaag ctggtaaagg aggggcccaa tggcacgctg | 180 |
| gtctacacca tcaagcagat gaagatgtac cgaggcttca ccaagatgcc ccatgtgcag | 240 |
| tacatccata cggaagcttc cgagagtctc tgtggcctta gctggaggt caacaagtac | 300 |
| cagtacctgc tgacaggtcg cgtctatgat ggcaagatgt acacggggct gtgcaacttc | 360 |
| gtggagaggt gggaccagct caccctctcc cagcgcaagg ggctgaacta tcggtatcac | 420 |
| ctgggttgta acggtggagg tggagatgca cacaagagtg aggttgctca tcgatttaaa | 480 |
| gatttgggag aagaaaattt caaagccttg gtgttgattg cctttgctca gtatcttcag | 540 |
| cagtgtccat ttgaagatca tgtaaaatta gtgaatgaag taactgaatt tgcaaaaaca | 600 |
| tgtgttgctg atgagtcagc tgaaaattgt gacaaatcac ttcataccct ttttggagac | 660 |
| aaattatgca cagttgcaac tcttcgtgaa acctatggtg aaatggctga ctgctgtgca | 720 |
| aaacaagaac ctgagagaaa tgaatgcttc ttgcaacaca aagatgacaa cccaaacctc | 780 |
| ccccgattgg tgagaccaga ggttgatgtg atgtgcactg cttttcatga caatgaagag | 840 |
| acatttttga aaaaatactt atatgaaatt gccagaagac atccttactt ttatgccccg | 900 |
| gaactccttt tctttgctaa aaggtataaa gctgctttta cagaatgttg ccaagctgct | 960 |
| gataaagctg cctgcctgtt gccaaagctc gatgaacttc gggatgaagg aaggcttcg | 1020 |
| tctgccaaac agagactcaa gtgtgccagt ctccaaaaat tggagaaag agctttcaaa | 1080 |
| gcatgggcag tagctcgcct gagccagaga tttcccaaag ctgagtttgc agaagtttcc | 1140 |
| aagttagtga cagatcttac caaagtccac acggaatgct gccatggaga tctgcttgaa | 1200 |
| tgtgctgatg acagggcgga ccttgccaag tatatctgtg aaaatcaaga ttcgatctcc | 1260 |
| agtaaactga aggaatgctg tgaaaaacct ctgttggaaa aatcccactg cattgccgaa | 1320 |
| gtggaaaatg atgagatgcc tgctgacttg ccttcattag ctgctgattt tgttgaaagt | 1380 |
| aaggatgttt gcaaaaacta tgctgaggca aggatgtct tcctgggcat gttttttgtat | 1440 |
| gaatatgcaa gaaggcatcc tgattactct gtcgtgctgc tgctgagact tgccaagaca | 1500 |
| tatgaaacca ctcagagaa gtgctgtgcc gctgcagatc ctcatgaatg ctatgccaaa | 1560 |

```
gtgttcgatg aatttaaacc tcttgtggaa gagcctcaga atttaatcaa acaaaattgt   1620 gagcttttg agcagcttgg agagtacaaa ttccagaatg cgctattagt tcgttacacc    1680
aagaaagtac cccaagtgtc aactccaact cttgtagagg tctcaagaaa cctaggaaaa   1740
gtgggcagca atgttgtaa acatcctgaa gcaaaaagaa tgccctgtgc agaagactat    1800
ctatccgtgg tcctgaacca gttatgtgtg ttgcatgaga aaacgccagt aagtgacaga   1860
gtcaccaaat gctgcacaga atccttggtg aacaggcgac catgcttttc agctctggaa   1920
gtcgatgaaa catacgttcc caaagagttt aatgctgaaa cattcacctt ccatgcagat   1980
atatgcacac tttctgagaa ggagagacaa atcaagaaac aaactgcact tgttgagctc   2040
gtgaaacaca agcccaaggc aacaaaagag caactgaaag ctgttatgga tgatttcgca   2100
gcttttgtag agaagtgctg caaggctgac gataaggaga cctgctttgc cgaggagggt   2160
aaaaaacttg ttgcggccag tcaggccgcc ttaggcttag tcgaccatca tcatcatcat   2220
cat                                                                2223
```

<210> SEQ ID NO 71
<211> LENGTH: 585
<212> TYPE: PRT
<213> ORGANISM: Homo sapiens

<400> SEQUENCE: 71

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255
```

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 72
<211> LENGTH: 227
<212> TYPE: PRT
<213> ORGANISM: Homo sapiens

<400> SEQUENCE: 72

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His

-continued

```
                35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
            100                 105                 110
Glu Lys Thr Ile Ser Lys Ala Lys Gly Gln Pro Arg Glu Pro Gln Val
            115                 120                 125
Tyr Thr Leu Pro Pro Ser Arg Glu Glu Met Thr Lys Asn Gln Val Ser
            130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
            210                 215                 220
Pro Gly Lys
225

<210> SEQ ID NO 73
<211> LENGTH: 217
<212> TYPE: PRT
<213> ORGANISM: Homo sapiens

<400> SEQUENCE: 73

Ala Pro Glu Leu Leu Gly Gly Pro Ser Val Phe Leu Phe Pro Pro Lys
  1               5                  10                  15
Pro Lys Asp Thr Leu Met Ile Ser Arg Thr Pro Glu Val Thr Cys Val
             20                  25                  30
Val Val Asp Val Ser His Glu Asp Pro Glu Val Lys Phe Asn Trp Tyr
             35                  40                  45
Val Asp Gly Val Glu Val His Asn Ala Lys Thr Lys Pro Arg Glu Glu
 50                  55                  60
Gln Tyr Asn Ser Thr Tyr Arg Val Val Ser Val Leu Thr Val Leu His
 65                  70                  75                  80
Gln Asp Trp Leu Asn Gly Lys Glu Tyr Lys Cys Lys Val Ser Asn Lys
                 85                  90                  95
Ala Leu Pro Ala Pro Ile Glu Lys Thr Ile Ser Lys Ala Lys Gly Gln
            100                 105                 110
Pro Arg Glu Pro Gln Val Thr Thr Leu Pro Pro Ser Arg Glu Glu Met
            115                 120                 125
Asn Lys Thr Gln Val Ser Leu Thr Cys Leu Val Lys Gly Phe Tyr Pro
            130                 135                 140
Ser Asp Ile Ala Val Glu Trp Glu Ser Asn Gly Gln Pro Glu Asn Asn
145                 150                 155                 160
Tyr Asp Thr Thr Pro Pro Val Leu Asp Ser Asp Gly Ser Phe Phe Leu
                165                 170                 175
```

```
Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 74
<211> LENGTH: 212
<212> TYPE: PRT
<213> ORGANISM: Homo sapiens

<400> SEQUENCE: 74

Gly Gly Pro Ser Val Phe Leu Phe Pro Pro Lys Pro Lys Asp Thr Leu
1               5                   10                  15

Met Ile Ser Arg Thr Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro Arg Glu Pro Gln
            100                 105                 110

Val Thr Thr Leu Pro Pro Ser Arg Glu Glu Met Asn Lys Thr Gln Val
        115                 120                 125

Ser Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Asp Thr Thr Pro
145                 150                 155                 160

Pro Val Leu Asp Ser Asp Gly Ser Phe Phe Leu Tyr Ser Asp Leu Thr
                165                 170                 175

Val Asp Lys Ser Arg Trp Gln Gln Gly Asn Val Phe Ser Cys Ser Val
            180                 185                 190

Met His Glu Ala Leu His Asn His Tyr Thr Gln Lys Ser Leu Ser Leu
        195                 200                 205

Ser Pro Gly Lys
    210

<210> SEQ ID NO 75
<211> LENGTH: 5
<212> TYPE: PRT
<213> ORGANISM: Artificial Sequence
<220> FEATURE:
<223> OTHER INFORMATION: Linker

<400> SEQUENCE: 75

Glu Pro Lys Ser Ser
1               5

<210> SEQ ID NO 76
<211> LENGTH: 415
<212> TYPE: PRT
<213> ORGANISM: Artificial Sequence
<220> FEATURE:
<223> OTHER INFORMATION: Synthetic Polypeptide
```

<400> SEQUENCE: 76

```
Cys Thr Cys Ser Pro Ser His Pro Gln Asp Ala Phe Cys Asn Ser Asp
1               5                   10                  15

Ile Val Ile Arg Ala Asn Val Thr Gly Lys Lys Leu Val Lys Glu Gly
                20                  25                  30

Pro Phe Gly Thr Leu Val Tyr Thr Ile Lys Gln Met Lys Met Tyr Arg
            35                  40                  45

Gly Phe Thr Lys Met Pro His Val Gln Tyr Ile His Thr Glu Ala Ser
        50                  55                  60

Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro Asp Lys Thr His
            180                 185                 190

Thr Cys Pro Pro Cys Pro Ala Pro Glu Leu Leu Gly Gly Pro Ser Val
        195                 200                 205

Phe Leu Phe Pro Pro Lys Pro Lys Asp Thr Leu Met Ile Ser Arg Thr
    210                 215                 220

Pro Glu Val Thr Cys Val Val Val Asp Val Ser His Glu Asp Pro Glu
225                 230                 235                 240

Val Lys Phe Asn Trp Tyr Val Asp Gly Val Glu Val His Asn Ala Lys
                245                 250                 255

Thr Lys Pro Arg Glu Glu Gln Tyr Asn Ser Thr Tyr Arg Val Val Ser
            260                 265                 270

Val Leu Thr Val Leu His Gln Asp Trp Leu Asn Gly Lys Glu Tyr Lys
        275                 280                 285

Cys Lys Val Ser Asn Lys Ala Leu Pro Ala Pro Ile Glu Lys Thr Ile
    290                 295                 300

Ser Lys Ala Lys Gly Gln Pro Arg Glu Pro Gln Val Tyr Thr Leu Pro
305                 310                 315                 320

Pro Ser Arg Glu Glu Met Thr Lys Asn Gln Val Ser Leu Thr Cys Leu
                325                 330                 335

Val Lys Gly Phe Tyr Pro Ser Asp Ile Ala Val Glu Trp Glu Ser Asn
            340                 345                 350

Gly Gln Pro Glu Asn Asn Tyr Lys Thr Thr Pro Pro Val Leu Asp Ser
        355                 360                 365

Asp Gly Ser Phe Phe Leu Tyr Ser Lys Leu Thr Val Asp Lys Ser Arg
    370                 375                 380

Trp Gln Gln Gly Asn Val Phe Ser Cys Ser Val Met His Glu Ala Leu
385                 390                 395                 400

His Asn His Tyr Thr Gln Lys Ser Leu Ser Leu Ser Pro Gly Lys
```

```
                      405                 410                 415

<210> SEQ ID NO 77
<211> LENGTH: 410
<212> TYPE: PRT
<213> ORGANISM: Artificial Sequence
<220> FEATURE:
<223> OTHER INFORMATION: Synthetic Polypeptide

<400> SEQUENCE: 77

Cys Thr Cys Ser Pro Ser His Pro Gln Asp Ala Phe Cys Asn Ser Asp
1               5                   10                  15

Ile Val Ile Arg Ala Asn Val Thr Gly Lys Lys Leu Val Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro Ala Pro Glu Leu
            180                 185                 190

Leu Gly Gly Pro Ser Val Phe Leu Phe Pro Pro Lys Pro Lys Asp Thr
        195                 200                 205

Leu Met Ile Ser Arg Thr Pro Glu Val Thr Cys Val Val Val Asp Val
    210                 215                 220

Ser His Glu Asp Pro Glu Val Lys Phe Asn Trp Tyr Val Asp Gly Val
225                 230                 235                 240

Glu Val His Asn Ala Lys Thr Lys Pro Arg Glu Glu Gln Tyr Asn Ser
                245                 250                 255

Thr Tyr Arg Val Val Ser Val Leu Thr Val Leu His Gln Asp Trp Leu
            260                 265                 270

Asn Gly Lys Glu Tyr Lys Cys Lys Val Ser Asn Lys Ala Leu Pro Ala
        275                 280                 285

Pro Ile Glu Lys Thr Ile Ser Lys Ala Lys Gly Gln Pro Arg Glu Pro
    290                 295                 300

Gln Val Thr Thr Leu Pro Pro Ser Arg Glu Glu Met Asn Lys Thr Gln
305                 310                 315                 320

Val Ser Leu Thr Cys Leu Val Lys Gly Phe Tyr Pro Ser Asp Ile Ala
                325                 330                 335

Val Glu Trp Glu Ser Asn Gly Gln Pro Glu Asn Asn Tyr Asp Thr Thr
            340                 345                 350

Pro Pro Val Leu Asp Ser Asp Gly Ser Phe Phe Leu Tyr Ser Asp Leu
```

```
                355                 360                 365
Thr Val Asp Lys Ser Arg Trp Gln Gln Gly Asn Val Phe Ser Cys Ser
370                 375                 380

Val Met His Glu Ala Leu His Asn His Tyr Thr Gln Lys Ser Leu Ser
385                 390                 395                 400

Leu Ser Pro Gly Lys Glu Pro Lys Ser Ser
                405                 410
```

<210> SEQ ID NO 78
<211> LENGTH: 415
<212> TYPE: PRT
<213> ORGANISM: Artificial Sequence
<220> FEATURE:
<223> OTHER INFORMATION: Synthetic Polypeptide

<400> SEQUENCE: 78

```
Cys Thr Cys Ser Pro Ser His Pro Gln Asp Ala Phe Cys Asn Ser Asp
1               5                   10                  15

Ile Val Ile Arg Ala Lys Val Val Gly Lys Lys Leu Val Lys Glu Gly
                20                  25                  30

Pro Phe Gly Thr Leu Val Tyr Thr Ile Lys Gln Met Lys Met Tyr Arg
            35                  40                  45

Gly Phe Thr Lys Met Pro Asn Val Thr Tyr Ile His Thr Glu Ala Ser
50                  55                  60

Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro Asp Lys Thr His
            180                 185                 190

Thr Cys Pro Pro Cys Pro Ala Pro Glu Leu Leu Gly Gly Pro Ser Val
        195                 200                 205

Phe Leu Phe Pro Pro Lys Pro Lys Asp Thr Leu Met Ile Ser Arg Thr
210                 215                 220

Pro Glu Val Thr Cys Val Val Asp Val Ser His Glu Asp Pro Glu
225                 230                 235                 240

Val Lys Phe Asn Trp Tyr Val Asp Gly Val Glu Val His Asn Ala Lys
                245                 250                 255

Thr Lys Pro Arg Glu Glu Gln Tyr Asn Ser Thr Tyr Arg Val Val Ser
            260                 265                 270

Val Leu Thr Val Leu His Gln Asp Trp Leu Asn Gly Lys Glu Tyr Lys
        275                 280                 285

Cys Lys Val Ser Asn Lys Ala Leu Pro Ala Pro Ile Glu Lys Thr Ile
290                 295                 300

Ser Lys Ala Lys Gly Gln Pro Arg Glu Pro Gln Val Tyr Thr Leu Pro
```

```
                305                 310                 315                 320
Pro Ser Arg Glu Glu Met Thr Lys Asn Gln Val Ser Leu Thr Cys Leu
                325                 330                 335

Val Lys Gly Phe Tyr Pro Ser Asp Ile Ala Val Glu Trp Glu Ser Asn
                340                 345                 350

Gly Gln Pro Glu Asn Asn Tyr Lys Thr Thr Pro Pro Val Leu Asp Ser
                355                 360                 365

Asp Gly Ser Phe Phe Leu Tyr Ser Lys Leu Thr Val Asp Lys Ser Arg
                370                 375                 380

Trp Gln Gln Gly Asn Val Phe Ser Cys Ser Val Met His Glu Ala Leu
385                 390                 395                 400

His Asn His Tyr Thr Gln Lys Ser Leu Ser Leu Ser Pro Gly Lys
                405                 410                 415

<210> SEQ ID NO 79
<211> LENGTH: 410
<212> TYPE: PRT
<213> ORGANISM: Artificial Sequence
<220> FEATURE:
<223> OTHER INFORMATION: Synthetic Polypeptide

<400> SEQUENCE: 79

Cys Thr Cys Ser Pro Ser His Pro Gln Asp Ala Phe Cys Asn Ser Asp
1               5                   10                  15

Ile Val Ile Arg Ala Lys Val Val Gly Lys Lys Leu Val Lys Glu Gly
                20                  25                  30

Pro Phe Gly Thr Leu Val Tyr Thr Ile Lys Gln Met Lys Met Tyr Arg
                35                  40                  45

Gly Phe Thr Lys Met Pro Asn Val Thr Tyr Ile His Thr Glu Ala Ser
            50                  55                  60

Glu Ser Leu Cys Gly Leu Asn Leu Thr Val Asn Lys Tyr Gln Tyr Leu
65              70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
                100                 105                 110

Asn Tyr Thr Tyr His Leu Gly Cys Asn Cys Lys Ile Lys Ser Cys Tyr
                115                 120                 125

Tyr Leu Pro Cys Phe Val Thr Ser Lys Asn Glu Cys Leu Trp Thr Asp
            130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro Ala Pro Glu Leu
                180                 185                 190

Leu Gly Gly Pro Ser Val Phe Leu Phe Pro Pro Lys Pro Lys Asp Thr
                195                 200                 205

Leu Met Ile Ser Arg Thr Pro Glu Val Thr Cys Val Val Val Asp Val
            210                 215                 220

Ser His Glu Asp Pro Glu Val Lys Phe Asn Trp Tyr Val Asp Gly Val
225                 230                 235                 240

Glu Val His Asn Ala Lys Thr Lys Pro Arg Glu Glu Gln Tyr Asn Ser
                245                 250                 255

Thr Tyr Arg Val Val Ser Val Leu Thr Val Leu His Gln Asp Trp Leu
```

```
                       260                    265                    270
Asn Gly Lys Glu Tyr Lys Cys Lys Val Ser Asn Lys Ala Leu Pro Ala
            275                    280                    285

Pro Ile Glu Lys Thr Ile Ser Lys Ala Lys Gly Gln Pro Arg Glu Pro
            290                    295                    300

Gln Val Thr Thr Leu Pro Pro Ser Arg Glu Glu Met Asn Lys Thr Gln
305                    310                    315                    320

Val Ser Leu Thr Cys Leu Val Lys Gly Phe Tyr Pro Ser Asp Ile Ala
                 325                    330                    335

Val Glu Trp Glu Ser Asn Gly Gln Pro Glu Asn Asn Tyr Asp Thr Thr
                 340                    345                    350

Pro Pro Val Leu Asp Ser Asp Gly Ser Phe Phe Leu Tyr Ser Asp Leu
            355                    360                    365

Thr Val Asp Lys Ser Arg Trp Gln Gln Gly Asn Val Phe Ser Cys Ser
            370                    375                    380

Val Met His Glu Ala Leu His Asn His Tyr Thr Gln Lys Ser Leu Ser
385                    390                    395                    400

Leu Ser Pro Gly Lys Glu Pro Lys Ser Ser
                 405                    410
```